(12) United States Patent
Jorand-Lebrun et al.

(10) Patent No.: US 9,969,710 B2
(45) Date of Patent: May 15, 2018

(54) HETEROARYL COMPOUNDS AS IRAK INHIBITORS AND USES THEREOF

(71) Applicant: Merck Patent GmbH, Darmstadt (DE)

(72) Inventors: Catherine Jorand-Lebrun, Arlington, MA (US); Ruoxi Lan, Waltham, MA (US); Austin Chen, San Marco, CA (US); Ryan C. Clark, San Diego, CA (US)

(73) Assignee: Merck Patent GmbH, Darmstadt (DE)

( * ) Notice: Subject to any disclaimer, the term of this patent is extended or adjusted under 35 U.S.C. 154(b) by 0 days. days.

(21) Appl. No.: 15/267,606

(22) Filed: Sep. 16, 2016

(65) Prior Publication Data

US 2017/0081307 A1 Mar. 23, 2017

Related U.S. Application Data

(60) Provisional application No. 62/220,358, filed on Sep. 18, 2015.

(51) Int. Cl.

| | |
|---|---|
| *A61K 31/4439* | (2006.01) |
| *A61K 31/506* | (2006.01) |
| *A61K 31/4184* | (2006.01) |
| *C07D 401/04* | (2006.01) |
| *C07D 403/04* | (2006.01) |
| *C07D 405/04* | (2006.01) |
| *C07D 413/04* | (2006.01) |
| *C07D 451/02* | (2006.01) |
| *C07D 235/30* | (2006.01) |
| *C07D 471/08* | (2006.01) |

(52) U.S. Cl.
CPC ........ *C07D 401/04* (2013.01); *A61K 31/4184* (2013.01); *A61K 31/4439* (2013.01); *A61K 31/506* (2013.01); *C07D 235/30* (2013.01); *C07D 403/04* (2013.01); *C07D 405/04* (2013.01); *C07D 413/04* (2013.01); *C07D 451/02* (2013.01); *C07D 471/08* (2013.01)

(58) Field of Classification Search
None
See application file for complete search history.

(56) References Cited

U.S. PATENT DOCUMENTS

| 9,440,957 B2 * | 9/2016 | Lelais ............... A61K 31/4184 |
| 2005/0209284 A1 * | 9/2005 | Bentzien ............ C07D 235/30 |
| | | 514/338 |
| 2007/0117818 A1 * | 5/2007 | Hasegawa ........... C07D 401/04 |
| | | 514/269 |
| 2008/0255120 A1 * | 10/2008 | Lin ..................... C07D 409/04 |
| | | 514/235.8 |

FOREIGN PATENT DOCUMENTS

| WO | 2003030902 A1 | 4/2003 |
| WO | 2005076854 A2 | 8/2005 |
| WO | 2005095386 A1 | 10/2005 |
| WO | 2006099379 A2 | 9/2006 |
| WO | 2010126743 A1 | 11/2010 |
| WO | 2010126745 A1 | 11/2010 |
| WO | 2011119465 A1 | 9/2011 |
| WO | 2013184757 A1 | 12/2013 |

OTHER PUBLICATIONS

Cohen, Current Opinion in Cell Biology 21, 317-324 (2009.
Ringwood and Li, Cytokine 42, 1-7 (2008).
Cao et al., Science 271(5252): 1128-31 (1996).
Muzio et al., Science 278(5343): 1612-5 (1997).
Wesche et al. J. Biol. Chem. 274(27): 19403-10 (1999).
Li et al. Proc. Natl. Acad. Sci. USA 99(8):5567-5572 (2002).
Buckley et al. Bioorg Med Chem Lett. 18(12):3656-60 (2008).
Periodic Table of the Elements, CAS Version, Handbook of Chemistry and Physics, 75th Ed.
"Organic Chemistry", Thomas Sorrell, University Science Books, Sausalito (1999).
"March's Advanced Organic Chemistry", 5th Ed., Ed.: Smith, M.B. and March, J., John Wiley & Sons, New York: (2001).
S. M. Berge et al., J. Pharmaceutical Sciences, 66, 1-19 (1977).
Hanzlik et al., J. Org. Chem. 55, 3992-3997 (1990).
Reider et al., J. Org. Chem. 52, 3326-3334 (1987).
Foster, Adv. Drug Res. 14, 1-40 (1985).
Gillette et al., Biochemistry 33(10) 2927-2937 (1994).
Jarman et al., Carcinogenesis 16(4), 683-688 (1993).
Philip J. Kocienski, "Protecting Groups", Georg Thieme Verlag Stuttgart, New York, (1994).
Theodora W. Greene and Peter G. M. Wuts, "Protective Groups in Organic Synthesis", Wiley Interscience, 3rd Edition (1999).
Ding et al., Bioorganic and Medicinal Chemistry Letters, (24):3113-3117 (2014).
Hranjec et al., European Journal of Medicinal Chemistry, 59:111-119 (2012).
Sovic et al., Chemical Monthly, Vienna 146(9):1503-1517 (2015).

* cited by examiner

*Primary Examiner* — Samantha L Shterengarts
(74) *Attorney, Agent, or Firm* — Dwight D. Kim; EMD Serono Research and Development Institute

(57) ABSTRACT

The present invention relates to compounds of Formula I and pharmaceutically acceptable compositions thereof, useful as IRAK inhibitors.

20 Claims, No Drawings

HETEROARYL COMPOUNDS AS IRAK INHIBITORS AND USES THEREOF

RELATED APPLICATIONS

The present application claims the benefit of U.S. provisional application 62/220,358, filed on Sep. 18, 2015, the contents of which are incorporated herein in its entirety by reference.

TECHNICAL FIELD OF THE INVENTION

The present invention provides for compounds of Formula (I) as IRAK inhibitors and their use in the treatment of cancer, and other diseases related to IRAK overexpression, including rheumatoid arthritis, systemic lupus erythematosus or lupus nephritis.

BACKGROUND OF THE INVENTION

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAKI (Muzio et al., 1997. Science 278 (5343): 1612-5). IRAK3 (also called IRAKM) was identified using a murine EST sequence encoding a polypeptide with significant homology to IRAK1 to screen a human phytohemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

In one aspect, the invention provides compounds of Formula (I):

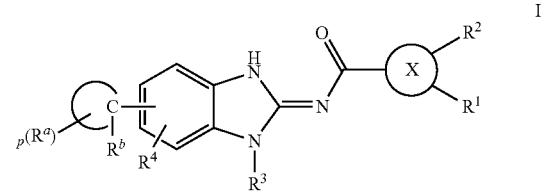

and pharmaceutically acceptable derivatives, solvates, salts, hydrates and stereoisomers thereof, wherein Ring X, $R^1$, $R^2$, $R^3$, $R^4$, $R^a$, $R^b$, and p, is as defined below and described in the embodiments.

In another aspect, the invention provides compounds of Formula (I) which are suitable for the treatment and/or prevention of disorders related to IRAK. In another aspect, the invention provides compounds which are able to modulate, especially inhibit the activity or function of IRAK in disease states in mammals, especially in humans.

According to another aspect of the invention are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I) which are selective for IRAK-4 and/or IRAK-1.

According to another aspect, the present invention provides compounds of Formula (I) which are selective for IRAK-4 and IRAK-1.

DETAILED DESCRIPTION OF CERTAIN EMBODIMENTS

1. General Description of Compounds of the Invention

In certain aspects, the present invention provides for inhibitors of IRAK. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NW$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

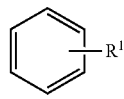

refers to at least

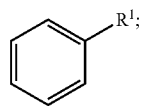

and

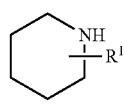

refers to at least

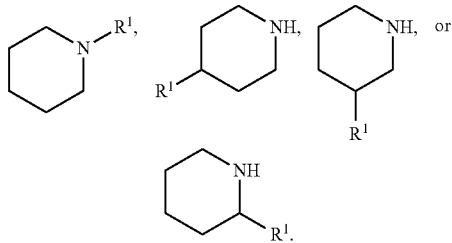

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH═CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet$3, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH -aryl, —NH -heteroaryl, —NH -heterocyclic, -dialkylamino, -diarylamino, -diheteroarylamino, —O— alkyl, —O— alkenyl, —O— alkynyl, —O— cycloalkyl, —O-aryl, —O-heteroaryl, —O— heterocyclic, —C(O)— alkyl, —C(O)— alkenyl, —C(O)— alkynyl, —C(O)— carbocyclyl, —C(O)-aryl, —C(O)— heteroaryl, —C(O)— heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH— -alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)— heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$— aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S—aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. For example, the invention contemplates tautomers of the following formulae, so long as valency and/or other chemical requirements are satisfied:

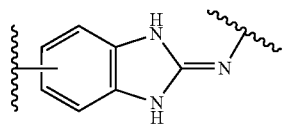

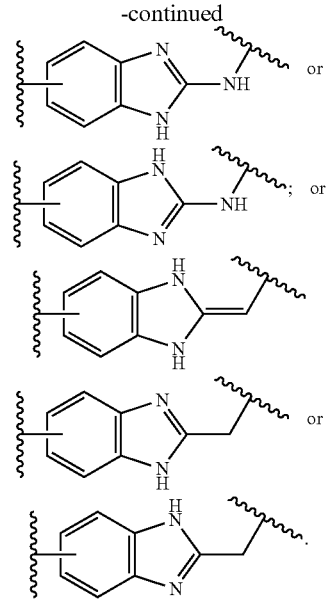

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a corn-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an IC$_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in IRAK activity between a sample comprising a compound of the present invention, or composition thereof, and IRAK, and an equivalent sample comprising IRAK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

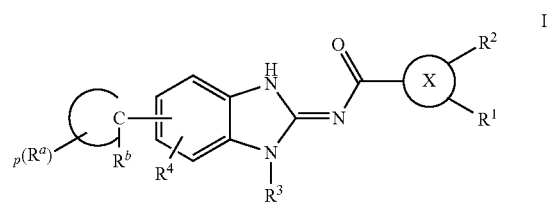

or a pharmaceutically acceptable salt thereof, wherein:

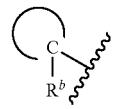

is a C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur;

each R$^a$ is independently —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

R$^b$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$; or R$^b$ is absent;

Ring X is a C$_{3-10}$ aryl; a 5-6 membered monocyclic heteroaryl ring having 1-4 heteroatoms independently selected from nitrogen, oxygen, or sulfur; a fused C$_{3-10}$ aryl, a fused 5-10 membered saturated or partially unsaturated carbocyclic ring, a fused 5-10 membered heterocyclic ring having 1-4 heteroatoms independently selected from nitrogen, oxygen, or sulfur, or a fused 5-10 membered monocyclic heteroaryl ring having 1-4 heteroatoms independently selected from nitrogen, oxygen, or sulfur; each of which is optionally substituted;

R$^1$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

R$^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

R$^3$ is —R or -haloalkyl;

R$^4$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

each R is independently hydrogen, C$_{1-6}$ aliphatic, C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; and p is 0, 1, 2, 3, 4, or 5.

In certain embodiments,

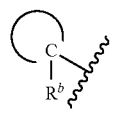

is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl.

In certain embodiments,

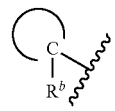

is cyclohexyl, furanyl, dihydrofuranyl, piperidinyl, pyridinyl, dihydropyridinyl, pyridyl, pyrimidinyl, dihydropyrimidine, pyrrolidinyl, or, oxetanyl.

In certain embodiments,

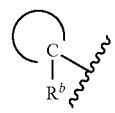

is cyclohexanone, furanone, piperidinone, pyridinone, pyrimidinone, pyrrolidinone, or oxetanyl.

In certain embodiments, ring

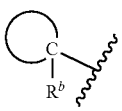

is selected from:

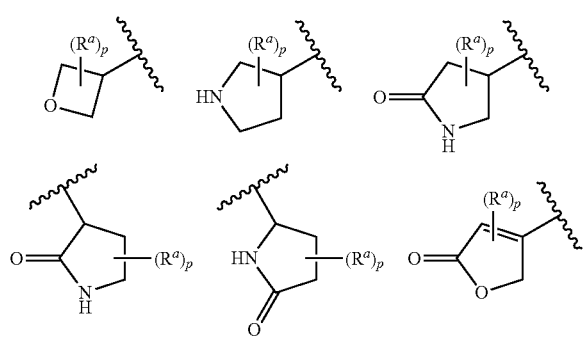

-continued

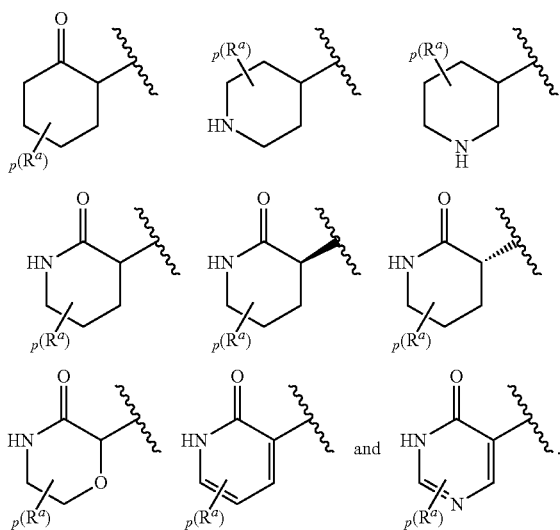

In certain embodiments, ring

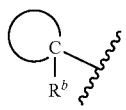

is selected from:

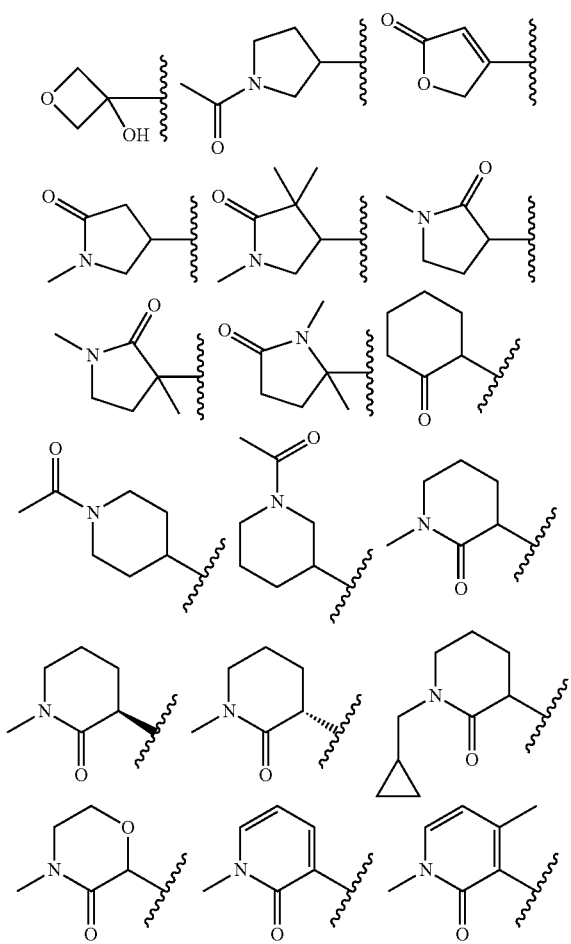

-continued

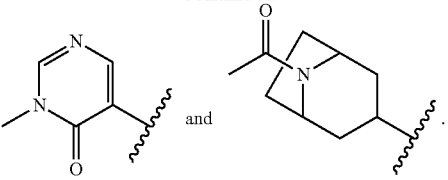

In certain embodiments, Ring X is an optionally substituted $C_{3-10}$ aryl. In certain embodiments, Ring X is an optionally substituted 5-6 membered monocyclic heteroaryl ring having 1-4 heteroatoms independently selected from nitrogen, oxygen, or sulfur. In certain embodiments, Ring X is an optionally substituted fused $C_{3-10}$ aryl. In certain embodiments, Ring X is an optionally substituted fused 5-10 membered saturated or partially unsaturated carbocyclic ring. In certain embodiments, Ring X is an optionally substituted fused 5-10 membered heterocylic ring having 1-4 heteroatoms independently selected from nitrogen, oxygen, or sulfur. In certain embodiments, Ring X is an optionally substituted fused 5-10 membered monocyclic heteroaryl ring having 1-4 heteroatoms independently selected from nitrogen, oxygen, or sulfur.

In certain embodiments, Ring X is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, Ring X is an optionally substituted $C_{3-10}$ aryl; an optionally substituted 5-6 membered monocyclic heteroaryl ring having 1-4 heteroatoms independently selected from nitrogen, oxygen, or sulfur; an optionally substituted fused $C_{3-10}$ aryl; or an optionally substituted fused 5-10 membered monocyclic heteroaryl ring having 1-4 heteroatoms independently selected from nitrogen, oxygen, or sulfur.

In certain embodiments, Ring X is phenyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isoindazolyl, isoindolinyl, isoindolyl, isoquinolinyl, isothiazolyl, isoxazolyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, tetrazole, triazinyl, 1,2,3-triazolyl, 1,2,4-triazolyl, 1,2,5-triazolyl, or 1,3,4-triazolyl; each of which is optionally substituted.

In certain embodiments, Ring X is phenyl, benzimidazolyl, benzofuranyl, benzothiofuranyl, benzothiophenyl, 1H-indazolyl, isobenzofuranyl, isoxazolyl, pyrazinyl, pyrazolyl, pyridinyl, pyridyl, or tetrazole; each of which is optionally substituted.

In certain embodiments, Ring X is selected from:

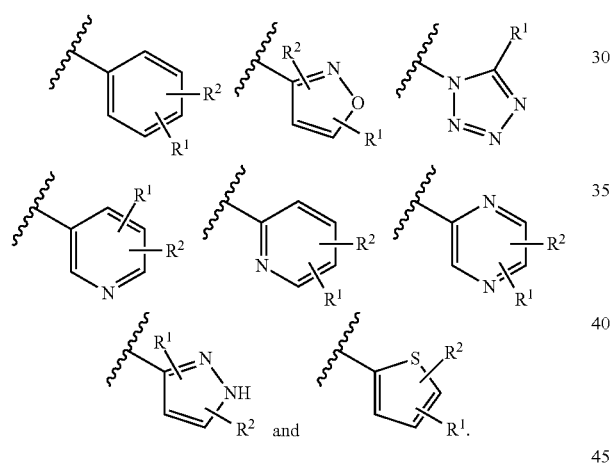

In certain embodiments, Ring X is

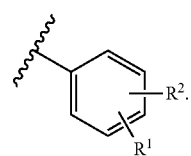

In certain embodiments, Ring X is selected from:

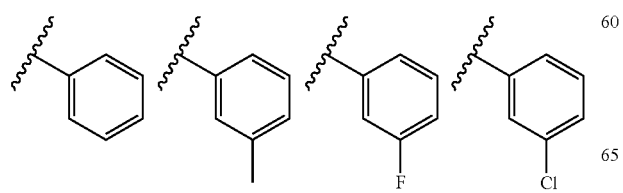

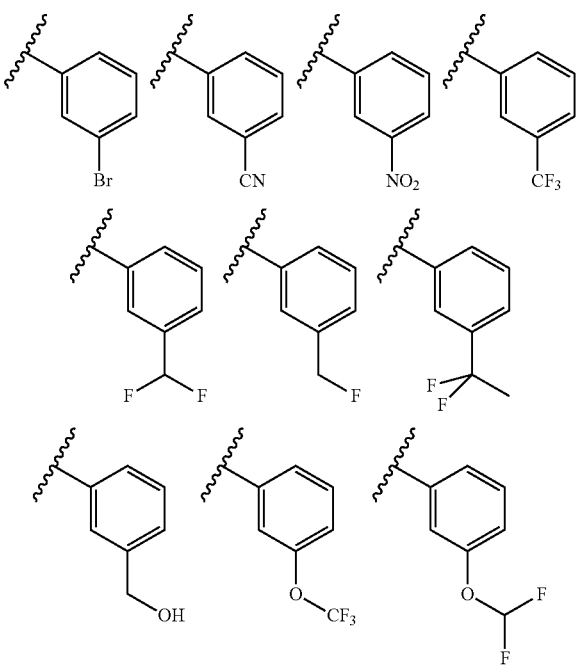

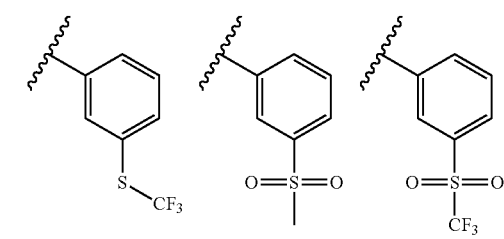

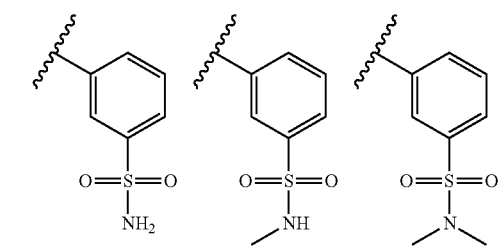

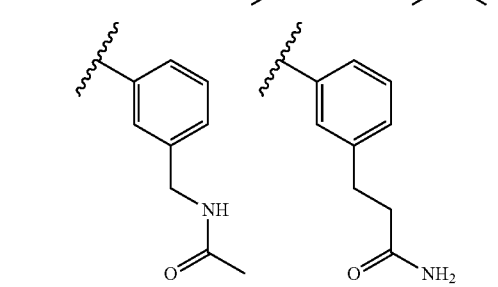

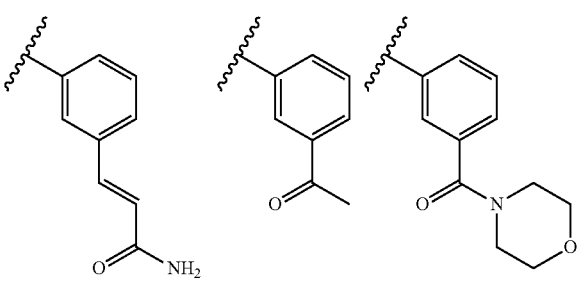

-continued

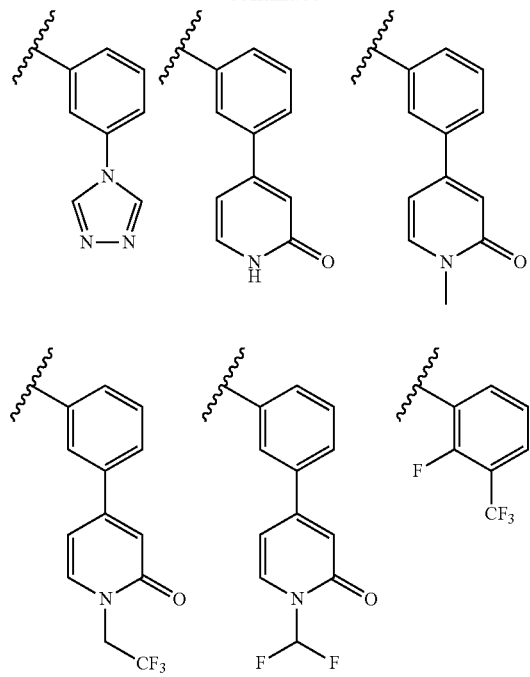

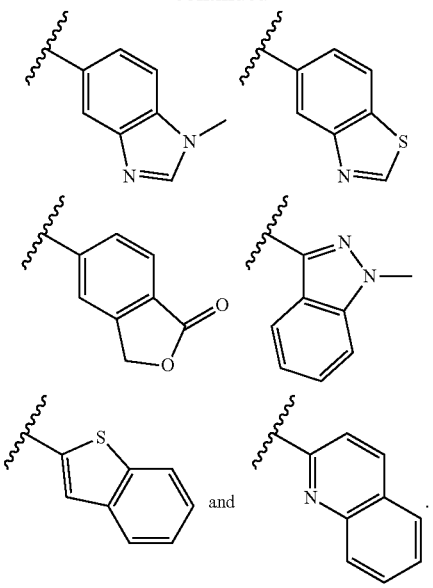

and

In certain embodiments, Ring X is:

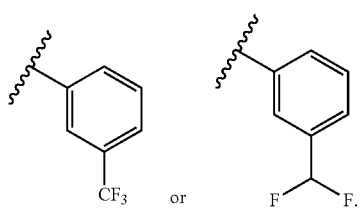 [SMILES: *c1cccc(C(F)(F)F)c1 ; *c1cccc(C(F)F)c1]

In certain embodiments, R³ is —R.

In certain embodiments, R³ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R³ is $C_{1-6}$ aliphatic, a 3-8 membered saturated or partially unsaturated carbocyclic ring, or a 3-7 membered heterocylic ring having 1-4 heteroatoms independently selected from nitrogen, oxygen, or sulfur; each of which is optionally substituted.

In certain embodiments, R³ is methyl, ethyl, propyl, i-propyl, n-butyl, s-butyl, t-butyl, a straight chain or branched pentyl, or a straight chain or branched hexyl; each of which is optionally substituted.

In certain embodiments, R³ is selected from:

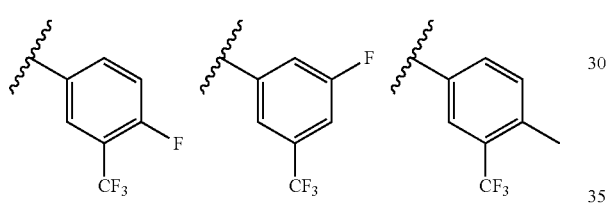

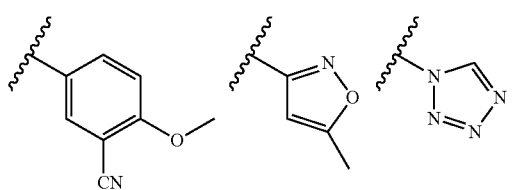

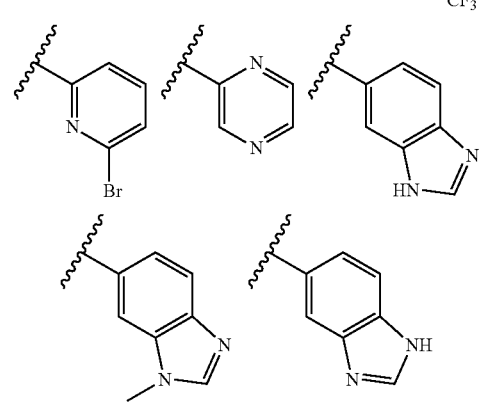

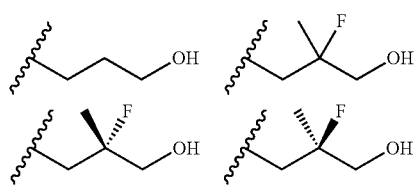

-continued

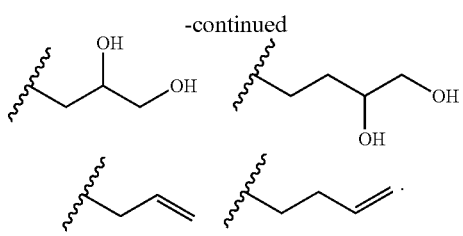

In certain embodiments, $R^3$ is

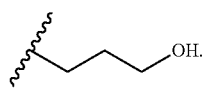 [SMILES: *CCCO]

In certain embodiments, $R^3$ is

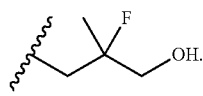 [SMILES: *CC(C)(F)CO]

In certain embodiments, $R^3$ is

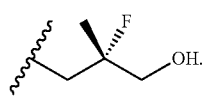 [SMILES: *C[C@](C)(F)CO]

In certain embodiments, $R^3$ is

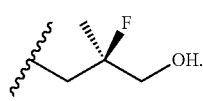 [SMILES: *C[C@@](C)(F)CO]

In certain embodiments, $R^3$ is

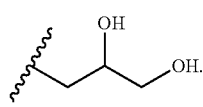

In certain embodiments, $R^3$ is

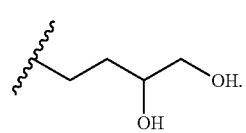

In certain embodiments, $R^3$ is

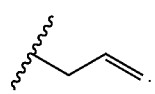

In certain embodiments, $R^3$ is

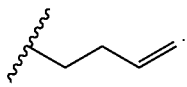 [SMILES: *CCC=C]

In certain embodiments, each of Ring X, R, $R^1$, $R^2$, $R^3$, $R^4$, $R^a$, $R^b$, and p, is as defined above and described in embodiments, classes and subclasses above and herein, singly or in combination.

In certain embodiments, the present invention provides a compound of formula I-a,

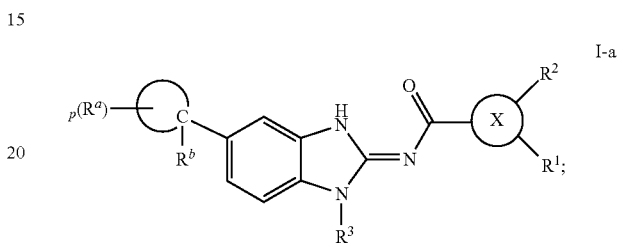

I-a or a pharmaceutically acceptable salt thereof, wherein each of Ring X, $R^1$, $R^2$, $R^3$, $R^a$, $R^b$, and p, is as defined above and described in embodiments, classes and subclasses above and herein, singly or in combination.

In certain embodiments, the present invention provides a compound of formula I-b,

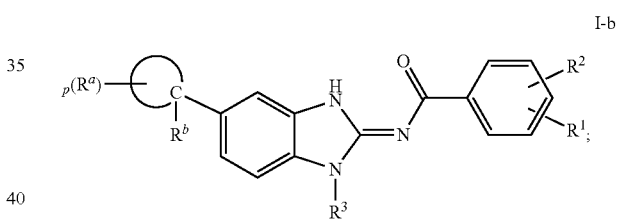

I-b or a pharmaceutically acceptable salt thereof, wherein each of $R^1$, $R^2$, $R^3$, $R^a$, $R^b$, and p, is as defined above and described in embodiments, classes and subclasses above and herein, singly or in combination.

In certain embodiments, the present invention provides a compound of formula I-c,

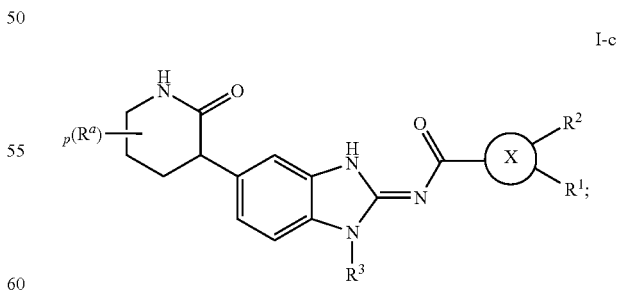

I-c or a pharmaceutically acceptable salt thereof, wherein each of Ring X, $R^1$, $R^2$, $R^3$, $R^a$, and p, is as defined above and described in embodiments, classes and subclasses above and herein, singly or in combination.

In certain embodiments, the invention provides a compound selected from Table 1:

TABLE 1
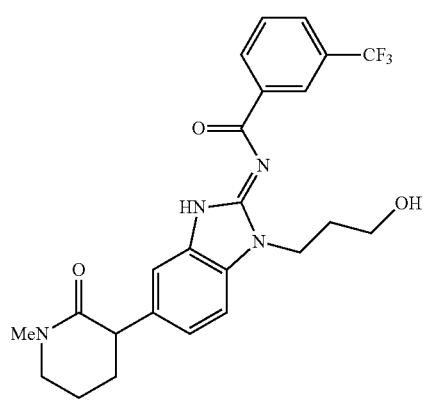 [SMILES: CN1CCCC(c2ccc3c(c2)[nH]/c(=N\C(=O)c2cccc(C(F)(F)F)c2)n3CCCO)C1=O]
1
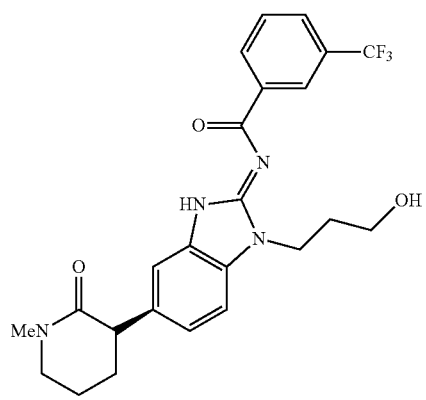
1a
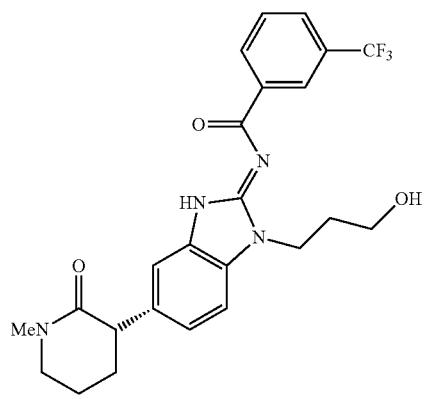
1b
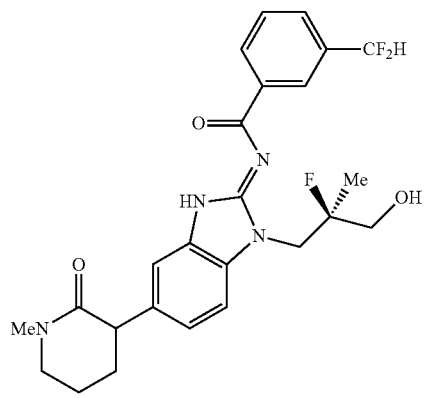 [SMILES: CN1CCCC(c2ccc3c(c2)[nH]/c(=N\C(=O)c2cccc(C(F)F)c2)n3C[C@@](C)(F)CO)C1=O]
2a
TABLE 1-continued
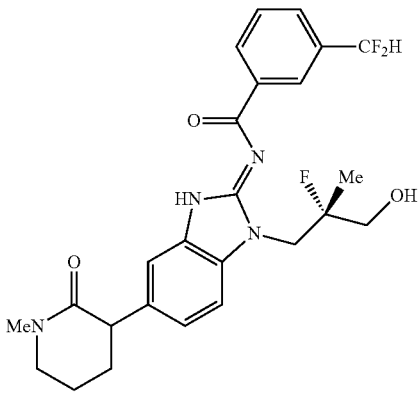 [SMILES: CN1CCCC(c2ccc3c(c2)[nH]/c(=N\C(=O)c2cccc(C(F)F)c2)n3C[C@](C)(F)CO)C1=O]
2b
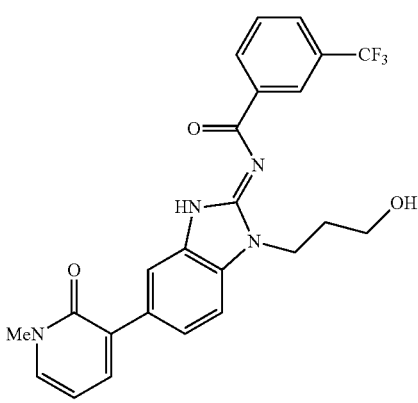 [SMILES: Cn1cccc(-c2ccc3c(c2)[nH]/c(=N\C(=O)c2cccc(C(F)(F)F)c2)n3CCCO)c1=O]
4
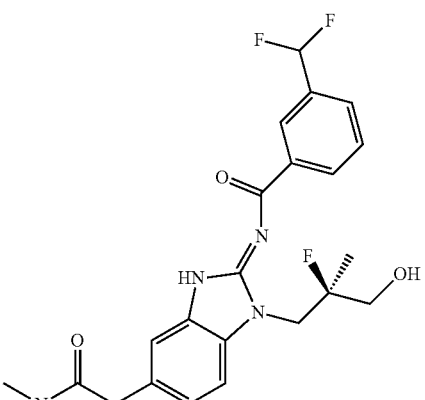
3a TABLE 1-continued
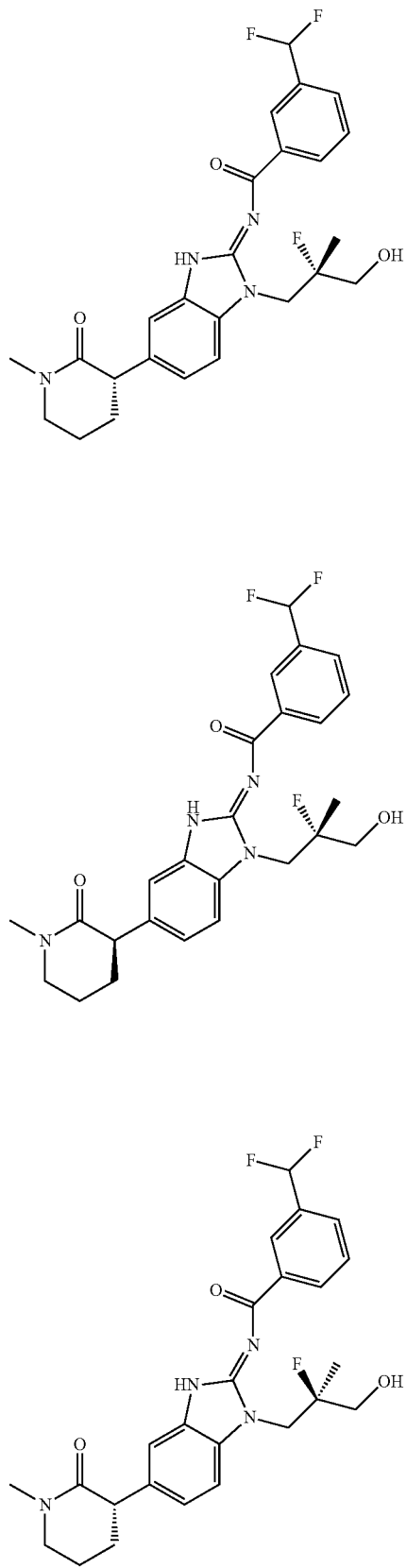
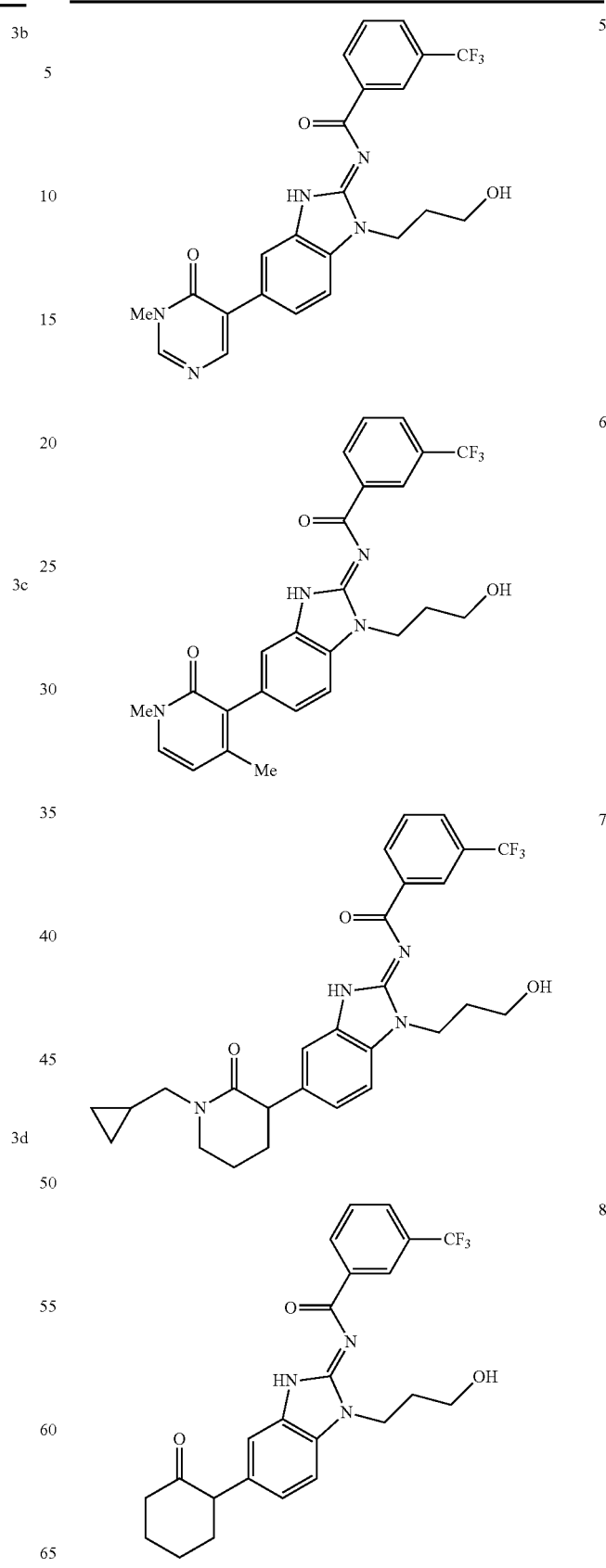

TABLE 1-continued
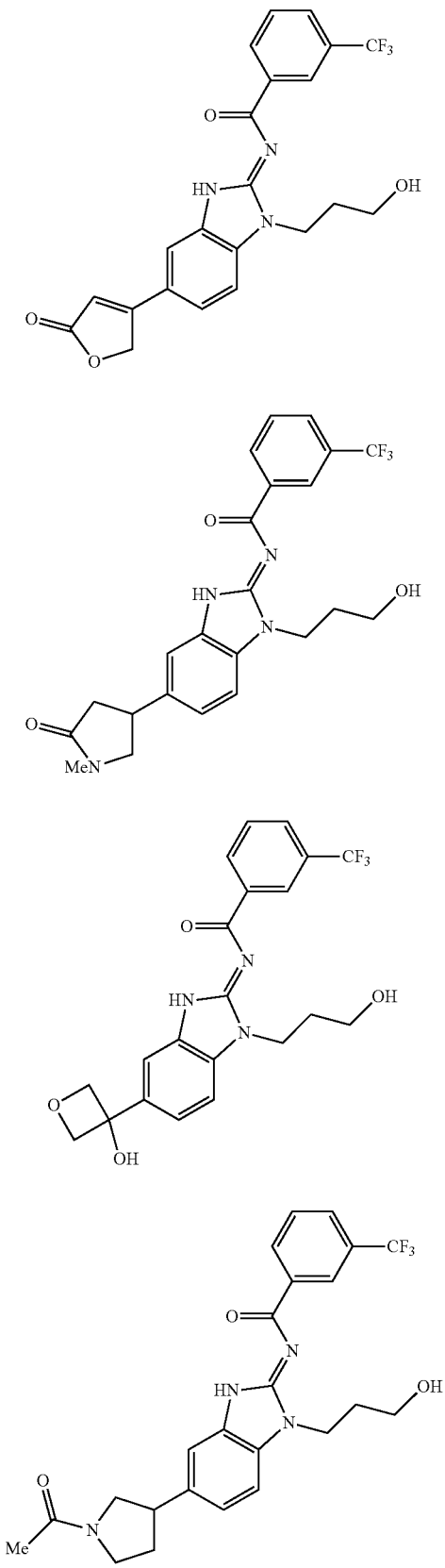
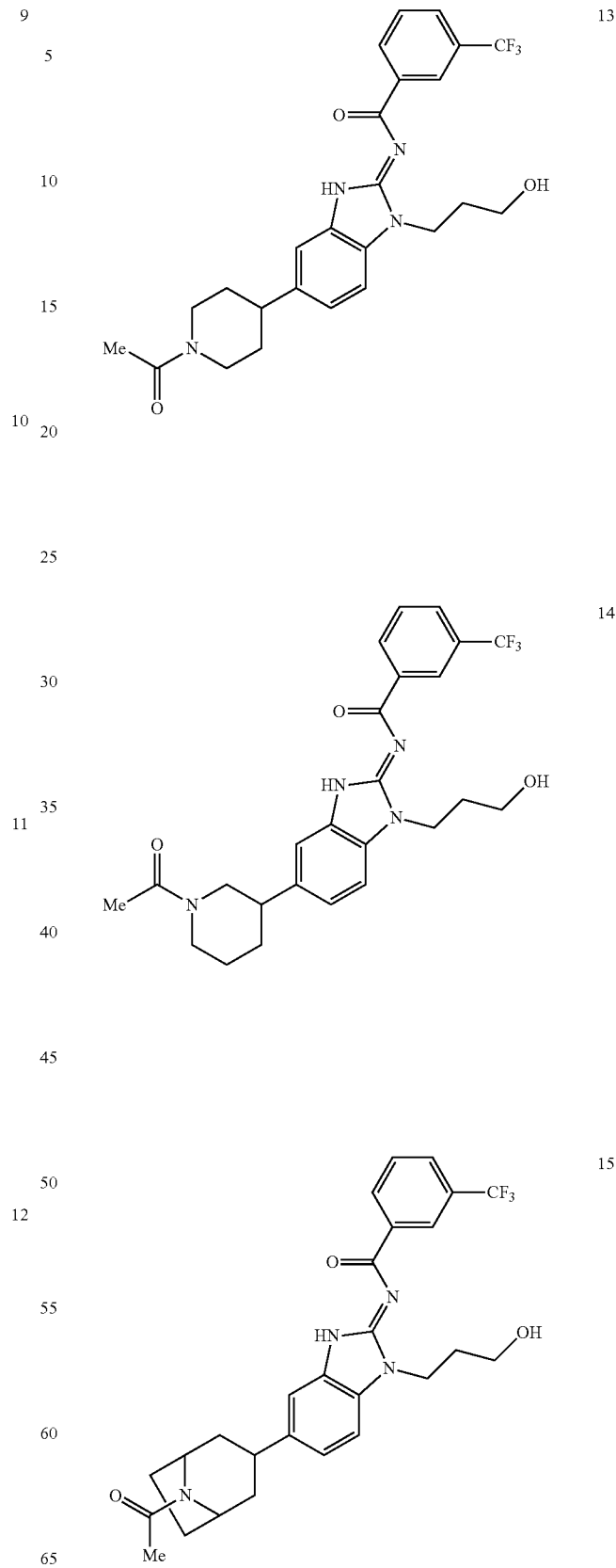

TABLE 1-continued
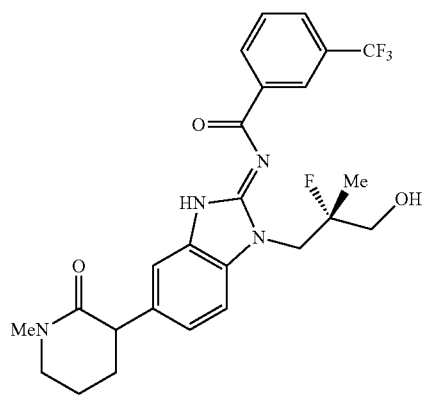 [SMILES: CN1CCCC(c2ccc3c(c2)[nH]/c(=N\C(=O)c2cccc(C(F)(F)F)c2)n3C[C@](C)(F)CO)C1=O] 16
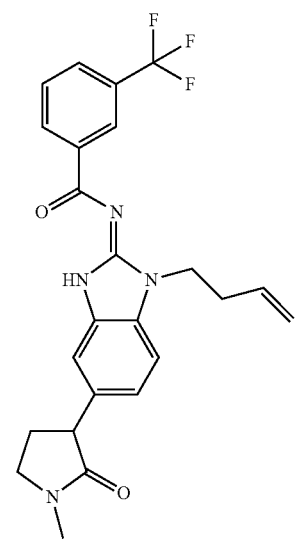 [SMILES: C=CCCn1/c(=N/C(=O)c2cccc(C(F)(F)F)c2)[nH]c2cc(C3CCN(C)C3=O)ccc21] 17
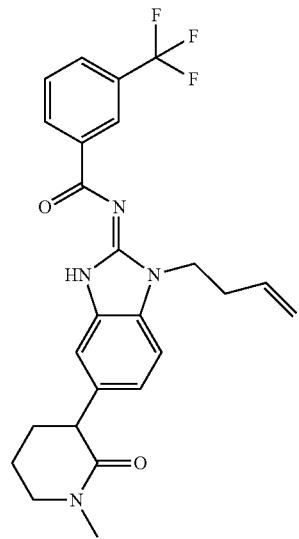 [SMILES: C=CCCn1/c(=N/C(=O)c2cccc(C(F)(F)F)c2)[nH]c2cc(C3CCCN(C)C3=O)ccc21] 18
TABLE 1-continued
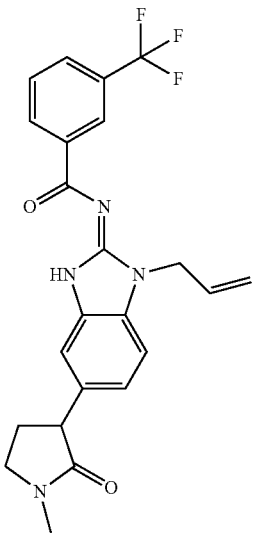 [SMILES: C=CCn1/c(=N/C(=O)c2cccc(C(F)(F)F)c2)[nH]c2cc(C3CCN(C)C3=O)ccc21] 19
20
20a TABLE 1-continued
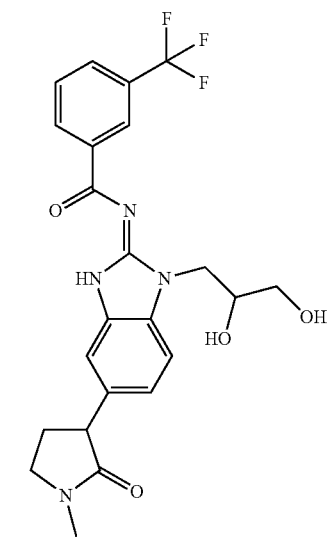 [SMILES: CN1CCC(c2ccc3c(c2)[nH]/c(=N\C(=O)c2cccc(C(F)(F)F)c2)n3CC(O)CO)C1=O]
20b
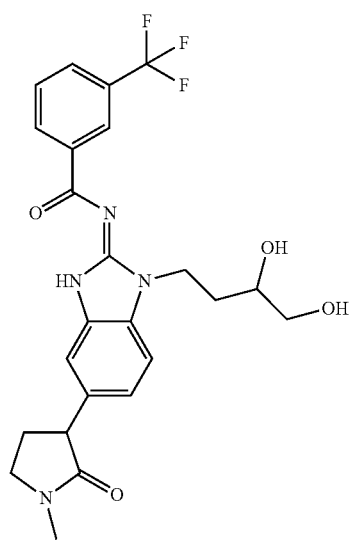 [SMILES: CN1CCC(c2ccc3c(c2)[nH]/c(=N\C(=O)c2cccc(C(F)(F)F)c2)n3CCC(O)CO)C1=O]
21
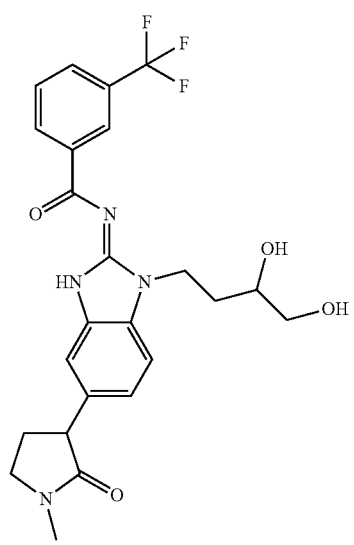 [SMILES: CN1CCC(c2ccc3c(c2)[nH]/c(=N\C(=O)c2cccc(C(F)(F)F)c2)n3CCC(O)CO)C1=O]
21a
TABLE 1-continued
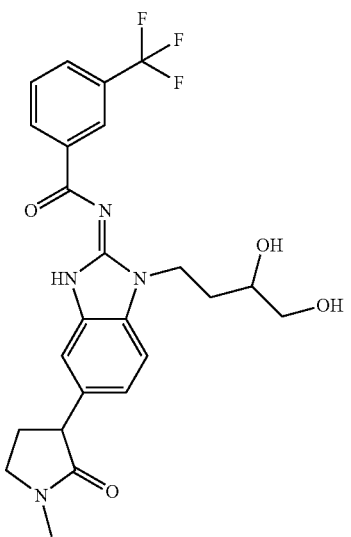 [SMILES: CN1CCC(c2ccc3c(c2)[nH]/c(=N\C(=O)c2cccc(C(F)(F)F)c2)n3CCC(O)CO)C1=O]
21b
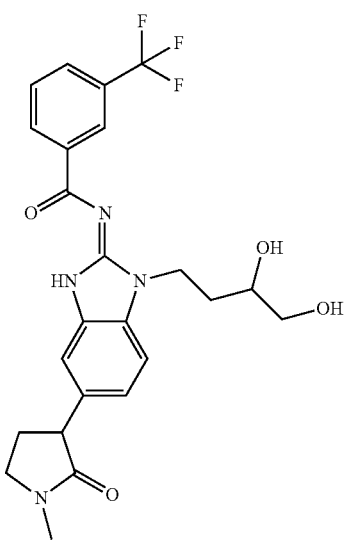 [SMILES: CN1CCC(c2ccc3c(c2)[nH]/c(=N\C(=O)c2cccc(C(F)(F)F)c2)n3CCC(O)CO)C1=O]
21c
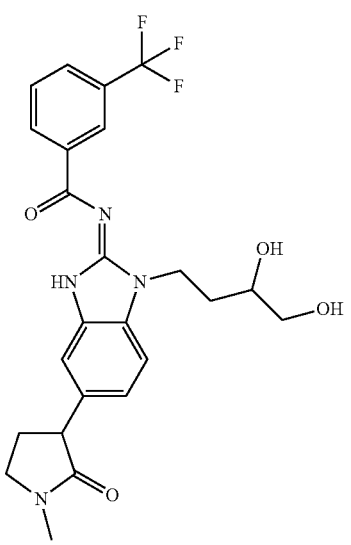 [SMILES: CN1CCC(c2ccc3c(c2)[nH]/c(=N\C(=O)c2cccc(C(F)(F)F)c2)n3CCC(O)CO)C1=O]
21d TABLE 1-continued
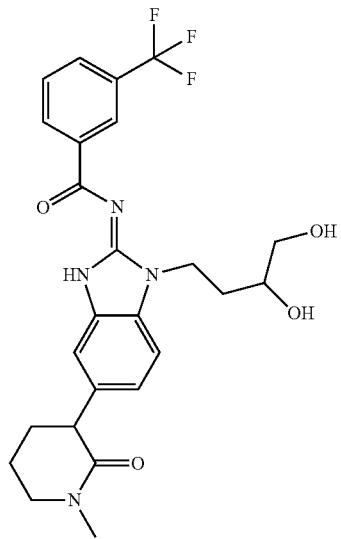 [SMILES: CN1CCCC(c2ccc3c(c2)[nH]/c(=N\C(=O)c2cccc(C(F)(F)F)c2)n3CCC(O)CO)C1=O]
22
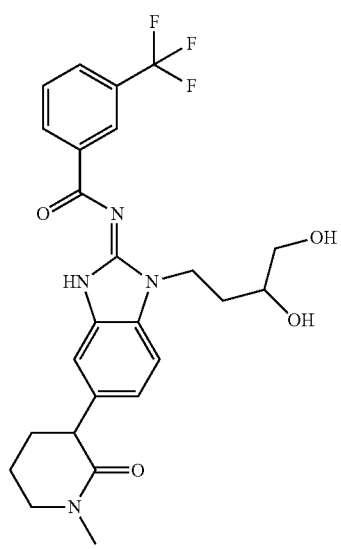 [SMILES: CN1CCCC(c2ccc3c(c2)[nH]/c(=N\C(=O)c2cccc(C(F)(F)F)c2)n3CCC(O)CO)C1=O]
22a
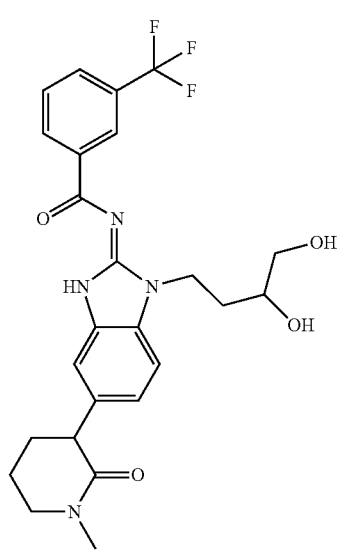 [SMILES: CN1CCCC(c2ccc3c(c2)[nH]/c(=N\C(=O)c2cccc(C(F)(F)F)c2)n3CCC(O)CO)C1=O]
22b
TABLE 1-continued
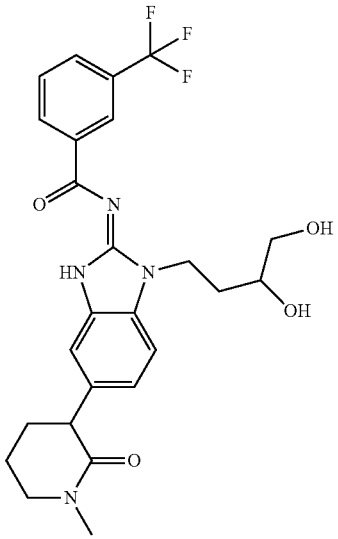 [SMILES: CN1CCCC(c2ccc3c(c2)[nH]/c(=N\C(=O)c2cccc(C(F)(F)F)c2)n3CCC(O)CO)C1=O]
22c
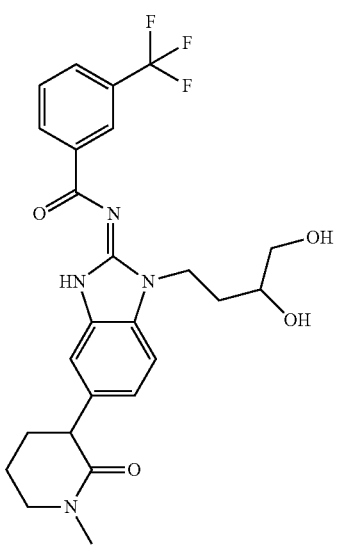 [SMILES: CN1CCCC(c2ccc3c(c2)[nH]/c(=N\C(=O)c2cccc(C(F)(F)F)c2)n3CCC(O)CO)C1=O]
22d
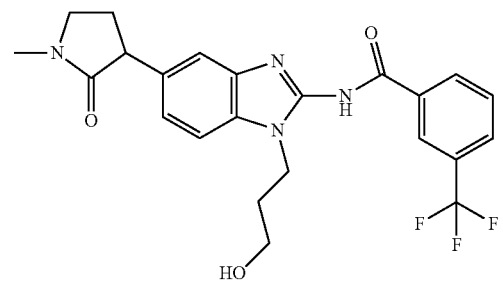 [SMILES: CN1CCC(c2ccc3c(c2)nc(NC(=O)c2cccc(C(F)(F)F)c2)n3CCCO)C1=O]
23
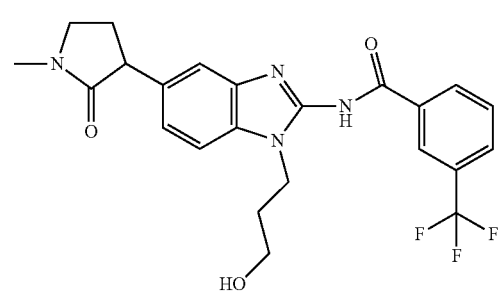 [SMILES: CN1CCC(c2ccc3c(c2)nc(NC(=O)c2cccc(C(F)(F)F)c2)n3CCCO)C1=O]
23a TABLE 1-continued
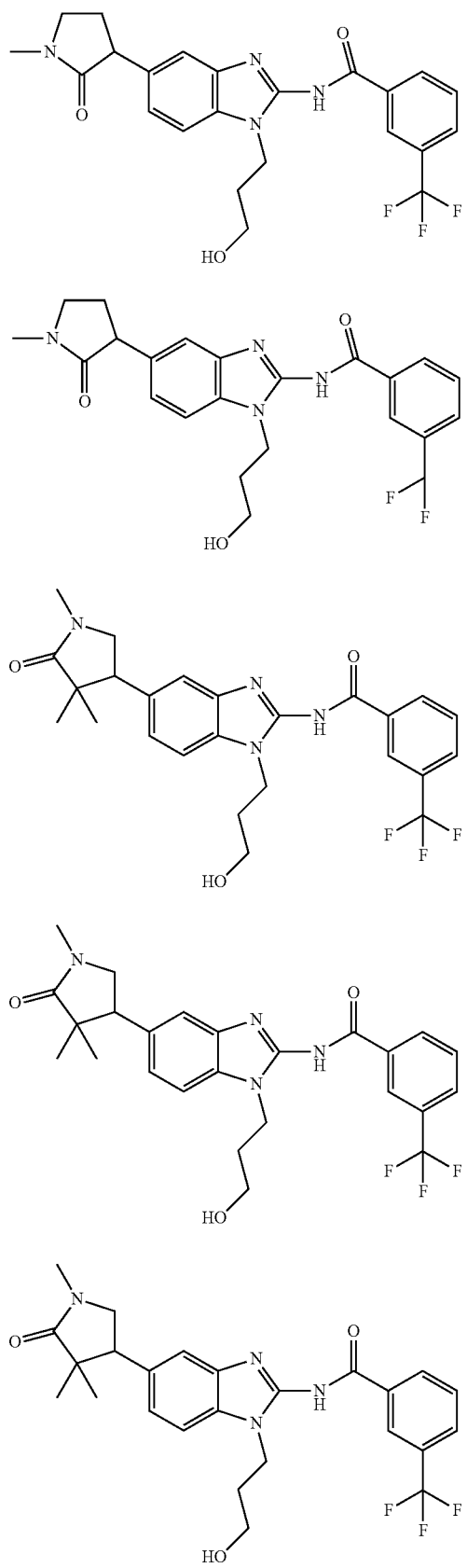
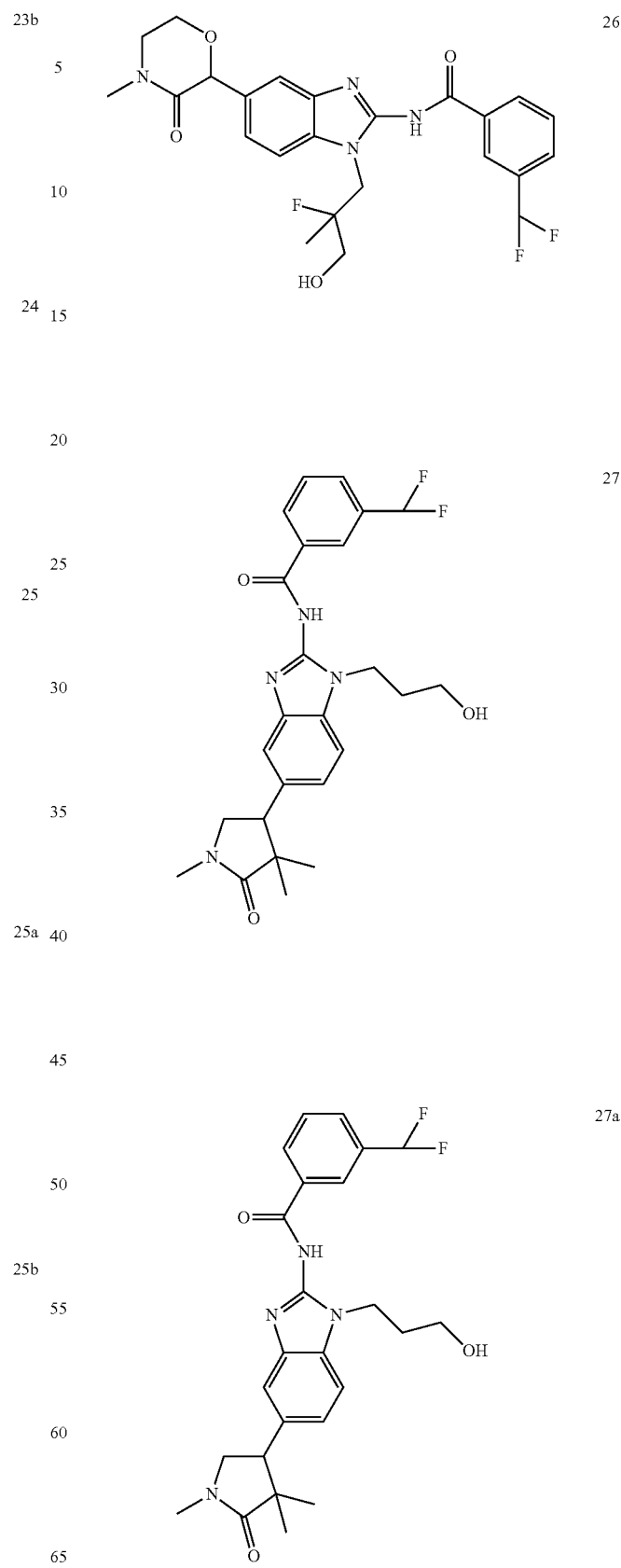

TABLE 1-continued
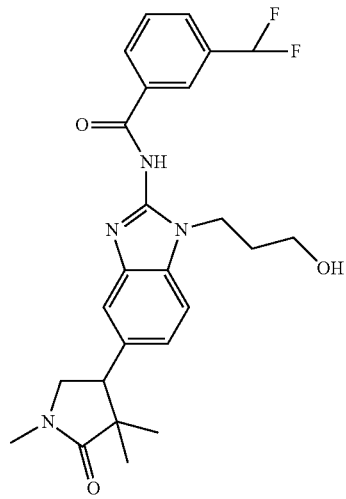 [SMILES: CN1CC(c2ccc3c(c2)nc(NC(=O)c2cccc(C(F)F)c2)n3CCCO)C(C)(C)C1=O]
27b
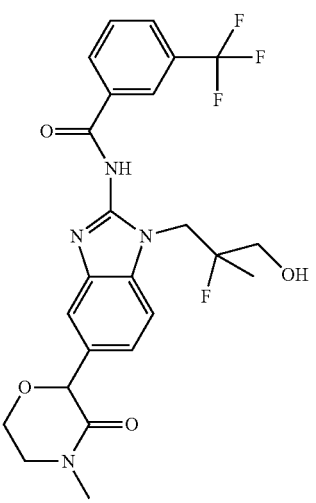 [SMILES: CN1CCOC(c2ccc3c(c2)nc(NC(=O)c2cccc(C(F)(F)F)c2)n3CC(C)(F)CO)C1=O]
28
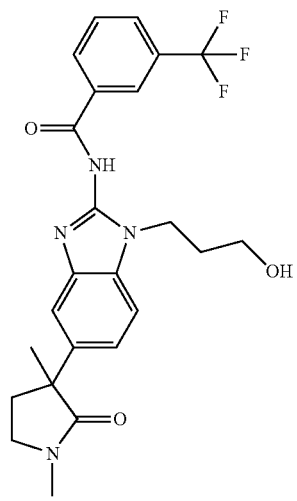 [SMILES: CN1CCC(C)(c2ccc3c(c2)nc(NC(=O)c2cccc(C(F)(F)F)c2)n3CCCO)C1=O]
29
TABLE 1-continued
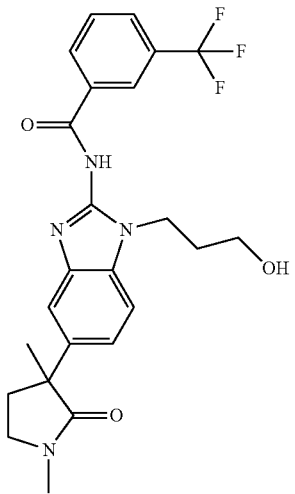 [SMILES: CN1CCC(C)(c2ccc3c(c2)nc(NC(=O)c2cccc(C(F)(F)F)c2)n3CCCO)C1=O]
29a
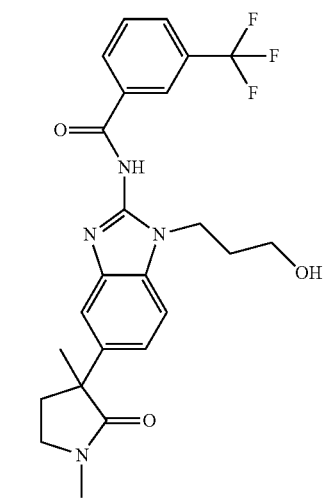 [SMILES: CN1CCC(C)(c2ccc3c(c2)nc(NC(=O)c2cccc(C(F)(F)F)c2)n3CCCO)C1=O]
29b
30

TABLE 1-continued
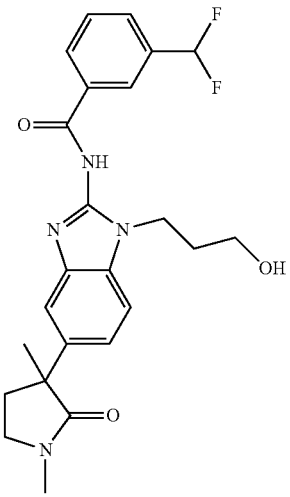 [SMILES: CN1CCC(C)(c2ccc3c(c2)nc(NC(=O)c2cccc(C(F)F)c2)n3CCCO)C1=O] 30a
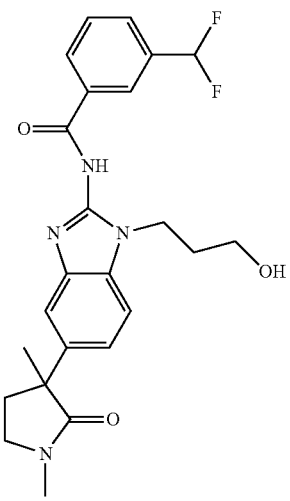 [SMILES: CN1CCC(C)(c2ccc3c(c2)nc(NC(=O)c2cccc(C(F)F)c2)n3CCCO)C1=O] 30b
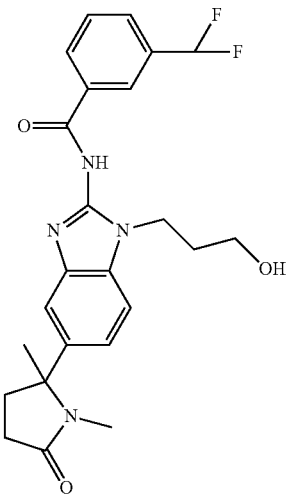 [SMILES: CN1C(=O)CCC1(C)c1ccc2c(c1)nc(NC(=O)c1cccc(C(F)F)c1)n2CCCO] 31
TABLE 1-continued
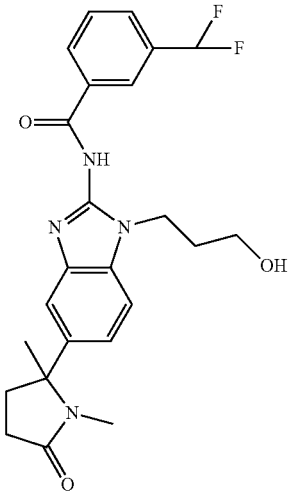 [SMILES: CN1C(=O)CCC1(C)c1ccc2c(c1)nc(NC(=O)c1cccc(C(F)F)c1)n2CCCO] 31a
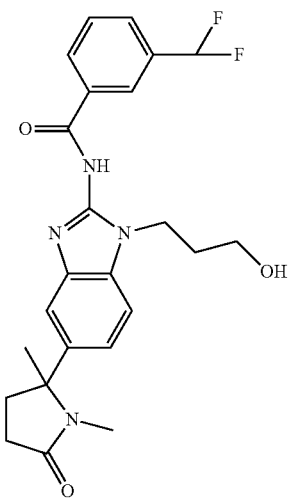 [SMILES: CN1C(=O)CCC1(C)c1ccc2c(c1)nc(NC(=O)c1cccc(C(F)F)c1)n2CCCO] 31b
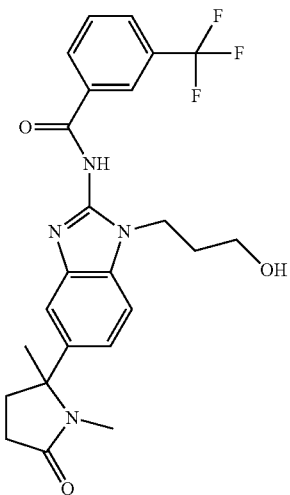 [SMILES: CN1C(=O)CCC1(C)c1ccc2c(c1)nc(NC(=O)c1cccc(C(F)(F)F)c1)n2CCCO] 32

TABLE 1-continued

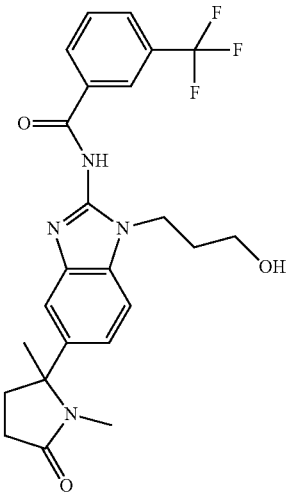 [SMILES: CN1C(=O)CCC1(C)c1ccc2c(c1)nc(NC(=O)c1cccc(C(F)(F)F)c1)n2CCCO]

32a

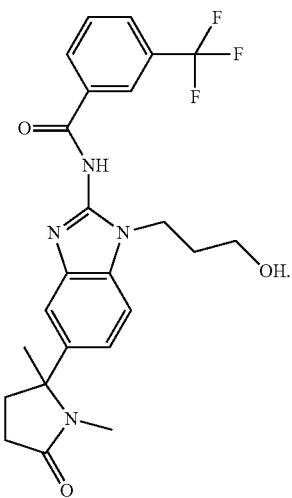 [SMILES: CN1C(=O)CCC1(C)c1ccc2c(c1)nc(NC(=O)c1cccc(C(F)(F)F)c1)n2CCCO]

32b

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

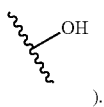

).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit IRAK, or a mutant thereof, in a biological sample or in a patient. In certain embodiments, the amount of compound in compositions of this invention is such that is effective to measurably inhibit IRAK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from an IRAK related disorder, comprising administering to said subject an effective amount of a compound of formula I and related formulae.

The present invention preferably relates to a method, wherein the IRAK associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality.

The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

The present invention furthermore relates to a method wherein the immunoregulatory abnormality is bone marrow or organ transplant rejection or graft-versus-host disease.

The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

In certain embodiments, disorders associated with IRAK are selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

In certain embodiments, the cancer is selected from carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

In certain embodiments, the cancer is brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. In some embodiments, the cancer is metastatic cancer. In some embodiments, the cancer is colorectal cancer. In some embodiments, the cancer is colon cancer.

In various embodiments, compounds of formula (I), and related formulae exhibit a IC50 for the binding to IRAK of less than about 5 µM, preferably less than about 1 µM and even more preferably less than about 0.100 µM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit IRAK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing IRAK-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of IRAK activity if expedient.

The invention also relates to the use of compounds according to formula (I) and/or physiologically acceptable salts thereof for the prophylactic or therapeutic treatment and/or monitoring of diseases that are caused, mediated and/or propagated by IRAK activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by IRAK activity. In certain embodiments, the invention provides the use of a compound according to formula I or physiologically acceptable salts thereof, for the production of a medicament for the prophylactic or therapeutic treatment of an IRAK-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with IRAK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with IRAK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

The disclosed compounds of the formula I can be administered in combination with other known therapeutic agents, including anticancer agents. As used here, the term "anti-cancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzuma[1,2,3], onartuzumab[1,3], racotumomab, tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane 1123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1]Prop. INN (Proposed International Nonproprietary Name); [2]Rec. INN (Recommended International Nonproprietary Names); [3]USAN (United States Adopted Name); [4]no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting IRAK activity in a biological sample comprising the step of contacting said biological sample with a compound of this invention, or a composition comprising said compound.

According to another embodiment, the invention relates to a method of inhibiting IRAK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of IRAK, including the evaluation of the many factors thought to influence, and be influenced by, the production of IRAK and the interaction of IRAK. The present compounds are also useful in the development of other compounds that interact with IRAK since the present compounds provide important structure-activity relationship (SAR) information that facilitate that development. Compounds of the present invention that bind to IRAK can be used as reagents for detecting IRAK in living cells, fixed cells, in biological fluids, in tissue homogenates, in purified, natural biological materials, etc. For example, by labeling such compounds, one can identify cells expressing IRAK. In addition, based on their ability to bind IRAK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing IRAK inside permeabilized cells. The compounds of the invention can also be utilized as commercial research reagents for various medical research and diagnostic uses. Such uses can include but are not limited to: use as a calibration standard for quantifying the activities of candidate IRAK inhibitors in a variety of functional assays; use as blocking reagents in random compound screening, i.e. in looking for new families of IRAK ligands, the compounds can be used to block recovery of the presently claimed IRAK compounds; use in the co-crystallization with IRAK enzyme, i.e. the compounds of the present invention will allow formation of crystals of the compound bound to IRAK, enabling the determination of enzyme/compound structure by x-ray crystallography; other research and diagnostic applications, wherein IRAK is preferably activated or such activation is conveniently calibrated against a known quantity of an IRAK inhibitor, etc.; use in assays as probes for determining the expression of IRAK in cells; and developing assays for detecting compounds which bind to the same site as the IRAK binding ligands.

The compounds of the invention can be applied either themselves and/or in combination with physical measurements for diagnostics of treatment effectiveness. Pharmaceutical compositions containing said compounds and the use of said compounds to treat IRAK-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of IRAK, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All reactions were conducted at room temperature unless otherwise noted. All compounds of the present invention were synthesized by processes developed by the inventors.

$^1$H-NMR spectra were acquired on a Bruker Fourier-300 MHz instrument. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), qt (quintuplet) or br (broad).

Mass spectra were obtained on Shimadzu LC-MS-2020 Series mass spectrometers, using Electrospray Ionization (ESI). Column: Luna C18, 5 μm, 2.0×50 mm; Solvent A: water+0.1% formic acid; Solvent B: MeCN+0.1% formic acid; Flow: 0.7 ml/min; Gradient: 0 min: 5% B, 5 min: 100% B, 6.5 min: 100% B, 6.51 min: 5% B, 7 min 5% B.

Compound numbers utilized in the Examples below correspond to compound numbers set forth supra.

The following abbreviations refer to the abbreviations used below:

Ac (acetyl), BINAP (2,2'-bis(disphenylphosphino)-1,1'-binaphthalene), dba (dibenzylidene acetone), Bu (Butyl), $^t$Bu (tert-Butyl), DCE (dichloroethane), DCM (Dichloromethane), δ (chemical shift), DIEA (di-isopropyl ethylamine), DMA (dimethyl acetamide), DMSO (Dimethyl Sulfoxide), DMF (N,N-Dimethylformamide), Dppf (1,1'-bis (diphenyl phosphine ferrocene)), EtOAc (Ethyl acetate), EtOH (Ethanol), eq (equivalent), g (gram), Hex (Hexane), $^c$Hex (Cyclohexane), HATU (N-[(Dimethylamino)(3H-[1,2,3] triazolo[4,5-b]pyridin-3-yloxy)methylene]-N-methylmethanaminiumhexafluoro phosphate), HPLC (High Performance Liquid Chromatography), h (hour), LDA (lithium diisopropyl amine), LiHMDS (lithium bis(trimethylsilyl)amide), MHz (Megahertz), MeOH (Methanol), min (minute), mL (milliliter), mmol (millimole), mM (millimolar), MS (Mass Spectrometry), NMR (Nuclear Magnetic Resonance), O/N (overnight), PBS (Phosphate Buffered Saline), RT (room temperature), TEA (Triethyl amine), TFA (Trifluoroacetic acid), THF (Tetrahydrofuran), TLC (Thin Layer Chromatography).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Intermediate Acid 1

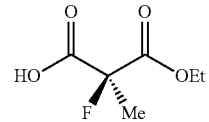 [SMILES: CCOC(=O)[C@@](C)(F)C(=O)O]

Step 1: diethyl 2-fluoro-2-methylmalonate

To a THF (0.5 M) solution of diethyl methylmalonate (1 eq.) was added sodium hydride (1.4 eq., 60% (w/w) dispersion in paraffin oil) in four equal portions, three to five minutes apart. The reaction was maintained at 0° C. for 15 min, before it was allowed to warm to RT over 30 min. After another 30 min of stirring at RT, the mixture was re-cooled to 0° C. and then added N-fluorobenzenesulfonamide (1.1 eq.) in four equal portions. Stirring was continued at 0° C. for 30 min and then at RT for 4 h, at which time it was determined to be >95% complete by $^1$H NMR. The reaction was then diluted with hexanes and vacuum filtered. The filter cake was washed further with hexanes and the product-containing filtrate was concentrated. More hexanes were added to induce further precipitation of the unwanted-by-products and the resulting suspension was filtered again. The filtrate thus obtained was then concentrated in vacuo to furnish a biphasic oil. The upper layer was determined to be paraffin oil and was discarded. The lower layer was the desired product (82% yield).

Step 2: (S)-3-ethoxy-2-fluoro-2-methyl-3-oxopropanoic acid

Diethyl 2-fluoro-2-methylmalonate (1 eq.) from the previous step was taken up in an aqueous pH=7.3 phosphate buffer (0.14 M, prepared by dissolving 7.3 g of NaHPO$_4$ and 2.1 g of KH$_2$PO$_4$ per L of water). Lipase from *Candida Rugosa* (70 mg per mmol of substrate, 847 U/mg, Sigma Cat#L1754) was then added and the resulting heterogeneous mixture was vigorously stirred at RT for 18 h. Depending on scale, occasional addition of 1 N NaOH was necessary to maintain the pH of the reaction mixture at ~7.3 to ensure optimal activity. The reaction mixture was then added celite, stirred at RT for 1 h and filtered. The filtrate was extracted with EtOAc, dried over MgSO$_4$, and filtered. Concentration of the filtrate in vacuo furnished the desired product as a white, crystalline solid (71% yield, 93% enantiomeric excess).

Intermediate Acid 2

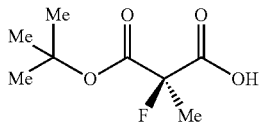 [SMILES: CC(C)(C)OC(=O)[C@](C)(F)C(=O)O]

Step 1: (R)-1-tert-butyl 3-ethyl 2-fluoro-2-methylmalonate

Intermediate acid 1 (1 eq.) was dissolved in thionyl chloride (2.3 M) at RT. To this was then added a few drops of neat DMF and the resulting mixture was heated at 75° C. for 2 h. The volatiles were then removed in vacuo and the intermediate acid chloride was taken up in dichloromethane (0.12 M). At 0° C., N,N-diisopropylethylamine (3 eq.) and tert-butanol (1.5 eq.) were then added sequentially to the above dichloromethane solution, and the resulting reaction mixture was allowed to warm slowly to RT over 16 h. The reaction was then carefully quenched with the addition of 1 N aq. HCl and extracted with dichloromethane. The combined organic extracts were washed further with sat. aq. NaHCO$_3$, water and brine, dried over MgSO$_4$ and filtered. Concentration of the filtrate in vacuo furnished the desired product as a colorless oil (65% yield).

Step 2: (R)-3-(tert-butoxy)-2-fluoro-2-methyl-3-oxopropanoic acid

To a THF solution (0.16 M) of (R)-1-tert-butyl 3-ethyl 2-fluoro-2-methylmalonate (1 eq.) from the previous step was added 1 N aq. NaOH (2 eq.). The resulting biphasic mixture was vigorously stirred at RT for 2 h. The reaction was then carefully quenched with the addition of 1 N aq. HCl (until pH of ~4) and extracted with EtOAc. The combined organic extracts were washed further with water and brine, dried over MgSO$_4$ and filtered. Concentration of the filtrate in vacuo furnished the desired product as a white solid (52% yield).

Intermediate Amine 1:

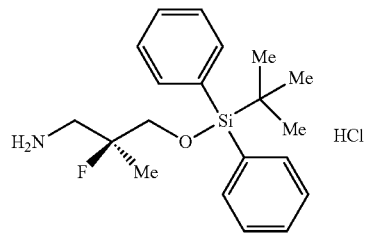 [SMILES: CC(C)(C)[Si](OC[C@@](C)(F)CN)(c1ccccc1)c1ccccc1 ; Cl]

Step 1: (S)-ethyl 2-fluoro-3-((4-methoxybenzyl)amino)-2-methyl-3-oxopropanoate

Intermediate acid 1 (1 eq.), 4-methoxybenzyl amine hydrochloride (1.1 eq.) and N,N-diisopropylethylamine (3.5 eq.) were combined in dichloromethane (0.15 M). To this was then added HATU (1.05 eq.) and the resulting mixture was stirred at RT for 18 h. The reaction was then quenched with the addition of 1 N aq. HCl and extracted with dichloromethane. The combined organic extracts were washed further with water, 10% aq. NaHCO$_3$ and brine, dried over MgSO$_4$, filtered and the filtrate concentrated in vacuo. Further purification of the crude product thus obtained by way of column chromatography (SiO$_2$, gradient elution, Hex→7:3 (v/v) Hex:EtOAc) furnished the desired product as a golden yellow oil (70% yield).

Step 2: (R)-2-fluoro-3-hydroxy-N-(4-methoxybenzyl)-2-methylpropanamide

To a methanol (0.23 M) solution of (S)-ethyl 2-fluoro-3-((4-methoxybenzyl)amino)-2-methyl-3-oxopropanoate (1 eq.) from the previous step was added at 0° C. calcium iodide (1 eq.) and sodium borohydride (2 eq.). Following an initial vigorous evolution of gas, the cooling bath was removed and the reaction mixture was allowed to stir at RT for 4 h. The reaction was then quenched with the addition of 10% aq. HCl and extracted with EtOAc. The combined organic extracts were washed further with water, 1 N aq. NaOH and brine, dried over MgSO$_4$, filtered and the filtrate concentrated in vacuo. Recrystallization of the crude product thus obtained from dichloromethane, ether and hexanes furnished the desired product as a white crystalline solid (86% yield).

Step 3: (R)-2-fluoro-N-(4-methoxybenzyl)-2-methyl-3-((triisopropylsilyl)oxy)-propanamide To a dichloromethane (0.31 M) solution of (R)-2-fluoro-3-hydroxy-N-(4-methoxybenzyl)-2-methylpropanamide (1 eq.) from the previous step was added at 0° C. 2,6-lutidine (1.5 eq.) and then triisopropylsilyl trifluoromethanesulfonate (1.2 eq.). The resulting solution was allowed to stir at 0° C. for 10 min and then at RT for 30 min. The reaction was then carefully quenched with the addition of 0.1 N aq. HCl and extracted with dichloromethane. The combined organic extracts were washed further with water and brine, dried over MgSO$_4$ and filtered. Concentration of the filtrate in vacuo furnished the desired product as a colorless oil (71% yield).

Step 4: (S)-2-fluoro-N-(4-methoxybenzyl)-2-methyl-3-((triisopropylsilyl)oxy)propan-1-amine To a THF (0.25 M) solution of (R)-2-fluoro-N-(4-methoxybenzyl)-2-methyl-3-((triisopropylsilyl)oxy)-propanamide (1 eq.) from the previous step was added at RT borane (6 eq., 1 M solution in THF) drop-wise over a period of 30 min. Following the completion of addition, a reflux condenser was attached and the reaction mixture was heated at reflux for 18 h. With the reaction deemed complete, the reaction was quenched slowly and carefully at 0° C. with the drop-wise addition of methanol. The volatiles were then removed in vacuo and the resulting residue was co-evaporated with toluene (3×). The crude product thus obtained was used immediately in the next step.

Step 5: (S)-tert-butyl (2-fluoro-2-methyl-3-((triisopropylsilyl)oxy)propyl)(4-methoxybenzyl)carbamate To a dichloromethane (0.29 M) solution of (S)-2-fluoro-N-(4-methoxybenzyl)-2-methyl-3-((triisopropylsilyl)oxy) propan-1-amine (1 eq.) from the previous step was added N,N-diisopropylethylamine (3 eq.) and then di-tert-butyl dicarbonate (1.5 eq.). The resulting solution was allowed to stir at RT for 5 h. The reaction was then carefully quenched with the addition of 1 N aq. HCl and extracted with dichloromethane. The combined organic extracts were washed further with water and brine, dried over MgSO₄ and filtered. Concentration of the filtrate in vacuo furnished the desired product as a colorless oil (62% yield over two steps).

Step 6: (S)-tert-butyl (2-fluoro-3-hydroxy-2-methylpropyl)carbamate

To a 3:1 (v/v) acetonitrile: water (0.1 M) solution of (S)-tert-butyl (2-fluoro-2-methyl-3-((triisopropylsilyl)-oxy)propyl)(4-methoxybenzyl)carbamate (1 eq.) from the previous step was added ammonium cerium nitrate (2 eq.) and the resulting mixture was stirred at RT for 18 h. The reaction solution was then diluted with water and extracted with EtOAc. The combined organic extracts were washed further with water and brine, dried over MgSO₄, filtered and the filtrate concentrated in vacuo. Further purification of the crude product thus obtained by way of column chromatography (SiO₂, gradient elution, Hex→EtOAc) furnished the desired product as a white crystalline solid (70% yield).

Step 7: (S)-tert-butyl (3-((tert-butyldiphenylsilyl)oxy)-2-fluoro-2-methylpropyl)carbamate To a dichloromethane (0.1 M) solution of (S)-tert-butyl (2-fluoro-3-hydroxy-2-methylpropyl)carbamate (1 eq.) from the previous step was added sequentially N,N-diisopropylethylamine (2.5 eq.), DMAP (0.05 eq.) and tert-butyldiphenylchlorosilane (1.3 eq.). The resulting solution was allowed to stir at RT for 72 h. The reaction was then carefully quenched with the addition of 1 N aq. HCl and extracted with dichloromethane. The combined organic extracts were washed further with water and brine, dried over MgSO₄, filtered and the filtrate concentrated in vacuo. Further purification of the crude product thus obtained by way of column chromatography (SiO₂, gradient elution, Hex→1:1 (v/v) Hex:EtOAc) furnished the desired product as a colorless oil (88% yield).

Step 8: (S)-3-((tert-butyldiphenylsilyl)oxy)-2-fluoro-2-methylpropan-1-amine hydrochloride To a dichloromethane (0.1 M) solution of (S)-tert-butyl (3-((tert-butyldiphenylsilyl)oxy)-2-fluoro-2-methylpropyl) carbamate (1 eq.) from the previous step was added HCl (5 eq., 4 M solution in 1,4-dioxane) and the resulting solution was stirred at RT for 2 h. The volatiles were then removed in vacuo and the resulting residue was re-crystallized from ether and hexanes. The title compound was isolated as a white crystalline solid (86% yield).

Intermediate Amine 2:

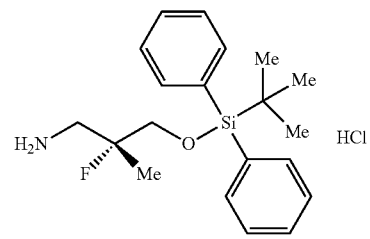 [SMILES: CC(C)(C)[Si](OC[C@](C)(F)CN)(c1ccccc1)c1ccccc1 ; Cl]

Prepared in an analogous fashion to Intermediate amine 1, but using Intermediate acid 2 (1 eq.) in place of Intermediate acid 1 in step 1.

Intermediate Amine 3:

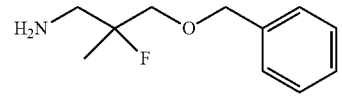

Step 1: 1-azido-3-(benzyloxy)-2-methylpropan-2-ol

A solution of 2-[(benzyloxy)methyl]-2-methyloxirane (Matrix Scientifics, 4.1 g, 20.7 mmol, 1.00 equiv), NH₄Cl (2.3 g, 42.14 mmol, 2.04 equiv) and NaN₃ (4.2 g, 63.31 mmol, 3.06 equiv, 98%) in DMF (30 mL) was stirred for 16 h at 60° C. The reaction mixture was diluted with water (300 mL) and extracted with DCM (3×50 mL). Combined organic phases were dried over sodium sulfate, filtered and concentrated. Purification by flash chromatography on silica (petroleum ether:EtOAc, gradient from 50:1 to 20:1) afforded the title compound as a yellow oil (4 g, 69%).

Step 2: [(3-azido-2-fluoro-2-methylpropoxy)methyl]benzene

DAST (5.3 g, 32.22 mmol, 1.12 equiv, 98%) was added dropwise to a solution of 1-azido-3-(benzyloxy)-2-methylpropan-2-ol (7.1 g, 28.9 mmol, 1.00 equiv) in DCM (100 mL) maintained under nitrogen atmosphere an at ° C. The reaction mixture was allowed to warm to RT and stirred for 4 h. It was then quenched with water (30 mL) and extracted with DCM (3×30 mL). Combined organic phases were concentrated under reduced pressure and purified by flash chromatography on silica (petroleum ether:EtOAc, gradient from 15:1 to 10:1) to afford the title compound as a yellow oil (6 g, 84%).

Step 3: 3-(benzyloxy)-2-fluoro-2-methylpropan-1-amine

Triphenylphosphane (3.76 g, 13.62 mmol, 1.30 equiv) was added slowly to a solution of [(3-azido-2-fluoro-2- methylpropoxy)methyl]benzene (2.60 g, 10.48 mmol, 1.00 equiv) in THF (40 mL) and water (10 mL) previously purged with nitrogen and maintained under nitrogen and at ° C. The reaction mixture was then allowed to warm to RT and stirred O/N before being concentrated under vacuum. The resulting residue was triturated in Ether and the solids were filtered out. The filtrate was concentrated and purified by flash chromatography on silica (DCM:MeOH, 20:1) to afford the title compound as a yellow solid (2 g, 67%).

Intermediate 1-CF$_3$

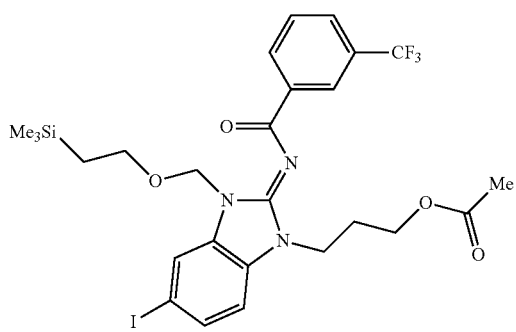 [SMILES: CC(=O)OCCCn1/c(=N/C(=O)c2cccc(C(F)(F)F)c2)n(COCC[Si](C)(C)C)c2cc(I)ccc21]

Step 1: 3-(4-iodo-2-nitro-phenylamino)-propan-1-ol

In a glass RBF equipped with a Teflon-coated magnetic stirrer was dissolved 1-fluoro-4-iodo-2-nitro-benzene (1 eq.) in DMF (0.3 M). To this was then added 3-amino-propan-1-ol (1.2 eq.) and potassium carbonate (3 eq.). The resulting solution was heated at 65° C. for 18 h. The crude reaction mixture was then diluted with EtOAc and washed sequentially with water and brine. The organic extract was then dried over MgSO$_4$, filtered and the filtrate concentrated in vacuo. Purification of the crude product thus obtained by way of column chromatography (SiO$_2$, gradient elution, 8:1 (v/v) Hex:EtOAc→EtOAc) furnished the desired product (79% yield).

Step 2: 3-((4-iodo-2-nitrophenyl)amino)propyl acetate

In a glass RBF equipped with a Teflon-coated magnetic stirrer was dissolved 3-(4-iodo-2-nitro-phenylamino)-propan-1-ol (1 eq.) from the previous step in pyridine (0.1 M). To this was then added acetic anhydride (1.8 eq.) drop-wise and neat over 10 min. After 18 h of stirring at RT, the volatiles were removed in vacuo and the resulting residue was partitioned between EtOAc and sat. aq. NH$_4$Cl. The aqueous layer was separated and back-extracted with EtOAc. The combined organic extracts were then dried over MgSO$_4$, filtered and the filtrate concentrated in vacuo. Purification of the crude product thus obtained by way of column chromatography (SiO$_2$, gradient elution, 8:1 (v/v) Hex:EtOAc→EtOAc) furnished the desired product (91% yield).

Step 3: 3-((2-amino-4-iodophenyl)amino)propyl acetate

In a glass RBF equipped with a Teflon-coated magnetic stirrer was suspended iron trichloride (0.25 eq.), activated charcoal (100 mg per mmol of substrate), and 3-((4-iodo-2-nitrophenyl)amino)propyl acetate (1 eq.) from the previous step in methanol (0.15 M). To this was then added N,N-dimethyl hydrazine (5 eq.) drop-wise and neat over a period of 10 min. The resulting suspension was then heated at 65° C. for 4 h. The insolubles were removed via filtration through a bed of MeOH-wetted celite and the filtrate thus obtained was then concentrated in vacuo. The resulting residue was taken up in EtOAc, washed sequentially with water and brine, dried over MgSO$_4$, filtered and the filtrate concentrated in vacuo. Purification of the crude product thus obtained by way of column chromatography (SiO$_2$, gradient elution, 1:1 (v/v) Hex:EtOAc→EtOAc) furnished the desired product (89% yield).

Step 4: 3-(2-amino-5-iodo-1H-benzo[d]imidazol-1-yl)propyl acetate

In a glass RBF equipped with a Teflon-coated magnetic stirrer was added cyanogen bromide (2 eq., 5 M solution in acetonitrile) slowly to ethanol (0.5 M) over a period of 10 min. To this solution was then added an ethanol (0.25 M) solution of 3-((2-amino-4-iodophenyl)amino)propyl acetate (1 eq.) from the previous step drop-wise over a period of 10 min. The resulting mixture was allowed to stir at RT for 3 h. The volatiles were then removed in vacuo and the resulting residue was taken up in EtOAc and washed sequentially with 10% aq. NaHCO$_3$, water and brine. The organic extract thus obtained was then dried over Na$_2$SO$_4$, filtered and the filtrate concentrated in vacuo. Purification of the crude product thus obtained by way of column chromatography (SiO$_2$, gradient elution, 1:1 (v/v) Hex:EtOAc→EtOAc→10:1 (v/v) EtOAc:MeOH) furnished the desired product (81% yield).

Step 5: (E)-3-(5-iodo-2-((3-(trifluoromethyl)benzoyl)imino)-2,3-dihydro-1H-benzo[d]imidazol-1-yl)propyl acetate In a glass RBF equipped with a Teflon-coated magnetic stirrer was dissolved 3-(2-amino-5-iodo-1H-benzo[d]imidazol-1-yl)propyl acetate (1 eq.) from the previous step, 3-trifluoromethyl-benzoic acid (1 eq.) and HATU (1.2 eq.) in DMF (0.1 M). To this was then added ethyl-diisopropyl-amine (2.5 eq.) and the resulting yellow solution was allowed to stir at RT for 14 h. The crude reaction mixture was diluted with EtOAc and washed sequentially with water, 10% aq. HCl, water and brine. The organic extract was then dried over MgSO$_4$, filtered and the filtrate concentrated in vacuo. Further purification by way of column chromatography (SiO$_2$, gradient elution, 9:1 (v/v) Hex:EtOAc→EtOAc) furnished the desired product as an off-white solid (77% yield).

Step 6: (Z)-3-(5-iodo-2-((3-(trifluoromethyl)benzoyl)imino)-3-((2-(trimethylsilyl)ethoxy)methyl)-2,3-dihydro-1H-benzo[d]imidazol-1-yl)propyl acetate In a glass RBF equipped with a Teflon-coated magnetic stirrer was suspended sodium hydride (1.6 eq., 60% (w/w) dispersion in paraffin oil) in DMF (0.09 M). To this was then added, at 0° C., (E)-3-(5-iodo-2-((3-(trifluoromethyl)benzoyl)imino)-2,3-dihydro-1H-benzo[d]imidazol-1-yl)propyl acetate (1 eq.) from the previous step. The resulting suspension was then stirred at 0° C. for 30 min before (2-(chloromethoxy)ethyl)trimethylsilane (2 eq.) was added dropwise and neat over a period of 5 min. After another 1 h of stirring at 0° C., the reaction then quenched with the addition of water and extracted with EtOAc. The combined organic extracts were washed further with water and brine, dried over MgSO$_4$, filtered and the filtrate concentrated in vacuo. Further purification by way of column chromatography (SiO$_2$, gradient elution, 9:1 (v/v) Hex:Acteone→Acetone) furnished the desired product as a viscous oil (78% yield).

Intermediate 2

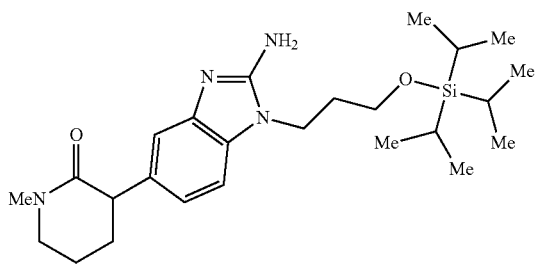 [SMILES: CC(C)[Si](OCCCn1c(N)nc2cc(C3CCCN(C)C3=O)ccc21)(C(C)C)C(C)C]

Step 1:
3-(4-fluoro-3-nitro-phenyl)-2-methoxypyridine

In a glass reaction vessel equipped with a Teflon-coated screw cap was combined (4-fluoro-3-nitro-phenyl)boronic acid (1.5 eq.), palladium(II) acetate (0.05 eq.), dicyclohexyl-(2'6'-dimethoxy-biphenyl-2-yl)-phosphine (0.1 eq.) and potassium fluoride (3 eq.) in THF (0.11 M). The reaction suspension was then sub-surface purged with nitrogen for 15 min before 3-bromo-2-methoxy-pyridine (1 eq.) was added. The reaction vessel was then tightly sealed and heated at 70° C. for 16 h. The resulting brown reaction suspension was diluted with tBuOMe and washed sequentially with 10% aq. NaHCO$_3$, water and brine. The organic extract was then dried over MgSO$_4$, filtered and the filtrate concentrated in vacuo to furnish a dark brown solid. Purification of the crude product thus obtained by way of column chromatography (SiO$_2$, gradient elution, Hex→3:7 (v/v) Hex:EtOAc) furnished the desired product as a white solid (98% yield).

Step 2: 3-(4-fluoro-3-nitro-phenyl)-pyridin-2-ol

In a glass reaction vessel equipped with a Teflon-coated screw cap was dissolved 3-(4-fluoro-3-nitro-phenyl)-2-methoxypyridine (1 eq.) from the previous step in glacial acetic acid (0.078 M). To this was then added hydrogen bromide (3 eq., 48% (w/v) aqueous solution) and the resulting mixture was heated at 70° C. for 16 h. The now yellow solution was cooled to RT and the volatiles were then removed in vacuo. The resulting semi-solid was then triturated in dichloromethane and ether for 2 h. The desired product was then isolated via vacuum filtration as a crystalline white solid (98% yield).

Step 3: 3-(4-fluoro-3-nitrophenyl)-1-methylpyridin-2(1H)-one

In a glass reaction vessel equipped with a Teflon-coated magnetic stirrer was suspended 3-(4-fluoro-3-nitro-phenyl)-pyridin-2-ol (1 eq.) from the previous step, cesium carbonate (1.5 eq.) and iodomethane (3 eq.) in DMF (0.12 M). The resulting mixture was then allowed to stir at RT for 48 h. The reaction was quenched with the addition of 10% aq. HCl and extracted with EtOAc. The combined organic extracts were then washed further with water and brine, dried over MgSO$_4$, and filtered. Concentration of the filtrate in vacuo furnished the desired product, after further trituration in ether and hexanes, as a yellow crystalline solid (65% yield).

Step 4: 3-(4-((3-hydroxypropyl)amino)-3-nitrophenyl)-1-methylpyridine-2(1H)-one

In a glass RBF equipped with a Teflon-coated magnetic stirrer was dissolved 3-(4-fluoro-3-nitrophenyl)-1-methyl-pyridin-2(1H)-one (1 eq.) from the previous step in acetonitrile (0.1 M). To this was then added 3-aminopropan-1-ol (1.5 eq.) and cesium carbonate (2 eq.). The resulting suspension was heated at 80° C. for 16 h. The volatiles removed in vacuo and the resulting residue was partitioned between EtOAc and 10% aq. HCl. The organic extract was then separated and washed further with water and brine, dried over MgSO$_4$, filtered and the filtrate concentrated in vacuo. Further purification of the crude product thus obtained by way of column chromatography (SiO$_2$, gradient elution, 4:1 (v/v) Hex:EtOAc→EtOAc→10:1 (v/v) EtOAc:MeOH) furnished the desired product as an orange oil that solidified upon standing (85% yield).

Step 5: 1-methyl-3-(3-nitro-4-((3-((triisopropylsilyl)oxy)propyl)amino)phenyl)-pyridine-2(1H)-one In a glass RBF equipped with a Teflon-coated magnetic stirrer was dissolved 3-(4-((3-hydroxypropyl)amino)-3-nitrophenyl)-1-methylpyridine-2(1H)-one (1 eq.) from the previous step in DMF (0.11 M). To this was then added chloro-triisopropyl-silane (6 eq.), imidazole (6 eq.) and a few crystals of DMAP. The resulting solution was stirred at RT for 18 h. The crude reaction mixture was diluted with EtOAc and washed sequentially with water, 10% aq. NaHCO$_3$, water and brine. The organic extract was then dried over Na$_2$SO$_4$, filtered and the filtrate concentrated in vacuo. Further purification by way of column chromatography (SiO$_2$, gradient elution, 1:1 (v/v) Hex:EtOAc→EtOAc) furnished the desired product as an orange oil that solidified upon standing (61% yield).

Step 6: 3-(3-amino-4-((3-((triisopropylsilyl)oxy)propyl)amino)phenyl)-1-methylpiperidin-2-one In a Parr shaker flask was suspended 1-methyl-3-(3-nitro-4-((3-((triisopropylsilyl)oxy)propyl)amino)phenyl)-pyridine-2(1H)-one (1 eq.) from the previous step and palladium black (dry, 10% w/w over carbon, 0.4 eq.) in methanol (0.12 M). The vessel was then repeatedly evacuated and back-filled with nitrogen (3×) and then hydrogen (3×). The resulting suspension was shaken under 50 psi of hydrogen for 16 h. The reaction was then quenched with CH$_2$Cl$_2$ and filtered through a bed of CH$_2$Cl$_2$-wetted celite. The insoluble bed was washed further with MeOH and CH$_2$Cl$_2$. Concentration of the filtrate thus obtained in vacuo furnished a brown oil. Further purification of the crude product thus obtained by way of column chromatography (SiO$_2$, gradient elution, CH$_2$Cl$_2$→10:1 (v/v) CH$_2$Cl$_2$:MeOH) furnished the desired product as a tan solid that darkened upon standing (75% yield).

Step 7: 3-(2-amino-1-(3-((triisopropylsilyl)oxy)propyl)-1H-benzo[d]imidazol-5-yl)-1-methylpiperidin-2-one In a glass RBF equipped with a Teflon-coated magnetic stirrer was dissolved 3-(3-amino-4-((3-((triisopropylsilyl)

oxy)propyl)amino)phenyl)-1-methylpiperidin-2-one (1 eq.) from the previous step in ethanol (0.05 M). To this was then added cyanogen bromide (5 M solution in acetonitrile, 1.5 eq.) drop-wise over a period of 10 min. The resulting mixture was allowed to stir at RT for 12 h. The crude reaction mixture was diluted with EtOAc and washed sequentially with 10% aq. NaHCO₃, water and brine. The organic extract was then dried over Na₂SO₄ and filtered. Concentration of the filtrate thus obtained in vacuo furnished the desired product as an off-white solid (82% yield).

Intermediate 3

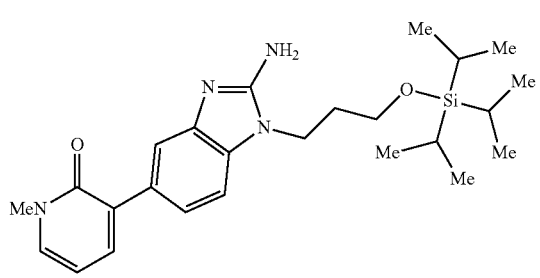 [SMILES: CC(C)[Si](OCCCn1c(N)nc2cc(-c3cccn(C)c3=O)ccc21)(C(C)C)C(C)C]

Prepared in an analogous fashion to Intermediate 2, but using iron trichloride (0.25 eq.), activated charcoal (100 mg per mmol of substrate), and N,N-dimethyl hydrazine (5 eq.) in place of palladium black and hydrogen gas in step 6.

Intermediate 4

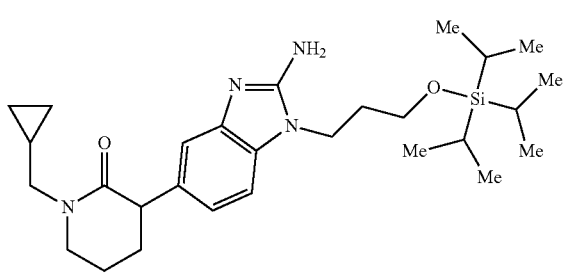 [SMILES: CC(C)[Si](OCCCn1c(N)nc2cc(C3CCCN(CC4CC4)C3=O)ccc21)(C(C)C)C(C)C]

Prepared in an analogous fashion to Intermediate 2, but using bromomethyl-cyclopropane (1.5 eq.) in place of iodomethane in step 3.

Intermediate 5

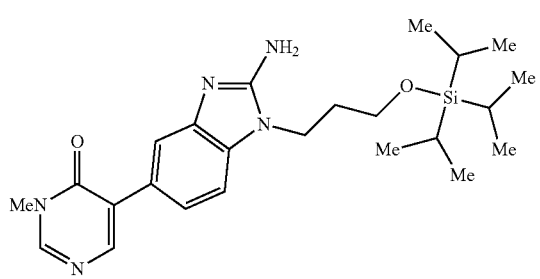 [SMILES: CC(C)[Si](OCCCn1c(N)nc2cc(-c3cncn(C)c3=O)ccc21)(C(C)C)C(C)C]

Prepared in an analogous fashion to Intermediate 2, but using 5-bromo-4-methoxy-pyrimidine (1 eq.) in place of 3-bromo-2-methoxy-pyridine in step 1. Furthermore, iron trichloride (0.25 eq.), activated charcoal (100 mg per mmol of substrate), and N,N-dimethyl hydrazine (5 eq.) were used in place of palladium black and hydrogen gas in step 6.

Intermediate 6

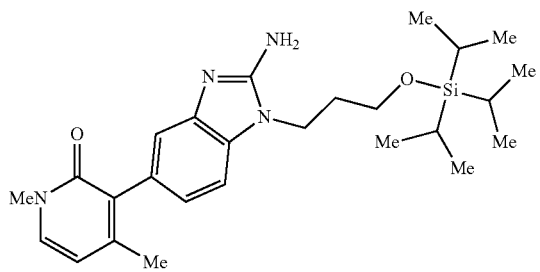 [SMILES: Cc1ccn(C)c(=O)c1-c1ccc2c(c1)nc(N)n2CCCO[Si](C(C)C)(C(C)C)C(C)C]

Prepared in an analogous fashion to Intermediate 2, but using 3-bromo-2-methoxy-4-methylpyridine (1 eq.) in place of 3-bromo-2-methoxy-pyridine in step 1. Furthermore, iron trichloride (0.25 eq.), activated charcoal (100 mg per mmol of substrate), and N,N-dimethyl hydrazine (5 eq.) were used in place of palladium black and hydrogen gas in step 6.

Intermediate 7

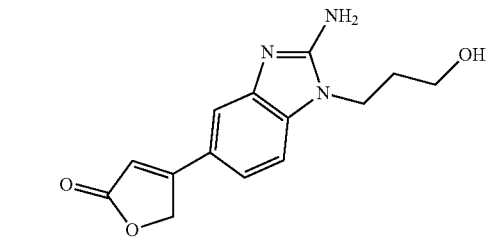 [SMILES: Nc1nc2cc(C3=CC(=O)OC3)ccc2n1CCCO]

Prepared in an analogous fashion to Intermediate 2, but using 4-bromo-5H-furan-2-one (1 eq.) in place of 3-bromo-2-methoxy-pyridine in step 1. Furthermore, step 2, step 3, and step 5 were omitted.

Intermediate 8-CF₃

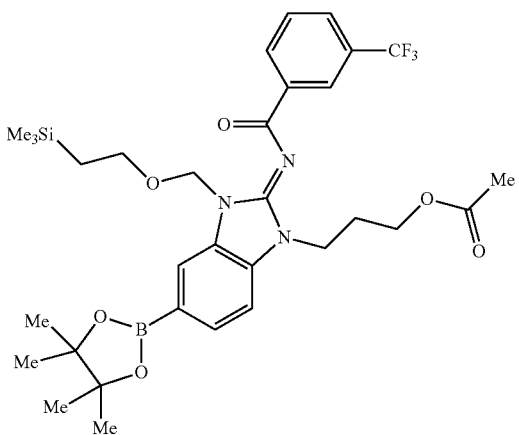 [SMILES: CC(=O)OCCCn1/c(=N/C(=O)c2cccc(C(F)(F)F)c2)n(COCC[Si](C)(C)C)c2cc(B3OC(C)(C)C(C)(C)O3)ccc21]

In a glass reaction vessel equipped with a Teflon-coated screw cap was suspended Intermediate 1-CF₃ (1 eq.), 4,4,4',4',5,5,5',5'-octamethyl-2,2'-bi(1,3,2-dioxaborolane) (1.5 eq.) and cesium carbonate (1.5 eq.) in acetonitrile (0.1 M). The reaction mixture was then thoroughly de-oxygenated via sub-surface purging with nitrogen for 30 min. Finally, palladium(II) acetate (0.1 eq.), triphenylphosphine (0.1 eq.) and copper iodide (0.4 eq.) were added in one rapid portion. The resulting mixture was then stirred at RT for 18 h. The crude reaction mixture was then diluted with EtOAc and washed sequentially with water and brine. The organic extract was then dried over MgSO₄, filtered and the filtrate concentrated in vacuo. Purification of the crude product thus obtained by way of column chromatography (SiO₂, gradient elution, Hex→2:3 (v/v) Hex:EtOAc) furnished the desired product as a viscous, yellow oil (91% yield).

Intermediate 9

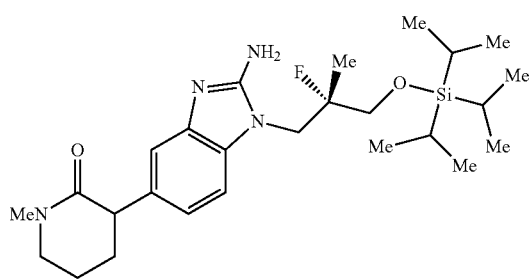 [SMILES: CC(C)[Si](OC[C@@](C)(F)Cn1c(N)nc2cc(C3CCCN(C)C3=O)ccc21)(C(C)C)C(C)C]

Prepared in an analogous fashion to Intermediate 2, but using Amine 1 (1.0 eq.) in place of 3-aminopropan-1-ol in step 4.

Intermediate 10

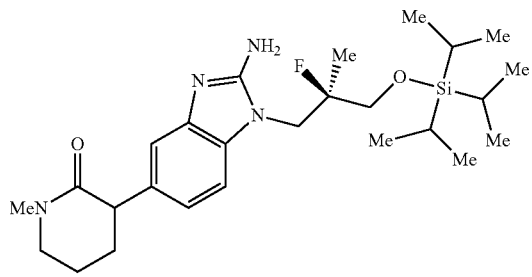 [SMILES: CC(C)[Si](OC[C@](C)(F)Cn1c(N)nc2cc(C3CCCN(C)C3=O)ccc21)(C(C)C)C(C)C]

Prepared in an analogous fashion to Intermediate 2, but using Amine 2 (1.0 eq.) in place of 3-aminopropan-1-ol in step 4.

Intermediate 11: 3-(2-Amino-1-but-3-enyl-1H-benzoimidazol-5-yl)-1-methyl-pyrrolidin-2-one hydrobromide

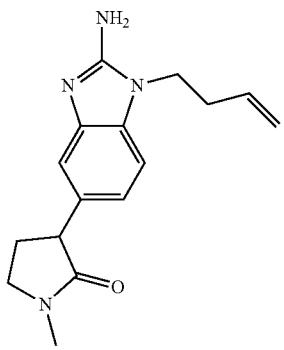 [SMILES: C=CCCn1c(N)nc2cc(C3CCN(C)C3=O)ccc21]

Step 1: 4-Fluorophenylacetic Acid Methyl Ester

To a solution of 4-fluorophenylacetic acid in MeOH (400 mL) at 0° C. was added drop-wise SOCl₂ (92 g, 773 mmol, 56 mL). The reaction was stirred at 60° C. under N₂ for 1 hr. TLC (EtOAc:petroleum ether, 1:1, starting material Rf=0.1, product Rf=0.9) showed the reaction was completed. The reaction mixture was concentrated under reduced pressure to remove MeOH and SOCl₂. The residue was diluted with saturated NaHCO₃ (300 mL) and extracted with EtOAc (2×300 mL). The combined organic phases were dried over Na₂SO₄, filtered and concentrated to afford the title compound (45 g, crude) as a colorless oil. ¹HNMR (400 MHz, CDCl₃,) δ 7.29-7.25 (m, 2H), 7.06-7.01 (m 2H), 3.72 (s, 3H), 3.62 (s, 2H).

Step 2: 3-Cyano-2-(4-fluorophenyl)-propionic acid methyl ester

To a solution of 4-fluorophenylacetic acid methyl ester (20 g, 119 mmol) in THF (300 mL) at −70 OC was added drop-wise LDA (2 M, 81 mL). After 1 hr stirring, a solution of 2-bromoacetonitrile (14.4 g, 120 mmol, 8 mL) in anhydrous THF (50 mL) was added and the reaction was stirred at −70° C. under N₂ for 1 hr. TLC (petroleum ether: EtOAc, 3:1, starting material Rf=0.7, product Rf=0.4) showed the reaction was completed. The reaction was quenched by sat. NH₄Cl and then extracted with EtOAc (2×300 mL). The combined organic phases were washed with brine (2×100 mL), dried over anhydrous Na₂SO₄, filtered and concentrated in vacuo. Purification by flash chromatography on silica (petroleum ether: EtOAc, gradient from 20:1 to 3:1) afforded the title compound (19 g, 77%) as a colorless oil. ¹HNMR (400 MHz, CDCl₃) δ 7.30-7.03 (m, 2H), 7.12-7.07 (m, 2H), 3.98-3.93 (m, 1H) 3.75 (s, 3H), 3.09-3.00 (m, 1H) 2.86-2.80 (m, 1H)

Step 3: 3-(4-Fluorophenyl)-pyrrolidin-2-one

To a solution of 3-Cyano-2-(4-fluorophenyl)-propionic acid methyl ester (7 g, 33.8 mmol), NH₃.H₂O (10.9 g, 312 mmol, 12 mL) in EtOH (120 mL) was added Raney-Ni (1.2 g) under nitrogen. The suspension was degassed under vacuum and purged with H₂ several times. The mixture was stirred under H₂ (50 psi) at 40° C. for 16 h. TLC (DCM: MeOH, 20:1, starting material Rf=0.9, product Rf=0.3)

showed the reaction was completed. The reaction mixture was filtered through a celite pad. The pad was rinsed with EtOH (3×20 mL) and the filtrate was concentrated under reduced pressure to afford the title compound (12 g, 49.6% yield) as a white solid. $^1$HNMR (400 MHz, DMSO-$d_6$) δ 7.82 (s, 1H), 7.30-7.26 (m, 2H), 7.16-7.12 (m, 2H) 3.55 (t, J=9.2 Hz, 1H), 3.32-3.27 (m, 2H), 2.49-2.46 (m, 1H), 2.09-2.02 (m, 1H)

Step 4: 3-(4-Fluorophenyl)-1-methylpyrrolidin-2-one

To a solution of 3-(4-Fluorophenyl)-pyrrolidin-2-one (10 g, 55.8 mmol), KOH (3.44 g, 61.4 mmol) and tetrabutylammonium bromide (1.6 g, 5.6 mmol) in THF (300 mL) at 0° C. was added drop-wise MeI (8.48 g, 59.8 mmol, 3.72 mL) in THF (20 mL). The reaction was stirred at 28° C. under $N_2$ for 3 hrs. TLC (petroleum ether, EtOAc, 1:1, starting material Rf=0.1, product Rf=0.2) showed the reaction was completed. The reaction mixture was concentrated under reduced pressure to remove THF. It was then diluted with water (200 mL) and extracted with EtOAc (2×400 mL). The combined organic phases were dried over $Na_2SO_4$, filtered and concentrated. Purification by flash chromatography on silica (petroleum ether:EtOAc, gradient 20:1 to 3:1) afforded the title compound (7.5 g, 70% yield) as a white solid. LCMS: RT=0.619 min, m/z=194.1 (M+H)$^+$, $^1$HNMR (400 MHz, CDCl$_3$) δ 7.25-7.22 (m, 2H), 7.06-7.02 (m, 2H), 3.66 (t, J=9.2 Hz, 1H), 3.49-3.44 (m, 2H), 2.96 (s, 3H), 2.55-2.53 (m, 1H), 2.14-2.06 (m, 1H).

Step 5: 3-(4-Fluoro-3-nitrophenyl)-1-methylpyrrolidin-2-one

To a solution of 3-(4-Fluorophenyl)-1-methylpyrrolidin-2-one (7.5 g, 38.8 mmol) in conc. $H_2SO_4$ (80 mL) at −10° C. was added drop-wise nitric acid (4.2 g, 65%, 43.3 mmol, 3 mL). The reaction was stirred at 0° C. for 20 min. TLC (petroleum ether, EtOAc, 1:1, starting material Rf=0.2, product Rf=0.1) showed the reaction was completed. The reaction was quenched by slow addition of ice-water and then extracted with EtOAc (2×400 mL). The combined organic phases were dried over $Na_2SO_4$, filtered and concentrated to afford the title compound (8.9 g, 96% yield) as a white solid. LCMS: RT=0.631 min, m/z=239.1 (M+H)$^+$, $^1$HNMR (400 MHz, CDCl$_3$) δ 8.00-7.98 (m, 1H), 7.62-7.59 (m, 1H), 7.30-7.25 (m, 1H), 3.73 (t, J=5.6 Hz, 1H) 3.51-3.48 (m, 2H), 2.96 (s, 3H), 2.63-2.57 (m, 1H), 2.18-2.13 (m, 1H).

Step 6: 3-(4-But-3-enylamino-3-nitrophenyl)-1-methylpyrrolidin-2-one

To a solution of but-3-enylamine hydrochloride (2.4 g, 22.3 mmol) and $K_2CO_3$ (6 g, 43.4 mmol) in DMF (40 mL), was added compound 3-(4-fluoro-3-nitrophenyl)-1-methyl-pyrrolidin-2-one (3.5 g, 14.7 mmol). The reaction was stirred at 28° C. under nitrogen for 16 h. TLC (petroleum ether:EtOAc, 1:1, starting material Rf=0.1, product Rf=0.2) showed the reaction was completed. The reaction was diluted with water (200 mL) and extracted with EtOAc (2×200 mL). The combined organic phases were washed with brine (2×200 mL), dried over anhydrous $Na_2SO_4$, filtered and concentrated to afford the title compound (5.5 g, crude) as a yellow oil. $^1$HNMR (400 MHz, CDCl$_3$) δ 8.05-8.015 (m, 2H), 7.428-7.4 (m, 1H), 6.852 (d, J=8.8, 1H), 5.874-5.788 (m, 1H) 5.194-5.154 (m, 2H) 3.58-3.348 (m, 5H) 2.927 (s, 3H) 2.508-2.426 (m, 3H) 2.148-2.116 (m, 1H), LCMS: RT=0.790 min, m/z=290.1 (M+H)$^+$ Step 7: 3-(4-But-3-enylamino-3-aminophenyl)-1-methylpyrrolidin-2-one A solution of 3-(4-But-3-enylamino-3-nitrophenyl)-1-methylpyrrolidin-2-one (5.5 g, 19 mmol) in saturation aqueous $NH_4Cl$ (40 mL) and MeOH (40 mL) at 50° C. was added several sections Fe (5.5 g, 98.5 mmol). The reaction was stirred at 90° C. under nitrogen for 3 h. TLC (DCM:MeOH, 20:1, starting material Rf=0.9, product Rf=0.5) showed the reaction was completed. The reaction mixture was filtered through a celite pad. The pad was rinced with MeOH (3×150 mL) and the filtrate was concentrated under reduced pressure to remove MeOH. The residue was diluted with water (200 mL) and extracted with EtOAc (2×300 mL). The combined organic phases were dried over $Na_2SO_4$, filtered and concentrated. Purification by flash chromatography on silica (petroleum ether:EtOAc, 1:1 then DCM:MeOH, 100:1) afforded the title compound (3.6 g, 73% yield) as a red oil. $^1$HNMR (400 MHz, CDCl$_3$) δ 6.695-6.70 (m, 1H), 6.614 (d, J=8 Hz, 2H), 5.905-5.863 (m, 1H) 5.185-5.095 (m, 2H), 3.540-3.374 (m, 3H) 3.16 (t, J=6.4 Hz 2H) 2.925 (s, 3H) 2.451-2.415 (m, 3H) 2.095-2.053 (m, 1H), LCMS: RT=0.561 min, m/z=260.3 (M+H)$^+$ Step 8: 3-(2-Amino-1-but-3-enyl-1H-benzoimidazol-5-yl)-1-methyl-pyrrolidin-2-one hydrobromide A solution of 3-(4-But-3-enylamino-3-aminophenyl)-1-methylpyrrolidin-2-one (3.6 g, 13.9 mmol) and BrCN (1.47 g, 13.9 mmol) in EtOH (35 mL) was stirred at 28° C. under nitrogen for 3 h. TLC (DCM:MeOH, 10:1, starting material Rf=0.7, product Rf=0.1) showed the reaction was completed. The reaction was concentrated under reduced pressure to afford the title compound (5 g, 98.6% yield) as a yellow solid. $^1$H NMR (400 MHz, CDCl$_3$) δ 7.542 (t, J=7.2 Hz 1H), 7.224 (t, J=4 Hz 2H), 5.710-5.642 (m, 1H) 4.972-4.924 (m 2H), 4.078-3.765 (m, 3H) 3.578-3.542 (m, 2H) 2.992 (s, 3H) 2.608-2.599 (m, 1H) 2.408-2.356 (m, 2H) 2.215-2.182 (m, 1H), LCMS: RT=1.767 min, m/z=285 (M+H)$^+$.

Intermediate 12: 3-(2-Amino-1-but-3-enyl-1H-benzoimidazol-5-yl)-1-methyl-piperidin-2-one

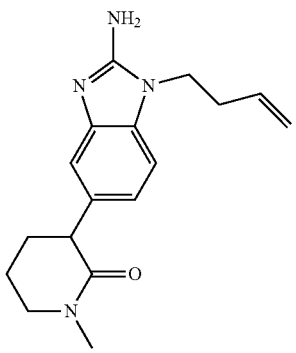 [SMILES: C=CCCn1c(N)nc2cc(C3CCCN(C)C3=O)ccc21]

The title compound was prepared in an analogous fashion to Intermediate 11 by using 3-bromopropanenitrile in place of bromoacetonitrile in step 2. LCMS: RT=1.187 min, m/z=299.2 (M+H)+, 1H NMR (400 MHz, CDCl3) δ 7.17 (s, 1H) 6.955 (d, J=8.4 Hz 1H) 6.864-6.839 (m, 1H) 5.837-5.734 (m, 1H) 5.112-5.056 (m, 2H) 3.808-3.391 (m, 5H) 3.055 (s 3H) 2.449-2.396 (m, 2H) 2.04-1.806 (s, 4H).

Intermediate 13: 3-(1-Allyl-2-amino-1H-benzoimidazol-5-yl)-1-methyl-pyrrolidin-2-one hydrobromide

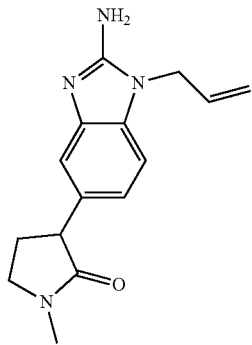 [SMILES: C=CCn1c(N)nc2cc(C3CCN(C)C3=O)ccc21]

The title compound was prepared in an analogous fashion to Intermediate 11 by using prop-2-en-1-amine in place of but-3-enylamine hydrochloride in step 6. LCMS: RT=1.187 min, m/z=299.2 (M+H)+, 1H NMR (400 MHz, CDCl3) δ 7.17 (s, 1H) 6.955 (d, J=8.4 Hz 1H) 6.864-6.839 (m, 1H) 5.837-5.734 (m, 1H) 5.112-5.056 (m, 2H) 3.808-3.391 (m, 5H) 3.055 (s 3H) 2.449-2.396 (m, 2H) 2.04-1.806 (s, 4H). LCMS: RT=0.510 min, m/z=271.1 (M+H)+, 1HNMR: 400 MHz, CDCl3, δ 7.548-7.527 (m, 3H) 7.32 (s, 1H) 7.221-7.201 (m, 1H) 5.743-5.674 (m, 1H) 5.207 (t, J=16 Hz 2H) 4.635 (t, J=5.2 Hz 1H) 4.635 (t, J=11.6 Hz 1H) 3.823 (t, J=9.6 Hz 1H) 3.576-3.54 (m, 1H) 2.998 (s, 3H) 2.623-2.581 (m, 1H) 2.197-2.139 (m, 1H)

Intermediate 14: 3-(2-amino-1-{3-[(tert-butyldimethylsilyl)oxy]propyl}-1H-1,3-benzodiazol-5-yl)-1-methylpyrrolidin-2-one

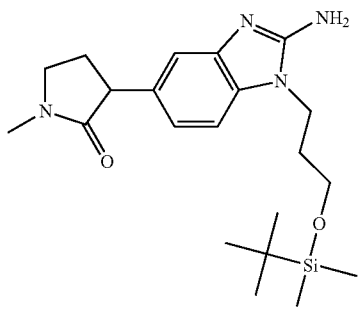

Step 1: 3-(4-fluorophenyl)-1-methylpyrrolidin-2-one

Sodium tert-Butoxyde (1.597 g, 14.23 mmol, 1.50 equiv) was added to a solution of 3-(4-fluorophenyl)pyrrolidin-2-one (Otava Building Blocks, 2 g, 9.49 mmol, 1.00 equiv, 85%) in DMF (20 mL) in several batches at 0° C. After 1 h, iodomethane (1.481 g, 10.43 mmol, 1.10 equiv) was added dropwise. The reaction mixture was stirred for 2 h at 0° C. and quenched by the addition of 100 mL of water. The resulting solution was extracted with EtOAc (3×100 mL). Combined organic phases were washed with brine (2×50 mL), dried over anhydrous sodium sulfate, filtered and concentrated. Purification by flash chromatography on silica (ethyl acetate:petroleum ether, 3:1) afforded the title compound as an yellow oil (1.3 g; 64%). ESI+: M+1: 193.9

Step 2: 3-(4-fluoro-3-nitrophenyl)-1-methylpyrrolidin-2-one

Nitric acid (2 mL, 44.59 mmol, 7.36 equiv) was added dropwise to a solution of 3-(4-fluorophenyl)-1-methylpyrrolidin-2-one (1.3 g, 6.06 mmol, 1.00 equiv, 90%) in sulfuric acid (13 mL) at 0° C. The resulting solution was stirred for 2 h at 0° C. in a water/ice bath and quenched by the addition of 50 mL of water/ice. It was then extracted with EtOAc (2×100 mL). Combined organic phases were washed with brine (2×30 mL), dried over anhydrous sodium sulfate filtered and concentrated to give the title compound as a yellow solid (1.2 g, 75%). ESI+: M+1: 238.9

Step 3: 3-{4-[(3-hydroxypropyl)amino]-3-nitrophenyl}-1-methylpyrrolidin-2-one

A solution of 3-(4-fluoro-3-nitrophenyl)-1-methylpyrrolidin-2-one (1.2 g, 4.53 mmol, 1.00 equiv, 90%), potassium carbonate (1.88 g, 13.60 mmol, 3.00 equiv) and 3-aminopropan-1-ol (681 mg, 9.07 mmol, 2.00 equiv) in DMF (10 mL) was stirred for 1 h at 700° C. The reaction mixture was then quenched by the addition of 100 mL of water and extracted with EtOAc (2×100 mL). Combined organic phases were washed with brine (2×50 mL), dried over anhydrous sodium sulfate, filtered and concentrated. Purification by flash chromatography on silica (DCM:MeOH, 98:2) afforded the title compound as a red oil (1.25; 89%). ESI+: M+1: 294.1

Step 4: 3-{3-amino-4-[(3-hydroxypropyl)amino]phenyl}-1-methylpyrrolidin-2-one

Raney Ni (20 mg, 0.23 mmol, 2.40 equiv) was added to a nitrogen purged solution of 3-[4-[(3-hydroxypropyl)amino]-3-nitrophenyl]-1-methylpyrrolidin-2-one (30 mg, 0.10 mmol, 1.00 equiv, 95%) in MeOH (3 mL). The reaction mixture was then hydrogenated (1 atm) for 3 h at RT. The solids were filtered out and resulting mixture was concentrated under vacuum to afford the tittle compound as a purple oil (880 mg, 86%). ESI+: M+1: 264.1

Step 5: 3-[2-amino-1-(3-hydroxypropyl)-1H-1,3-benzodiazol-5-yl]-1-methylpyrrolidin-2-one A solution of 3-[3-amino-4-[(3-hydroxypropyl)amino]phenyl]-1-methylpyrrolidin-2-one (830 mg, 2.63 mmol, 1.00 equiv) and BrCN (335 mg, 3.16 mmol, 1.20 equiv) in ethanol (10 mL) was stirred for 2 h at 50° C. It was then concentrated under vacuum to afford the title compound as a purple solid (1.1 g, 100%). ESI+: M+1: 289.1

Step 6: 3-(2-amino-1-{3-[(tert-butyldimethylsilyl)oxy]propyl}-1H-1,3-benzodiazol-5-yl)-1-methylpyrrolidin-2-one: solution of tert-butyl(chloro)dimethylsilane (566 mg, 3.76 mmol, 1.20 equiv) in DCM (2 mL) was added dropwise to a solution of 3-[2-amino-1-(3-hydroxypropyl)-1H-1,3-benzodiazol-5-yl]-1-methylpyrrolidin-2-one (1.29 g, 3.13 mmol, 1.00 equiv) and 1H-imidazole (469 mg, 6.89 mmol, 2.20 equiv) in DCM (50 mL) maintained at 0° C. The resulting solution was stirred for 4 h at room temperature.

The solids were then filtered out and the filtrate was concentrated under vacuum. Purification by flash chromatography on silica (DCM:MeOH, (97.3:2.7) afforded the title compound as a brown solid (1.1 g, 84%). ESI$^+$: M+1: 403.3.

Intermediate 15: 4-[2-amino-1-(3-hydroxypropyl)-1H-1,3-benzodiazol-5-yl]-1,3,3-trimethylpyrrolidin-2-one

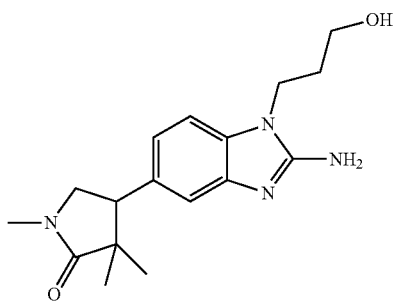 [SMILES: CN1CC(c2ccc3c(c2)nc(N)n3CCCO)C(C)(C)C1=O]

Step 1: methyl 3-(4-fluorophenyl)-2,2-dimethyl-4-nitrobutanoate: n-BuLi (2.5M in THF, 6.765 mL, 16.37 mmol, 1.60 equiv) was added dropwise to a solution of di-isopropylamine (1.744 g, 16.37 mmol, 1.60 equiv) in THF (40 mL) maintained under nitrogen atmosphere at −60° C. The resulting solution was stirred for 0.5 h at −30° C. before the addition of methyl 2-methylpropanoate (1.65 g, 15.35 mmol, 1.50 equiv). The reaction mixture was then stirred for 1 h at −40° C. and a solution of 1-fluoro-4-[(E)-2-nitroethenyl]benzene (1.900 g, 10.23 mmol, 1.00 equiv) in THF (10 mL) was added dropwise while stirring at −60° C. Temperature was brought back to RT and the mixture was stirred for 1 h before the addition of sat. NH$_4$Cl solution (50 mL). The resulting solution was extracted with EtOAc (2×50 mL). Combined organic phases were washed with brine (50 mL), dried over anhydrous sodium sulfate, filtered and concentrated. Purification by flash chromatography on silica (EtOAc:petroleum ether, 1:10) afforded the title compound as an yellow oil (2 g, 65%). 1H NMR (300 MHz, CDCl3, ppm) δ: 7.24-7.10 (m, 2H), 7.07-6.94 (m, 2H), 4.92 (dd, J=13.1, 11.3 Hz, 1H), 4.77 (dd, J=13.1, 4.2 Hz, 1H), 3.76 (dd, J=11.3, 4.2 Hz, 1H), 3.69 (s, 3H), 1.18 (d, J=13.5 Hz, 6H).

Step 2: 4-(4-fluorophenyl)-3,3-dimethylpyrrolidin-2-one: A degassed suspension of methyl 3-(4-fluorophenyl)-2,2-dimethyl-4-nitrobutanoate (2.0 g, 6.68 mmol, 1.00 equiv) and Raney Ni (603 mg, 6.69 mmol, 1.00 equiv) in EtOH (60 mL) was hydrogenated at 50° C. under 15 atm of hydrogen pressure O/N. It was then filtered through a Celite pad and the filtrate concentrated under reduced pressure to afford the title compound as a yellow solid (2.0 g, quantitative). ESI$^+$: M+1: 208.0.

Step 3: 4-(4-fluorophenyl)-1,3,3-trimethylpyrrolidin-2-one

Iodomethane (1.557 g, 10.42 mmol, 1.50 equiv) was added to a suspension of sodium hydride (361 mg, 9.03 mmol, 1.30 equiv, 60%) and 4-(4-fluorophenyl)-3,3-dimethylpyrrolidin-2-one (1.6 g, 6.95 mmol, 1.00 equiv) in THF (50 mL) maintained under nitrogen atmosphere and at OC. The resulting solution was stirred for 30 min at 0° C., it was allowed to warm to RT and stirred O/N. The reaction was then quenched with water (30 mL) and extracted with EtOAc (3×25 mL). Combined organic phases were dried over anhydrous sodium sulfate, filtered and concentrated under vacuum. Purification by flash chromatography on silica (DCM:MeOH, 10:1) afforded the title compound as a yellow oil (1.5 g, 88%). 1H NMR (300 MHz, CDCl3, ppm) δ 7.22-7.11 (m, 2H), 7.09-6.96 (m, 2H), 3.65-3.46 (m, 2H), 3.22 (t, J=8.1 Hz, 1H), 2.95 (s, 3H), 1.21 (s, 3H), 0.73 (s, 3H).

Step 4: 4-(4-fluoro-3-nitrophenyl)-1,3,3-trimethylpyrrolidin-2-one

The title compound was obtained following procedure described for intermediate 14, step 2 but starting from 4-(4-fluorophenyl)-1,3,3-trimethylpyrrolidin-2-one (1.500 g, 6.10 mmol, 1.00 equiv) yellow solid (1.8 g, 100%). ESI$^+$: M+1: 226.9.

Step 5: 4-{4-[(3-hydroxypropyl)amino]-3-nitrophenyl}-1,3,3-trimethylpyrrolidin-2-one The title compound was obtained following procedure described for intermediate 14, step 3 but starting from 4-(4-fluoro-3-nitrophenyl)-1,3,3-trimethylpyrrolidin-2-one (1.70 g, 5.75 mmol, 1.00 equiv) as a red oil (2 g, 97%). ESI$^+$: M+1: 322.4.

Step 6: 4-{3-amino-4-[(3-hydroxypropyl)amino]phenyl}-1,3,3-trimethylpyrrolidin-2-one The title compound was obtained following procedure described for intermediate 14, step 4 but starting from 4-[4-[(3-hydroxypropyl)amino]-3-nitrophenyl]-1,3,3-trimethylpyrrolidin-2-one (900 mg 1.00 equiv) as a brown oil (800 mg, 98%). ESI$^+$: M+1: 292.4.

Step 7: 4-[2-amino-1-(3-hydroxypropyl)-1H-1,3-benzodiazol-5-yl]-1,3,3-trimethylpyrrolidin-2-one The title compound was obtained following procedure described for intermediate 14, step 5 but starting from 4-[3-amino-4-[(3-hydroxypropyl)amino]phenyl]-1,3,3-trimethylpyrrolidin-2-one (1.7 g, 5.25 mmol, 1.00 equiv) as a brown solid (1.5 g, 81%). ESI$^+$: M+1: 292.4.

Intermediate 16: 2-{2-amino-1-[3-(benzyloxy)-2-fluoro-2-methylpropyl]-1H-1,3-benzodiazol-5-yl}-4-methylmorpholin-3-one

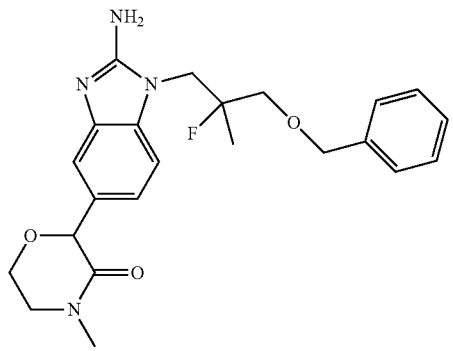 [SMILES: CN1CCOC(c2ccc3c(c2)nc(N)n3CC(C)(F)COCc2ccccc2)C1=O]

Step 1: methyl(2-{[tris(propan-2-yl)silyl]oxy}ethyl)amine 2,6-dimethylpyridine (14 g, 131 mmol, 1.00 equiv) was added dropwise to a solution of 2-(methylamino)ethan-1-ol (9.8 g, 130.5 mmol, 1.00 equiv) and tris(propan-2-yl)silyl trifluoromethanesulfonate (100 g, 326.35 mmol, 2.50 equiv) in DCM (300 mL) maintained under nitrogen atmosphere and at 0° C. The reaction mixture was allowed to warm to RT and stirred for 5 h. It was quenched by the addition of water/ice (100 mL) and extracted with DCM (3×30 mL). Combined organic phases were washed with brine (50 mL), dried over anhydrous sodium sulfate, filtered and concentrated to give the title compound as a yellow oil (27 g, 72%).

Step 2: N-{2-[(tert-butyldimethylsilyl)oxy]ethyl}-2-(4-fluorophenyl)-2-hydroxy-N-methylacetamide A mixture of [2-[(tert-butyldimethylsilyl)oxy]ethyl](methyl)amine (3.4 g, 16.2 mmol, 1.00 equiv), 2-(4-fluorophenyl)-2-hydroxyacetic acid (4.1 g, 24.10 mmol, 1.49 equiv), HATU (7.4 g, 19.46 mmol, 1.20 equiv) and DIEA (3.2 g, 24.76 mmol, 1.53 equiv) in DMF (10 mL) was stirred O/n at RT. The reaction mixture was then quenched by the addition of water (50 mL) and extracted with EtOAc (3×30 mL). Combined organic phases were washed with brine (20 mL), dried over anhydrous sodium sulfate, filtered and concentrated. Purification by flash chromatography on silica (EtOAc:petroleum ether, gradient from 1:10 to 7:3) afforded the title compound as a yellow oil (2.0 g, 33%).

Step 3: ({2-[(tert-butyldimethylsilyl)oxy]ethyl}(methyl)carbamoyl)(4-fluorophenyl)methyl methanesulfonate MsCl (740 mg, 6.46 mmol, 1.20 equiv) was added dropwise to a solution of N-[2-[(tert-butyldimethylsilyl)oxy]ethyl]-2-(4-fluorophenyl)-2-hydroxy-N-methylacetamide (2.3 g, 5.39 mmol, 1.00 equiv) and TEA (820 mg, 8.10 mmol, 1.50 equiv) in DCM (60 mL) maintained under nitrogen atmosphere and ° C. The reaction mixture was stirred for 1 h at ° C. and quenched by the addition of water (100 mL). It was extracted with EtOAc (3×40 mL) and the combined organic phases were washed with brine (30 mL), dried over anhydrous sodium sulfate, filtered and concentrated to afford the title compound as a yellow oil (2.5 g, 88%).

Step 4: 2-(4-fluorophenyl)-4-methylmorpholin-3-one

A solution of ([2-[(tert-butyldimethylsilyl)oxy]ethyl](methyl)carbamoyl)(4-fluorophenyl)methyl methanesulfonate (2.5 g, 4.77 mmol, 1.00 equiv) and TBAF (5 g, 19.12 mmol, 4.01 equiv) in THF (60 mL) was stirred for 16 h at RT. The reaction was then quenched by the addition of water (60 mL) and extracted with EtOAc (3×40 mL). Combined organic phases were washed with brine (30 mL), dried over anhydrous sodium sulfate, filtered and concentrated to afford the title compound as a yellow oil (1 g, 83%). ESI$^+$: M+1: 210.0.

Step 5: 2-(4-fluoro-3-nitrophenyl)-4-methylmorpholin-3-one

The title compound was obtained following procedure described for intermediate 14, step 2 but starting from 2-(4-fluorophenyl)-4-methylmorpholin-3-one (1 g, 3.93 mmol, 1.00 equiv) as a yellow solid (500 mg, 47%). ESI$^+$: M+1: 255.0.

Step 6: 2-(4-{[3-(benzyloxy)-2-fluoro-2-methylpropyl]amino}-3-nitrophenyl)-4-methylmorpholin-3-one:

the title compound was obtained following procedure described for intermediate 14, step 3 but starting from 2-(4-fluoro-3-nitrophenyl)-4-methylmorpholin-3-one (350 mg, 1.29 mmol, 1.00 equiv) and 3-(benzyloxy)-2-fluoro-2-methylpropan-1-amine (Intermediate amine 2, 306 mg, 1.55 mmol, 1.20 equiv) as a yellow oil (460 mg, 72%). ESI$^+$: M+1: 432.2.

Step 7: 2-(3-amino-4-{[3-(benzyloxy)-2-fluoro-2-methylpropyl]amino}phenyl)-4-methylmorpholin-3-one A degassed suspension of 2-(4-[[3-(benzyloxy)-2-fluoro-2-methylpropyl]amino]-3-nitrophenyl)-4-methylmorpholin-3-one (450 mg, 0.91 mmol, 1.00 equiv, 87.3%) and Palladium carbon (15 mg, 0.01 mmol, 0.01 equiv, 10%) in MeOH (10 mL) was hydrogenated at room temperature under 30 psi of hydrogen pressure for 1 h. It was then filtered through a Celite pad and the filtrate was concentrated to afford the title compound as a red solid (340 mg, 83%). ESI$^+$: M+1: 402.2.

Step 8: 2-{2-amino-1-[3-(benzyloxy)-2-fluoro-2-methylpropyl]-1H-1,3-benzodiazol-5-yl}-4-methylmorpholin-3-one The title compound was obtained following procedure described for intermediate 14, step 5 but starting from 2-(3-amino-4-[[3-(benzyloxy)-2-fluoro-2-methylpropyl]amino]phenyl)-4-methylmorpholin-3-one (330 mg, 0.73 mmol, 1.00 equiv) as a red solid (255 mg, 55%). ESI$^+$: M+1: 427.1.

Intermediate 17: 3-(2-amino-1-{3-[(tert-butyldimethylsilyl)oxy]propyl}-1H-1,3-benzodiazol-5-yl)-1,3-dimethylpyrrolidin-2-one

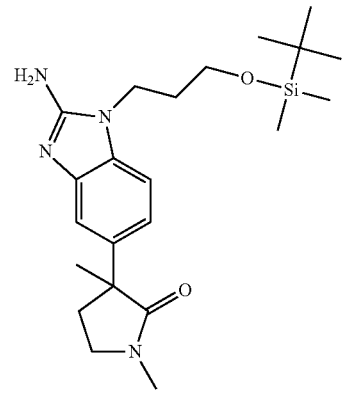 [SMILES: CN1CCC(C)(c2ccc3c(c2)nc(N)n3CCCO[Si](C)(C)C(C)(C)C)C1=O]

Step 1: 3-(4-fluorophenyl)-1,3-dimethylpyrrolidin-2-one

Sodium tert-butoxyde (1.63 g, 14.24 mmol, 1.50 equiv) was added in several batches to a solution of 3-(4-fluorophenyl)pyrrolidin-2-one (intermediate 11, step 1, 2 g, 9.49 mmol, 1.00 equiv) in DMF (20 mL) maintained at 0° C. The reaction mixture was then stirred at 0° C. for 60 min before the dropwise addition of iodomethane (1.5 g, 10.36 mmol, 1.09 equiv). The resulting mixture was stirred for an additional 2 h at 0° C. and quenched with water (100 mL). The resulting solution was extracted with ethyl acetate 3×100 mL) and the combined organic phases were washed with of brine (2×50 mL), dried over anhydrous sodium sulfate, filtered and concentrated. Purification by flash chromatography on silica (ethyl acetate:petroleum ether, 3:1) afforded the title compound as a yellow oil (500 mg, 23%). ESI+ (M+1): 208.2.

Step 2: 3-(4-fluoro-3-nitrophenyl)-1,3-dimethylpyrrolidin-2-one

The title compound was obtained following procedure described for intermediate 14, step 2 but starting from 3-(4-fluorophenyl)-1,3-dimethylpyrrolidin-2-one (480 mg, 2.08 mmol, 1.00 equiv) as a yellow solid (580 mg, 99%). ESI+ (M+1): 253.2.

Step 3: 3-{4-[(3-hydroxypropyl)amino]-3-nitrophenyl}-1,3-dimethylpyrrolidin-2-one The title compound was obtained following procedure described for intermediate 11, step 3 but starting from 3-(4-fluoro-3-nitrophenyl)-1,3-dimethylpyrrolidin-2-one (560 mg, 2.00 mmol, 1.00 equiv) and 3-aminopropan-1-ol (307 mg, 4.01 mmol, 2.00 equiv) as an orange solid (690 mg, 101%). ESI+ (M+1): 308.2.

Step 4: 3-[4-({3-[(tert-butyldimethylsilyl)oxy]propyl}amino)-3-nitrophenyl]-1,3-dimethylpyrrolidin-2-one The title compound was obtained following procedure described for intermediate 14, step 6 but starting from 3-[4-[(3-hydroxypropyl)amino]-3-nitrophenyl]-1,3-dimethylpyrrolidin-2-one (670 mg, 1.96 mmol, 1.00 equiv) as a brown solid (980 mg quantitative). ESI+ (M+1): 422.1.

Step 5: 3-[3-amino-4-({3-[((tert-butyldimethylsilyl)oxy]propyl}amino)phenyl]-1,3-dimethylpyrrolidin-2-one The title compound was obtained following procedure described for intermediate 14, step 4 but starting from 3-[4-([3-[(tert-butyldimethylsilyl)oxy]propyl]amino)-3-nitrophenyl]-1,3-dimethylpyrrolidin-2-one (950 mg, 2.03 mmol, 1.00 equiv) as a yellow oil (840 mg, 95%). ESI+ (M+1): 392.3.

Step 6: 3-(2-amino-1-{3-[(tert-butyldimethylsilyl)oxy]propyl}-1H-1,3-benzodiazol-5-yl)-1,3-dimethylpyrrolidin-2-one The title compound was obtained following procedure described for intermediate 14, step 6 but starting from 3-[3-amino-4-([3-[(tert-butyldimethylsilyl)oxy]propyl]amino)phenyl]-1,3-dimethylpyrrolidin-2-one (820 mg, 1.88 mmol, 1.00 equiv) as a beige solid (850 mg, 98%). ESI+ (M+1): 417.2.

Intermediate 18: 5-[2-amino-1-(3-hydroxypropyl)-1H-1,3-benzodiazol-5-yl]-1,5-dimethylpyrrolidin-2-one

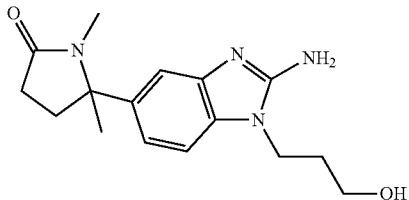 [SMILES: CN1C(=O)CCC1(C)c1ccc2c(c1)nc(N)n2CCCO]

Step 1: methyl 4-(4-fluorophenyl)-4-nitropentanoate

A solution of DBU (639 mg, 3.99 mmol, 0.50 equiv) in MeCN (2 mL) was added dropwise to a solution of 1-fluoro-4-(1-nitroethyl)benzene (Aurora Building Blocks, 1.5 g, 7.98 mmol, 1.00 equiv) and methyl prop-2-enoate (1.446 g, 15.96 mmol, 2.00 equiv) in MeCN (40 mL) maintained under nitrogen atmosphere and at 0° C. The reaction mixture was stirred for 3 h at RT, quenched with sat. NH$_4$Cl (50 mL) and extracted with EtOAc (3×50 mL). Combined organic phases were washed with brine, dried over anhydrous sodium sulfate, filtered and concentrated. Purification by flash chromatography on silica (petroleum ether, EtOAc, gradient from 100:0 to 90:10 afforded the title compound as a yellow oil (1.8 g, 80%). 1H NMR (400 MHz, CDCl3, ppm) δ 7.42-7.35 (m, 2H), 7.12-7.03 (m, 2H), 3.67 (s, 3H), 2.84-2.72 (m, 1H), 2.72-2.61 (m, 1H), 2.34-2.26 (m, 2H), 1.95 (s, 3H).

Step 2: 5-(4-fluorophenyl)-5-methylpyrrolidin-2-one

A solution of methyl 4-(4-fluorophenyl)-4-nitropentanoate (8.0 g, 28.2 mmol, 1.00 equiv), in MeOH (150 mL) was purged with nitrogen before the addition of Raney-Ni (2.54 g, 28.2 mmol, 1.00 equiv). The resulting reaction mixture was then hydrogenated under atm. Pressure at RT for 16 h. It was then filtered through a Celite pad and the filtrate was concentrated under reduced pressure. Purification by flash chromatography on silica (DCM:MeOH, gradient from 100:0 to 90:10) afforded the title compound as a colorless solid (5 g, 83%). 1H NMR (300 MHz, CDCl3, ppm) δ 7.37-7.31 (m, 2H), 7.09-7.01 (m, 2H), 6.94 (s, 1H), 2.51-2.35 (m, 2H), 2.33-2.21 (m, 2H), 1.65 (s, 3H).

Step 3: 5-(4-fluorophenyl)-1,5-dimethylpyrrolidin-2-one

Iodomethane (5.220 g, 34.94 mmol, 1.50 equiv) was added to a suspension of sodium hydride (1.21 g, 30.3 mmol, 1.30 equiv, 60%) and 4-(4-fluorophenyl)-3,3-dimethylpyrrolidin-2-one (5.0 g, 23.29 mmol, 1.3 equiv) in DMF (75 mL) maintained under nitrogen atmosphere and at 0° C. The reaction mixture was allowed to warm to RT and stirred 1 h at RT. It was then quenched with water (30 mL) and extracted with EtOAc (3×20 mL). Combined organic phases were dried over anhydrous sodium sulfate, filtered and concentrated under vacuum. Purification by flash chromatography on silica (DCM:MeOH, gradient from 10:0 to 15:1) afforded the title compound as a yellow solid (5 g, 93%). 1H NMR (300 MHz, CDCl$_3$) δ 7.25-7.14 (m, 2H), 7.12-6.99 (m, 2H), 2.66 (s, 3H), 2.53-2.39 (m, 2H), 2.19-2.01 (m, 2H), 1.67 (s, 3H). ESI$^+$ (M+1): 208.0.

Step 4: 5-(4-fluoro-3-nitrophenyl)-1,5-dimethylpyrrolidin-2-one

The title compound was obtained following procedure described for Intermediate 14, step 2 but starting from 5-(4-fluorophenyl)-1,5-dimethylpyrrolidin-2-one (5.500 g, 23.88 mmol, 1.00 equiv) as a yellow oil (6 g, 82%). ESI$^+$ (M+1): 253.0.

Step 5: 5-{4-[(3-hydroxypropyl)amino]-3-nitrophenyl}-1,5-dimethylpyrrolidin-2-one The title compound was obtained following procedure described for Intermediate 14, step 3 but starting from 5-(4-fluoro-3-nitrophenyl)-1,5-dimethylpyrrolidin-2-one (2.5 g, 8.92 mmol, 1.00 equiv) and 3-aminopropan-1-ol (1.06 g, 13.38 mmol, 1.50 equiv) as a red oil (3 g, 98%). ESI$^+$ (M+1): 308.0

Step 6: 5-[4-({3-[(tert-butyldimethylsilyl)oxy]propyl}amino)-3-nitrophenyl]-1,5-dimethylpyrrolidin-2-one The title compound was obtained following procedure described for Intermediate 14, step 6 but starting from 5-[4-[(3-hydroxypropyl)amino]-3-nitrophenyl]-1,5-dimethylpyrrolidin-2-one (3.0 g, 8.78 mmol, 1.00 equiv) as a red oil (4 g, 97%). ESI$^+$ (M+1): 422.1.

Step 7: 5-[3-amino-4-({3-[(tert-butyldimethylsilyl)oxy]propyl}amino)phenyl]-1,5-dimethylpyrrolidin-2-one The title compound was obtained following procedure described for Intermediate 14, step 4 but starting from 5-[4-([3-[(tert-butyldimethylsilyl)oxy]propyl]amino)-3-nitrophenyl]-1,5-dimethylpyrrolidin-2-one (3.5 g, 7.47 mmol, 1.00 equiv) as a brown oil (4 g, quantitative). ESI$^+$ (M+1): 392.1.

Step 8: 5-[2-amino-1-(3-hydroxypropyl)-1H-1,3-benzodiazol-5-yl]-1,5-dimethylpyrrolidin-2-one The title compound was obtained following procedure described for Intermediate 14, step 5 but starting from 5-[3-amino-4-([3-[(tert-butyldimethylsilyl)oxy]propyl]amino)phenyl]-1,5-dimethylpyrrolidin-2-one (3.200 g, 7.35 mmol, 1.00 equiv) as a brown oil (3 g, quantitative). ESI$^+$ (M+1): 303.2.

Intermediate 19: 3-{2-amino-1-[3-(benzyloxy)-2-fluoro-2-methylpropyl]-1H-1,3-benzodiazol-5-yl}-1-methylpiperidin-2-one

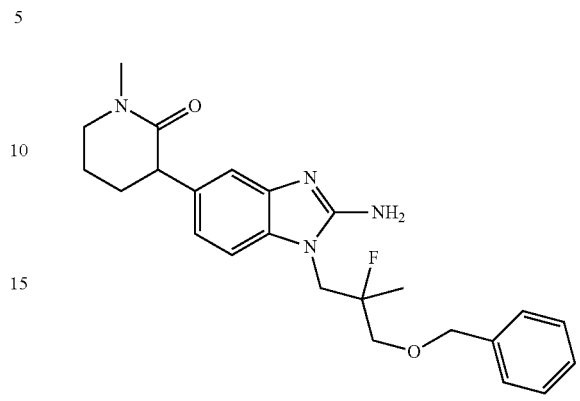

The title compound was obtained following a similar procedure as described for Intermediate 2, but using intermediate amine 3 in place of intermediate amine 3-aminopropanol-1 in step 4 as a yellow solid. ESI$^+$ (M+1): 425.0.

Example 1: (E)-N-(1-(3-hydroxypropyl)-5-(1-methyl-2-oxopiperidin-3-yl)-1H-benzo[d]imidazol-2(3H)-ylidene)-3-(trifluoromethyl)benzamide (1)

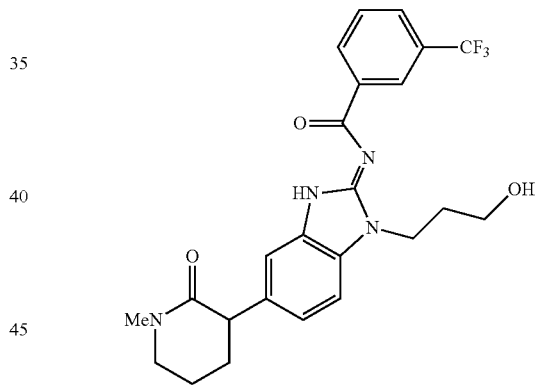

Step 1: (E)-N-(5-(1-methyl-2-oxopiperidin-3-yl)-1-(3-((triisopropylsilyl)oxy)propyl)-1H-benzo[d]imidazol-2(3H)-ylidene)-3-(trifluoromethyl)benzamide In a glass RBF equipped with a Teflon-coated magnetic stirrer was dissolved Intermediate 2 (1 eq.), 3-trifluoromethyl-benzoic acid (1.1 eq.) and HATU (1.2 eq.) in DMF (0.1 M). To this was then added ethyl-diisopropyl-amine (2.5 eq.) and the resulting yellow solution was allowed to stir at RT for 14 h. The crude reaction mixture was diluted with EtOAc and washed sequentially with water, 10% aq. NaHCO$_3$, 10% aq. NH$_4$Cl, water and brine. The organic extract was then dried over Na$_2$SO$_4$, filtered and the filtrate concentrated in vacuo. Further purification by way of column chromatography (SiO$_2$, gradient elution, 1:1 (v/v) Hex:EtOAc→EtOAc) furnished the desired product as viscous oil (68% yield).

Step 2: (E)-N-(1-(3-hydroxypropyl)-5-(1-methyl-2-oxopiperidin-3-yl)-1H-benzo[d]imidazol-2(3H)-ylidene)-3-(trifluoromethyl)benzamide In a glass RBF equipped with a Teflon-coated magnetic stirrer was dissolved (E)-N-(5-(1-methyl-2-oxopiperidin-3-yl)-1-(3-((triisopropylsilyl)oxy)propyl)-1H-benzo[d]imidazol-2(3H)-ylidene)-3-(trifluoromethyl)benzamide (1 eq.) from the previous step in THF (0.1 M). To this was then added tetrabutylammonium fluoride (3.5 eq., 1 M solution in THF) drop-wise over a period of 1 min. The resulting mixture was allowed to stir at RT for 3 h. The crude reaction mixture was diluted with EtOAc and washed sequentially with 10% aq. NaHCO$_3$, water and brine. The organic extract was then dried over Na$_2$SO$_4$, filtered and the filtrate concentrated in vacuo. Trituration of the crude product thus obtained in ether and hexanes afforded the title product as a white solid (42% yield). ESI$^+$: M+1: 475. $^1$H NMR (300 MHz, CDCl$_3$) δ 12.42 (s, 1H), 8.50 (d, J=7.8 Hz, 1H), 8.46-8.34 (m, 1H), 7.74 (d, J=7.8 Hz, 1H), 7.58 (t, J=7.8 Hz, 1H), 7.31-7.12 (m, 3H), 4.77-4.70 (m, 1H), 4.46 (t, J=6.0 Hz, 2H), 3.74 (dd, J=8.6, 5.8 Hz, 1H), 3.57-3.33 (m, 4H), 3.05 (s, 3H), 2.31-2.14 (m, 1H), 2.10-1.82 (m, 5H).

Example 1a and 1b: (S,E)-N-(1-(3-hydroxypropyl)-5-(1-methyl-2-oxopiperidin-3-yl)-1H-benzo[d]imidazol-2(3H)-ylidene)-3-(trifluoromethyl)benzamide (1a) and (R,E)-N-(1-(3-hydroxypropyl)-5-(1-methyl-2-oxopiperidin-3-yl)-1H-benzo[d]imidazol-2(3H)-ylidene)-3-(trifluoromethyl)benzamide (1b)

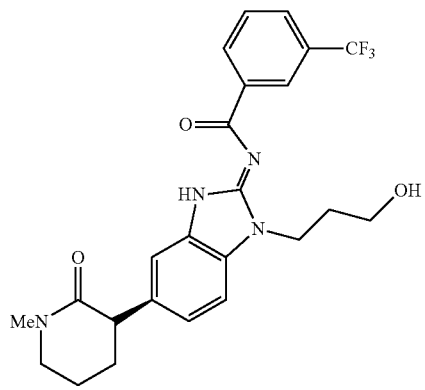 [SMILES: CN1CCCC(c2ccc3c(c2)[nH]/c(=N\C(=O)c2cccc(C(F)(F)F)c2)n3CCCO)C1=O]

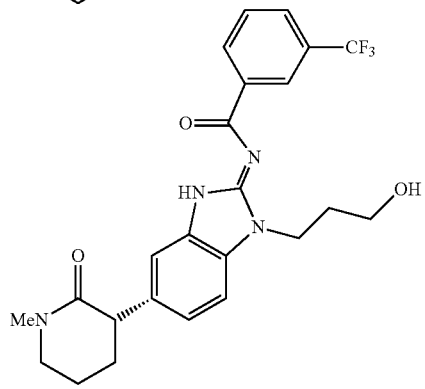

The enantiomers in Example 1 were readily resolved via chiral SFC (ChiraCel OJ 10×250 mm, 5 m column, isocratic 55% MeOH+0.1% aq. NH$_4$OH, 10 mL/min, 100 Bar CO$_2$ 35° C.) into 1a (retention time: 2.74 min) and 1b (retention time: 7.56 min).

Example 2a: (E)-3-(difluoromethyl)-N-(1-((S)-2-fluoro-3-hydroxy-2-methylpropyl)-5-(1-methyl-2-oxopiperidin-3-yl)-1H-benzo[d]imidazol-2(3H)-ylidene)benzamide (2a)

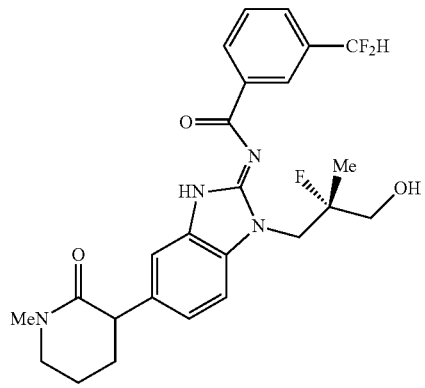 [SMILES: CN1CCCC(c2ccc3c(c2)[nH]/c(=N\C(=O)c2cccc(C(F)F)c2)n3C[C@](C)(F)CO)C1=O]

Prepared in an analogous fashion to Example 1, but using Intermediate 9 (1 eq.) in place of Intermediate 2 and 3-difluoromethyl-benzoic acid (1.2 eq.) in place of 3-trifluoromethyl-benzoic acid in step 1. ESI$^+$: M+1: 489. $^1$H NMR (300 MHz, CDCl$_3$) δ 12.46 (s, 1H), 8.34-8.24 (m, 2H), 7.67 (d, J=7.7 Hz, 1H), 7.56 (t, J=7.7 Hz, 1H), 7.42-7.30 (m, 1H), 7.26-7.11 (m, 2H), 6.73 (t, J=56.3 Hz, 1H), 5.78-5.72 (m, 1H), 4.70 (dd, J=32.4, 15.3 Hz, 1H), 4.20 (dd, J=15.2, 9.7 Hz, 1H), 3.75 (t, J=7.3 Hz, 1H), 3.59-3.22 (m, 4H), 3.05 (s, 3H), 2.25-2.18 (m, 1H), 2.10-1.79 (m, 3H), 1.65 (d, J=22.2 Hz, 3H).

Example 2b: (E)-3-(difluoromethyl)-N-(1-((R)-2-fluoro-3-hydroxy-2-methylpropyl)-5-(1-methyl-2-oxopiperidin-3-yl)-1H-benzo[d]imidazol-2(3H)-ylidene)benzamide (2b)

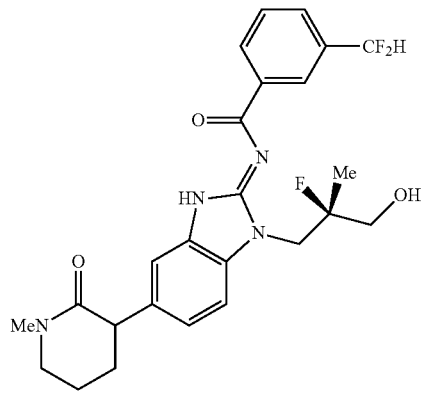 [SMILES: CN1CCCC(c2ccc3c(c2)[nH]/c(=N\C(=O)c2cccc(C(F)F)c2)n3C[C@@](C)(F)CO)C1=O]

Prepared in an analogous fashion to Example 1, but using Intermediate 10 (1 eq.) in place of Intermediate 2 and 3-difluoromethyl-benzoic acid (1.2 eq.) in place of 3-trifluoromethyl-benzoic acid in step 1. ESI+: M+1: 489. 1H NMR (300 MHz, CDCl3) δ 12.48 (s, 1H), 8.34-8.24 (m, 2H), 7.68 (d, J=7.7 Hz, 1H), 7.57 (t, J=7.7 Hz, 1H), 7.43-7.30 (m, 1H), 7.21-7.15 (m, 2H), 6.73 (t, J=56.3 Hz, 1H), 5.78-5.72 (m, 1H), 4.70 (dd, J=32.1, 15.1 Hz, 1H), 4.29-4.14 (m, 1H), 3.74 (t, J=7.3 Hz, 1H), 3.58-3.30 (m, 4H), 3.06 (s, 3H), 2.30-2.13 (m, 1H), 2.08-1.77 (m, 3H), 1.70 (d, J=22.2 Hz, 3H).

Example 3a, 3b, 3c and 3d: 3-(difluoromethyl)-N-[(2E)-1-[(2R)-2-fluoro-3-hydroxy-2-methylpropyl]-5-[(3R)-1-methyl-2-oxopiperidin-3-yl]-2,3-dihydro-H-1,3-benzodiazol-2-ylidene]benzamide (3a), 3-(difluoromethyl)-N-[(2E)-1-[(2S)-2-fluoro-3-hydroxy-2-methylpropyl]-5-[(3S)-1-methyl-2-oxopiperidin-3-yl]-2,3-dihydro-1H-1,3-benzodiazol-2-ylidene]benzamide (3b), 3-(difluoromethyl)-N-[(2E)-1-[(2S)-2-fluoro-3-hydroxy-2-methylpropyl]-5-[(3R)-1-methyl-2-oxopiperidin-3-yl]-2,3-dihydro-1H-1,3-benzodiazol-2-ylidene]benzamide (3c) and 3-(difluoromethyl)-N-[(2E)-1-[(2R)-2-fluoro-3-hydroxy-2-methylpropyl]-5-[(3S)-1-methyl-2-oxopiperidin-3-yl]-2,3-dihydro-1H-1,3-benzodiazol-2-ylidene]benzamide (3d)

Step 1: N-{1-[3-(benzyloxy)-2-fluoro-2-methylpropyl]-5-(1-methyl-2-oxopiperidin-3-yl)-1H-1,3-benzodiazol-2-yl}-3-(difluoromethyl)benzamide

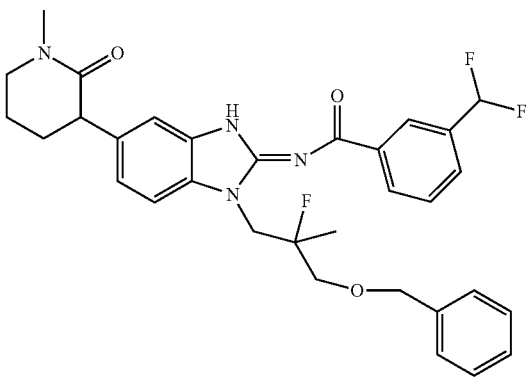 [SMILES: CN1CCCC(c2ccc3c(c2)[nH]/c(=N\C(=O)c2cccc(C(F)F)c2)n3CC(C)(F)COCc2ccccc2)C1=O]

A solution of 3-[2-amino-1-[3-(benzyloxy)-2-fluoro-2-methylpropyl]-1H-1,3-benzodiazol-5-yl]-1-methylpiperidin-2-one (intermediate 19, 501 mg, 1.06 mmol, 1.10 equiv), 3-(difluoromethyl)benzoic acid (175 mg, 0.97 mmol, 1.00 equiv), HATU (406 mg, 1.01 mmol, 1.05 equiv) and DIEA (328 mg, 2.41 mmol, 2.50 equiv) in DMF (5 mL) was stirred O/N at RT. The reaction mixture was diluted with EtOAc (100 mL), washed with brine (3×100 mL), dried over anhydrous sodium sulfate, filtered and concentrated. Purification by flash chromatography on silica (DCM:MeOH, 10:1) afforded the title compound as a brown oil (570 mg, 92%). ESI+ (M+1): 579.4.

Step 2: 3-(difluoromethyl)-N-[(2E)-1-[2-fluoro-3-hydroxy-2-methylpropyl]-5-[1-methyl-2-oxopiperidin-3-yl]-2,3-dihydro-1H-1,3-benzodiazol-2-ylidene]benzamide

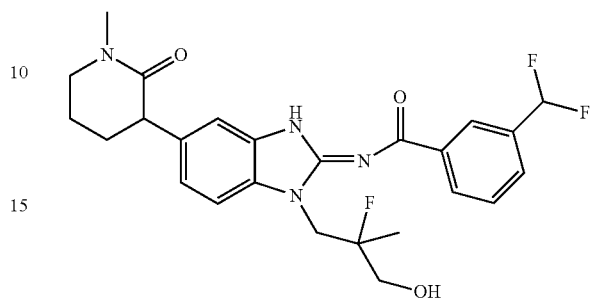

A solution of N-[(2E)-1-[3-(benzyloxy)-2-fluoro-2-methylpropyl]-5-(1-methyl-2-oxopiperidin-3-yl)-2,3-dihydro-1H-1,3-benzodiazol-2-ylidene]-3-(difluoromethyl)benzamide (570 mg, 0.89 mmol, 1.00 equiv) and hydrogen chloride (0.3 mL, 1.18 mmol, 11.14 equiv, 12M) in MeOH (30 mL) was purge with nitrogen before the addition of Palladium carbon (38 mg, 0.18 mmol, 0.20 equiv). The flask was then vacuumed and flushed with hydrogen. The reaction mixture was hydrogenated at room temperature for 1 day under atmospheric pressure. It was then filtered through a Celite pad and the filtrate was concentrated and purified by Prep-HPLC to give the title compound as a brown solid (300 mg, 69%). 1H NMR (400 MHz, CDCl3) δ 12.51 (s, 1H), 8.30 (d, J=11.2 Hz, 2H), 7.67 (d, J=7.2 Hz, 1H), 7.57 (d, J=7.1 Hz, 1H), 7.36 (s, 1H), 7.24-7.11 (m, 2H), 6.73 (m, 1H), 5.71 (m, 1H), 4.73 (m, 1H), 4.20 (m, 1H), 3.76 (m, 1H), 3.57-3.33 (m, 4H), 3.05 (s, 3H), 2.21 (m, 1H), 2.09-1.81 (m, 3H), 1.65 (d, J=22.1 Hz, 3H).

Step 3: Chiral Separation

The mixture obtained in step 2 was first purified by chiral prep HPLC using a Chiralpak IB column, 2×25 cm, 5 um (hexane:EtOHOH, 50:50). The first eluting fraction contained two overlapped pics (retention time=9.3-9.7 min).

Third elution fraction: 3-(difluoromethyl)-N-[(2E)-1-[(2R)-2-fluoro-3-hydroxy-2-methylpropyl]-5-[(3R)-1-methyl-2-oxopiperidin-3-yl]-2,3-dihydro-1H-1,3-benzodiazol-2-ylidene]benzamide (3a)

55 mg, off white solid, retention time=19.7 min, mp: 2444-246 degrees Celcius.

Fourth eluting fraction: 3-(difluoromethyl)-N-[(2E)-1-[(2S)-2-fluoro-3-hydroxy-2-methylpropyl]-5-[(3S)-1-methyl-2-oxopiperidin-3-yl]-2,3-dihydro-1H-1,3-benzodiazol-2-ylidene]benzamide (3b)

55 mg, off white solid, retention time=33.3 min, mp: 102-104° C.

The first fraction was then separated using a Chiralpak IA, 2×25 cm, 5 um (DCM:MeOH, 20:80). First eluting fraction: 3-(difluoromethyl)-N-[(2E)-1-[(2S)-2-fluoro-3-hydroxy-2-methylpropyl]-5-[(3R)-1-methyl-2-oxopiperidin-3-yl]-2,3-dihydro-1H-1,3-benzodiazol-2-ylidene]benzamide (3c).

45 mg, brown solid, retention time=6.8 min, mp: 236-238° C.

Second elution fraction: 3-(difluoromethyl)-N-[(2E)-1-[(2R)-2-fluoro-3-hydroxy-2-methylpropyl]-5-[(3S)-1-methyl-2-oxopiperidin-3-yl]-2,3-dihydro-1H-1,3-benzodiazol-2-ylidene]benzamide (3d)

45 mg, brown solid, retention time=9.7 min, mp: 104-106° C.

Example 4: (E)-N-(1-(3-hydroxypropyl)-5-(1-methyl-2-oxo-1,2-dihydropyridin-3-yl)-1H-benzo[d]imidazol-2(3H)-ylidene)-3-(trifluoromethyl)benzamide (4)

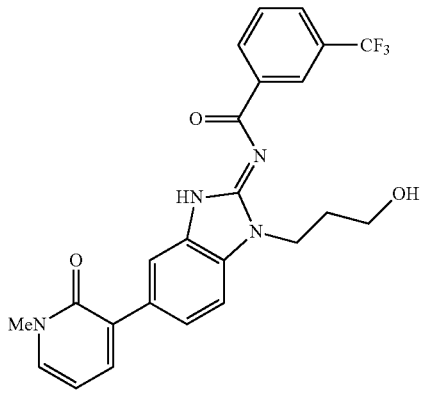 [SMILES: Cn1cccc(-c2ccc3c(c2)[nH]/c(=N\C(=O)c2cccc(C(F)(F)F)c2)n3CCCO)c1=O]

Prepared in an analogous fashion to Example 1, but using Intermediate 3 (1 eq.) in place of Intermediate 2 in step 1. ESI⁺: M+1: 471. ¹H NMR (300 MHz, CDCl₃) δ 12.46 (s, 1H), 8.55-8.39 (m, 2H), 7.83-7.45 (m, 5H), 7.42-7.22 (m, 2H), 6.36-6.23 (m, 1H), 4.70 (s, 1H), 4.52-4.48 (s, 2H), 3.65 (s, 3H), 3.48-3.44 (m, 2H), 2.05-2.03 (m, 2H).

Example 5: (E)-N-(1-(3-hydroxypropyl)-5-(1-methyl-6-oxo-1,6-dihydropyrimidin-5-yl)-1H-benzo[d]imidazol-2(3H)-ylidene)-3-(trifluoromethyl)benzamide (5)

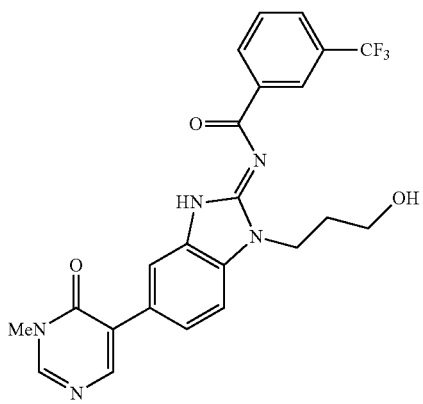 [SMILES: Cn1cncc(-c2ccc3c(c2)[nH]/c(=N\C(=O)c2cccc(C(F)(F)F)c2)n3CCCO)c1=O]

Prepared in an analogous fashion to Example 1, but using Intermediate 5 (1 eq.) in place of Intermediate 2 in step 1. ESI⁺: M+1: 472. ¹H NMR (300 MHz, CDCl₃) δ 12.46 (s, 1H), 8.54-8.39 (m, 2H), 8.26 (s, 1H), 8.12 (s, 1H), 7.82-7.79 (m, 2H), 7.62-7.59 (m, 2H), 7.46 (d, J=7.6 Hz, 1H), 4.50 (br s, 2H), 3.66 (s, 3H), 3.55 (br s, 2H), 3.37 (s, 1H), 2.10 (br s, 2H).

Example 6: (E)-N-(5-(1,4-dimethyl-2-oxo-1,2-dihydropyridin-3-yl)-1-(3-hydroxypropyl)-1H-benzo[d]imidazol-2(3H)-ylidene)-3-(trifluoromethyl)benzamide (6)

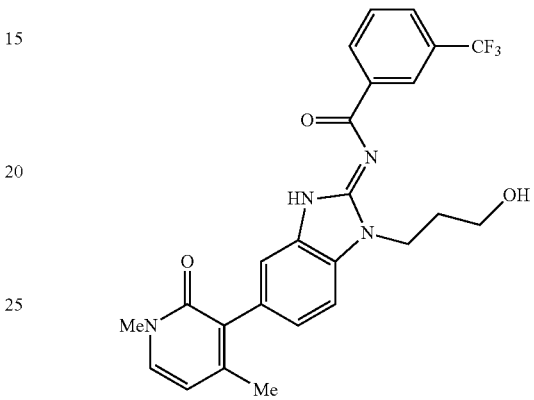

Prepared in an analogous fashion to Example 1, but using Intermediate 6 (1 eq.) in place of Intermediate 2 in step 1. ESI⁺: M+1: 485. ¹H NMR (300 MHz, DMSO-d₆) δ 12.82 (s, 1H), 8.59-8.49 (m, 2H), 7.91 (d, J=7.7 Hz, 1H), 7.74 (t, J=7.7 Hz, 1H), 7.62-7.57 (m, 2H), 7.37 (d, J=1.4 Hz, 1H), 7.09 (dd, J=8.2, 1.6 Hz, 1H), 6.22 (d, J=7.0 Hz, 1H), 4.72 (t, J=5.1 Hz, 1H), 4.37 (t, J=6.9 Hz, 2H), 3.51 (t, J=5.8 Hz, 2H), 3.44 (s, 3H), 2.52-2.24 (m, 2H), 1.99 (s, 3H).

Example 7: (E)-N-(5-(1-(cyclopropylmethyl)-2-oxopiperidin-3-yl)-1-(3-hydroxypropyl)-1H-benzo[d]imidazol-2(3H)-ylidene)-3-(trifluoromethyl)benzamide (7)

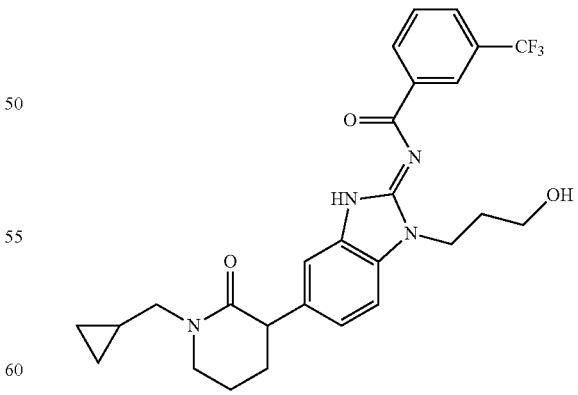

Prepared in an analogous fashion to Example 1, but using Intermediate 4 (1 eq.) in place of Intermediate 2 in step 1. ESI⁺: M+1: 515. ¹H NMR (300 MHz, DMSO-d₆) δ 12.77 (s, 1H), 8.57-8.47 (m, 2H), 7.97-7.85 (m, 1H), 7.73 (t, J=7.7 Hz, 1H), 7.46 (d, J=8.3 Hz, 1H), 7.37 (d, J=1.5 Hz, 1H), 7.10

(dd, J=8.3, 1.6 Hz, 1H), 4.68 (t, J=5.1 Hz, 1H), 4.33 (t, J=6.8 Hz, 2H), 3.72-3.67 (m, 1H), 3.60-3.32 (m, 4H), 3.11 (dd, J=13.6, 7.0 Hz, 1H), 2.10 (s, 1H), 1.96 (t, J=7.7 Hz, 1H), 1.91-1.81 (m, 5H), 0.55-0.43 (m, 2H), 0.28-0.22 (m, 2H).

Example 8: (E)-N-(1-(3-hydroxypropyl)-5-(2-oxocyclohexyl)-1H-benzo[d]imidazol-2(3H)-ylidene)-3-(trifluoromethyl)benzamide (8)

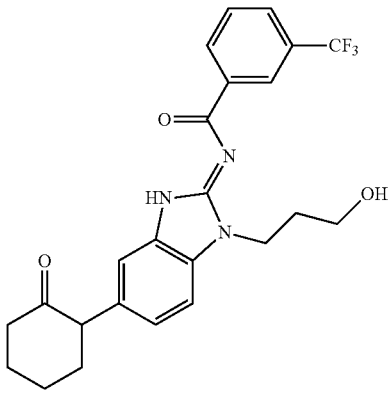 [SMILES: O=C(/N=c1\[nH]c2cc(C3CCCCC3=O)ccc2n1CCCO)c1cccc(C(F)(F)F)c1]

Step 1: (Z)-3-(5-(2-oxocyclohexyl)-2-((3-(trifluoromethyl)benzoyl)imino)-3-((2-(trimethylsilyl)ethoxy)methyl)-2,3-dihydro-1H-benzo[d]imidazol-1-yl)propyl acetate In a glass reaction vessel equipped with a Teflon-coated screw cap was dissolved Intermediate 1-CF$_3$ (1 eq.), (cyclohex-1-en-1-yloxy)trimethylsilane (2 eq.), tributyl(fluoro)stannane (2 eq.), and Pd(P(Bu)$_3$)$_2$ (0.06 eq.) in benzene (0.28 M). The resulting solution was then de-oxygenated via sub-surface purging for 5 min before the vessel was tightly sealed and heated at 90° C. for 18 h. The volatiles were removed in vacuo and the resulting residue was partitioned between water and ether. The aqueous layer was separated and back-extracted with ether. The combined organic extracts were washed further with 1 N aq. NaOH, water and brine, dried over Na$_2$SO$_4$, filtered and the filtrate concentrated in vacuo. Purification by way of column chromatography (SiO$_2$, gradient elution, 1:1 (v/v) Hex:EtOAc→EtOAc) furnished the desired product compound as a viscous oil (28% yield).

Step 2: (E)-3-(5-(2-oxocyclohexyl)-2-((3-(trifluoromethyl)benzoyl)imino)-2,3-dihydro-1H-benzo[d]imidazol-1-yl)propyl acetate In a glass RBF equipped with a Teflon-coated magnetic stirrer was dissolved (Z)-3-(5-(2-oxocyclohexyl)-2-((3-(trifluoromethyl)benzoyl)imino)-3-((2-(trimethylsilyl)ethoxy)methyl)-2,3-dihydro-1H-benzo[d]imidazol-1-yl)propyl acetate (1 eq.) from the previous step in dichloromethane (0.1 M). To this was then added trifluoroacetic acid (50 eq.) neat and drop-wise over a period of 1 min. The resulting mixture was allowed to stir at RT for 14 h. The crude reaction mixture was diluted with EtOAc and washed sequentially with sat. aq. NaHCO$_3$, water and brine. The organic extract was then dried over MgSO$_4$, filtered and the filtrate concentrated in vacuo. Purification by way of column chromatography (SiO$_2$, gradient elution, 1:1 (v/v) Hex:EtOAc→EtOAc→10:1 (v/v) EtOAc:MeOH) furnished the desired product compound (76% yield).

Step 3: (E)-N-(1-(3-hydroxypropyl)-5-(2-oxocyclohexyl)-1H-benzo[d]imidazol-2(3H)-ylidene)-3-(trifluoromethyl)benzamide In a glass RBF equipped with a Teflon-coated magnetic stirrer was dissolved (E)-3-(5-(2-oxocyclohexyl)-2-((3-(trifluoromethyl)benzoyl)imino)-2,3-dihydro-1H-benzo[d]imidazol-1-yl)propyl acetate (1 eq.) from the previous step in methanol (0.021 M). To this was then added potassium carbonate (2 eq.) and the resulting suspension was stirred at RT for 4 h. The volatiles were then removed in vacuo and the resulting residue was partitioned between 10% aq. NaHCO$_3$ and EtOAc. The aqueous layer was separated and back-extracted with EtOAc. The combined organic extracts were washed further with water and brine, dried over Na$_2$SO$_4$, filtered and the filtrate concentrated in vacuo. Purification by way of high-pressure liquid chromatography (Cis, gradient elution, 4:1 (v/v) H$_2$O:MeCN+0.1% TFA→MeCN+0.1% TFA) furnished the title compound as a white solid (37% yield). ESI$^+$: M+1: 460. $^1$H NMR (300 MHz, CDCl$_3$) δ 12.54 (s, 1H), 8.52 (s, 1H), 8.44 (dd, J=7.8 Hz, 1H), 7.75 (d, J=7.7 Hz, 1H), 7.58 (t, J=7.7 Hz, 1H), 7.33-7.23 (m, 1H), 7.17-7.04 (m, 2H), 4.53-4.42 (m, 2H), 3.67 (dd, J=12.1, 5.3 Hz, 1H), 3.48 (t, J=5.5 Hz, 2H), 2.62-2.39 (m, 2H), 2.36-2.11 (m, 2H), 2.10-1.69 (m, 7H).

Example 9: (E)-N-(1-(3-hydroxypropyl)-5-(5-oxo-2,5-dihydrofuran-3-yl)-1H-benzo[d]imidazol-2(3H)-ylidene)-3-(trifluoromethyl)benzamide (9)

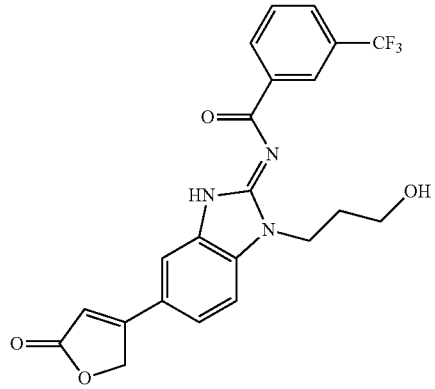 [SMILES: O=C1C=C(c2ccc3c(c2)[nH]/c(=N\C(=O)c2cccc(C(F)(F)F)c2)n3CCCO)CO1]

In a glass RBF equipped with a Teflon-coated magnetic stirrer was dissolved 3-trifluoromethyl-benzoic acid (1.5 eq.), HBTU (1.1 eq.) and ethyl-diisopropyl-amine (3 eq.) in acetonitrile (0.12 M). To this was then added Intermediate 7 (1 eq.) as a solution (0.12 M) in 9:1 (v/v) DMF: MeCN and the resulting yellow solution was allowed to stir at RT for 1 h. The crude reaction mixture was directly subjected to purification by way of column chromatography (SiO$_2$, gradient elution, CH$_2$Cl$_2$→9:1 (v/v) CH$_2$Cl$_2$:MeOH). The product thus obtained can then be triturated in methanol and ether to furnish the title compound as a white solid (21% yield). ESI$^+$: M+1: 446. $^1$H NMR (300 MHz, DMSO-d$_6$) δ 12.94 (s, 1H), 8.58-8.48 (m, 2H), 7.92 (d, J=7.6 Hz, 1H), 7.79-7.66 (m, 4H), 6.66 (s, 1H), 5.43 (s, 2H), 4.71-4.65 (m, 1H), 4.40-4.34 (m, 2H), 3.51-3.44 (m, 2H), 2.01-1.94 (m, 2H).

Example 10: (E)-N-(1-(3-hydroxypropyl)-5-(1-methyl-5-oxopyrrolidin-3-yl)-1H-benzo[d]imidazol-2(3H)-ylidene)-3-(trifluoromethyl)benzamide (10)

Example 11: (E)-N-(5-(3-hydroxyoxetan-3-yl)-1-(3-hydroxypropyl)-1H-benzo[d]imidazol-2(3H)-ylidene)-3-(trifluoromethyl)benzamide (11)

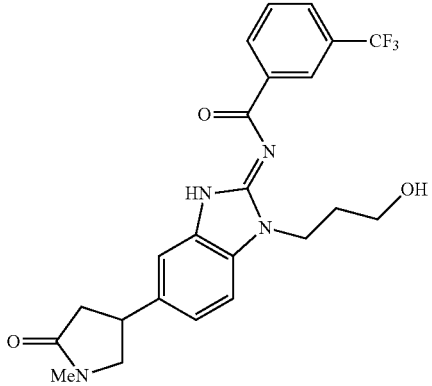 [SMILES: CN1CC(c2ccc3c(c2)[nH]/c(=N\C(=O)c2cccc(C(F)(F)F)c2)n3CCCO)CC1=O]

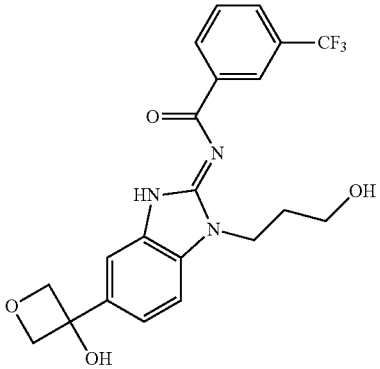 [SMILES: O=C(/N=c1\[nH]c2cc(C3(O)COC3)ccc2n1CCCO)c1cccc(C(F)(F)F)c1]

Step 1: (E)-N-(1-(3-hydroxypropyl)-5-(1-methyl-5-oxo-2,5-dihydro-1H-pyrrol-3-yl)-1H-benzo[d]imidazol-2(3H)-ylidene)-3-(trifluoromethyl)benzamide In a glass RBF equipped with a Teflon-coated magnetic stirrer was dissolved Example 9 (1 eq.) in methylamine (100 eq., 40% (w/v) aqueous solution). The resulting reaction mixture was allowed to stir at RT for 16 h. The volatiles were then removed in vacuo and the resulting residue was directly subjected to column chromatography (SiO$_2$, gradient elution, 4:1 (v/v) Hex:EtOAc→EtOAc→5:1 (v/v) EtOAc:MeOH) to furnish the desired product as a white solid (12% yield).

Step 2: (E)-N-(1-(3-hydroxypropyl)-5-(1-methyl-5-oxopyrrolidin-3-yl)-1H-benzo[d]imidazol-2(3H)-ylidene)-3-(trifluoromethyl)benzamide In a glass RBF equipped with a Teflon-coated magnetic stirrer was suspended (E)-N-(1-(3-hydroxypropyl)-5-(1-methyl-5-oxo-2,5-dihydro-1H-pyrrol-3-yl)-1H-benzo[d]imidazol-2(3H)-ylidene)-3-(trifluoromethyl)benzamide (1 eq.) from the previous step and palladium(II) chloride (0.5 eq.) in MeOH (0.01 M). The resulting suspension was sub-surface purged with hydrogen for 30 min and then stirred under a static balloon atmosphere of hydrogen for 3 days. The insoluble were then removed via filtration through a bed of methanol-wetted celite. The insoluble were rinsed further with methanol and the filtrate thus obtained was concentrated in vacuo. The residue thus obtained was then directly subjected to purification by way of column chromatography (SiO$_2$, gradient elution, 4:1 (v/v) Hex:EtOAc→EtOAc→10:1 (v/v) EtOAc:MeOH) to furnish the desired product as a white solid (81% yield). ESI$^+$: M+1: 461. $^1$H NMR (300 MHz, DMSO-d$_6$) δ 12.94 (s, 1H), 8.56-8.47 (m, 2H), 7.90 (d, J=8.1 Hz, 1H), 7.74 (t, J=7.7 Hz, 1H), 7.57-7.38 (m, 2H), 7.30-7.21 (m, 1H), 4.33 (t, J=6.8 Hz, 2H), 3.84-3.72 (m, 1H), 3.72-3.59 (m, 1H), 3.47 (t, J=6.2 Hz, 2H), 3.35 (dd, J=9.2, 6.6 Hz, 1H), 2.80 (s, 3H), 2.76-2.65 (m, 1H), 2.41-2.28 (m, 1H), 2.01-1.90 (m, 2H).

Step 1: (Z)-3-(5-(3-hydroxyoxetan-3-yl)-2-((3-(trifluoromethyl)benzoyl)imino)-3-((2-(trimethylsilyl)ethoxy)methyl)-2,3-dihydro-1H-benzo[d]imidazol-1-yl)propyl acetate In a glass RBF equipped with a Teflon-coated magnetic stirrer was dissolved Intermediate 1-CF$_3$ (1 eq.) in THF (0.05 M). To this was then added at 0° C., isopropylmagnesium chloride (1 eq., 2.9 M solution in 2-MeTHF) dropwise over a period of 5 min. The resulting reaction mixture was allowed to stir at 0° C. for 15 min and then at RT for 30 min. After re-cooling to 0° C., oxetan-3-one (1.2 eq.) was then added neat and drop-wise over 5 min. The reaction mixture was then allowed to warm slowly to RT over 1 h. The reaction was quenched with the addition of 1 N aq. HCl and then extracted with EtOAc. The combined organic extracts were then washed further with 10% aq. NaHCO$_3$ and brine, dried over Na$_2$SO$_4$, filtered and the filtrate concentrated in vacuo. Further purification by way of column chromatography (SiO$_2$, gradient elution, EtOAc→10:1 (v/v) EtOAc:MeOH) furnished the desired product as a white solid (21% yield).

Step 2: (E)-3-(5-(3-hydroxyoxetan-3-yl)-2-((3-(trifluoromethyl)benzoyl)imino)-2,3-dihydro-1H-benzo[d]imidazol-1-yl)propyl acetate In a glass RBF equipped with a Teflon-coated magnetic stirrer was dissolved (Z)-3-(5-(3-hydroxyoxetan-3-yl)-2-((3-(trifluoromethyl)benzoyl)imino)-3-((2-(trimethylsilyl)ethoxy)methyl)-2,3-dihydro-1H-benzo[d]imidazol-1-yl)propyl acetate (1 eq.) from the previous step in dichloroethane (0.02 M). To this was then added TFA (50 eq.) neat and drop-wise over a period of 1 min. The resulting mixture was allowed to stir at RT for 18 h. The crude reaction mixture was then diluted with DCM and washed sequentially with sat. aq. NaHCO$_3$, water and brine. The organic extract was then dried over Na$_2$SO$_4$ and filtered. Concentration of the filtrate in vacuo furnished the desired product compound as an off-white solid.

Step 3: (E)-N-(5-(3-hydroxyoxetan-3-yl)-1-(3-hydroxypropyl)-1H-benzo[d]imidazol-2(3H)-ylidene)-3-(trifluoromethyl)benzamide In a glass RBF equipped with a Teflon-coated magnetic stirrer was dissolved (E)-3-(5-(3-hydroxyoxetan-3-yl)-2-

((3-(trifluoromethyl)benzoyl)imino)-2,3-dihydro-1H-benzo[d]imidazol-1-yl)propyl acetate (1 eq.) from the previous step in methanol (0.02 M). To this was then added potassium carbonate (2 eq.) and the resulting suspension was stirred at RT for 18 h. The volatiles were then removed in vacuo and the resulting residue was directly subjected to purification by way of high pressure liquid chromatography (Cis, gradient elution, 9:1 (v/v)→1:9 (v/v) H$_2$O:MeCN+0.1% TFA). The title compound was isolated as a white solid (49% yield over 2 steps). ESI$^+$: M+1: 436. $^1$H NMR (300 MHz, DMSO-d$_6$) δ 12.83 (s, 1H), 8.57-8.47 (m, 2H), 7.90 (d, J=7.8 Hz, 1H), 7.81 (s, 1H), 7.73 (t, J=7.5 Hz, 1H), 7.60-7.53 (m, 2H), 6.50-6.42 (m, 1H), 4.84-4.77 (m, 2H), 4.74-4.64 (m, 3H), 4.38-4.31 (m, 2H), 3.52-3.43 (m, 2H), 2.02-1.91 (m, 2H).

Example 12: (E)-N-(5-(1-acetylpyrrolidin-3-yl)-1-(3-hydroxypropyl)-1H-benzo[d]imidazol-2(3H)-ylidene)-3-(trifluoromethyl)benzamide (12)

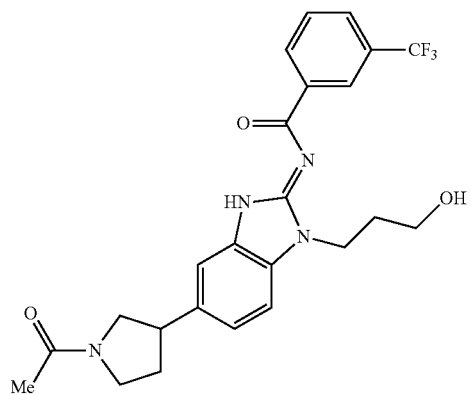 [SMILES: CC(=O)N1CCC(c2ccc3c(c2)[nH]/c(=N\C(=O)c2cccc(C(F)(F)F)c2)n3CCCO)C1]

Step 1: (Z)-tert-butyl 4-(1-(3-acetoxypropyl)-2-((3-(trifluoromethyl)benzoyl)imino)-3-((2-(trimethylsilyl)ethoxy)methyl)-2,3-dihydro-1H-benzo[d]imidazol-5-yl)-2,3-dihydro-1H-pyrrole-1-carboxylate In a glass RBF equipped with a Teflon-coated magnetic stirrer was dissolved Intermediate 8-CF$_3$ (1 eq.), tert-butyl 4-(((trifluoromethyl)sulfonyl)oxy)-2,3-dihydro-1H-pyrrole-1-carboxylate (1 eq.), Pd(dppf)Cl$_2$ (0.2 eq.) and potassium phosphate (3 eq.) in a 10:1 (v/v) solution (0.075 M) of THF:water. The reaction mixture thus obtained was then thoroughly deoxygenated via sub-surface purging with nitrogen for 15 min. The vessel was then sealed and stirred at RT for 18 h. The reaction was quenched with the addition of water and extracted with EtOAc. The combined organic extracts were then washed further with 10% aq. NaHCO$_3$ and brine, dried over Na$_2$SO$_4$, filtered and the filtrate concentrated in vacuo. Further purification by way of column chromatography (SiO$_2$, gradient elution, 10:1 (v/v) Hex:EtOAc→EtOAc→10:1 (v/v) EtOAc:MeOH) furnished the desired product (58% yield).

Step 2: (Z)-tert-butyl 3-(1-(3-acetoxypropyl)-2-((3-(trifluoromethyl)benzoyl)imino)-3-((2-(trimethylsilyl)ethoxy)methyl)-2,3-dihydro-1H-benzo[d]imidazol-5-yl)pyrrolidine-1-carboxylate In a glass RBF equipped with a Teflon-coated magnetic stirrer was suspended palladium (0.2 eq., dry, 10% w/w over carbon) and (Z)-tert-butyl 4-(1-(3-acetoxypropyl)-2-((3-(trifluoromethyl)benzoyl)imino)-3-((2-(trimethylsilyl)ethoxy)methyl)-2,3-dihydro-1H-benzo[d]imidazol-5-yl)-2,3-dihydro-1H-pyrrole-1-carboxylate (1 eq.) from the previous step in methanol (0.05 M). The resulting suspension was evacuated and back-filled with nitrogen (3×) and then hydrogen (3×). The reaction suspension was then stirred under a static balloon-maintained hydrogen atmosphere for 18 h. The reaction was quenched with dichloromethane and the resulting suspension was filtered through a pad of dichloromethane-wetted celite. The filtrate thus obtained was concentrated in vacuo and subjected to column chromatography (SiO$_2$, gradient elution, 10:1 (v/v) Hex:EtOAc→EtOAc→10:1 (v/v) EtOAc:MeOH). The desired product was isolated as a colorless oil (88% yield).

Step 3: (E)-3-(5-(pyrrolidin-3-yl)-2-((3-(trifluoromethyl)benzoyl)imino)-2,3-dihydro-1H-benzo[d]imidazol-1-yl)propyl acetate In a glass RBF equipped with a Teflon-coated magnetic stirrer was dissolved (Z)-tert-butyl 3-(1-(3-acetoxypropyl)-2-((3-(trifluoromethyl)benzoyl)imino)-3-((2-(trimethylsilyl)ethoxy)methyl)-2,3-dihydro-1H-benzo[d]imidazol-5-yl)pyrrolidine-1-carboxylate (1 eq.) from the previous step in dichloroethane (0.1 M). To this solution was then added TFA (30 eq.) neat and drop-wise over a period of 1 min. The resulting mixture was allowed to stir at RT for 8 h. The crude reaction mixture was then diluted with DCM and washed sequentially with sat. aq. NaHCO$_3$, water and brine. The organic extract was then dried over Na$_2$SO$_4$ and filtered. Concentration of the filtrate in vacuo furnished the desired product compound as a viscous oil.

Step 4: (E)-3-(5-(1-acetylpyrrolidin-3-yl)-2-((3-(trifluoromethyl)benzoyl)imino)-2,3-dihydro-1H-benzo[d]imidazol-1-yl)propyl acetate In a glass RBF equipped with a Teflon-coated magnetic stirrer was dissolved (E)-3-(5-(pyrrolidin-3-yl)-2-((3-(trifluoromethyl)benzoyl)imino)-2,3-dihydro-1H-benzo[d]imidazol-1-yl)propyl acetate (1 eq.) from the previous step in pyridine (0.1 M). To this solution was then added acetic anhydride (1.8 eq.) neat and drop-wise over a period of 1 min. The resulting mixture was then allowed to stir at RT for 48 h. The crude reaction mixture was then diluted with EtOAc and washed sequentially with sat. aq. NH$_4$Cl, water and brine. The organic extract was then dried over Na$_2$SO$_4$ and filtered The filtrate thus obtained was concentrated in vacuo and subjected to column chromatography (SiO$_2$, gradient elution, 10:1 (v/v) Hex:EtOAc→EtOAc→10:1 (v/v) EtOAc:MeOH). The desired product was isolated as a pale yellow oil (38% yield over two steps).

Step 5: (E)-N-(5-(1-acetylpyrrolidin-3-yl)-1-(3-hydroxypropyl)-1H-benzo[d]imidazol-2(3H)-ylidene)-3-(trifluoromethyl)benzamide In a glass RBF equipped with a Teflon-coated magnetic stirrer was dissolved (E)-3-(5-(1-acetylpyrrolidin-3-yl)-2-((3-(trifluoromethyl)benzoyl)imino)-2,3-dihydro-1H-benzo[d]imidazol-1-yl)propyl acetate (1 eq.) from the previous step in methanol (0.02 M). To this was then added potassium carbonate (2 eq.) and the resulting suspension was stirred at RT for 8 h. The volatiles were then removed in vacuo and the resulting residue was directly subjected to column chromatography (SiO$_2$, gradient elution, 10:1 (v/v) Hex:EtOAc→EtOAc→10:1 (v/v) EtOAc:MeOH). The title compound was isolated as a white solid (95% yield). ESI$^+$: M+1: 475. $^1$H NMR (300 MHz, CDCl$_3$) δ 12.61 (s, 1H), 8.53 (s, 1H), 8.45 (d, J=7.8 Hz, 1H), 7.75 (d, J=7.8 Hz, 1H), 7.58 (t, J=7.8 Hz, 1H), 7.34-7.13 (m, 3H), 4.67-4.60 (m, 1H), 4.47 (t, J=5.4 Hz, 2H), 4.06-3.71 (m, 2H), 3.70-3.27 (m, 2H), 3.70-3.27 (m, 5H), 2.38-2.21 (m, 1H), 2.15-1.78 (m, 6H).

Example 13: (E)-N-(5-(1-acetylpiperidin-4-yl)-1-(3-hydroxypropyl)-1H-benzo[d]imidazol-2(3H)-ylidene)-3-(trifluoromethyl)benzamide (13)

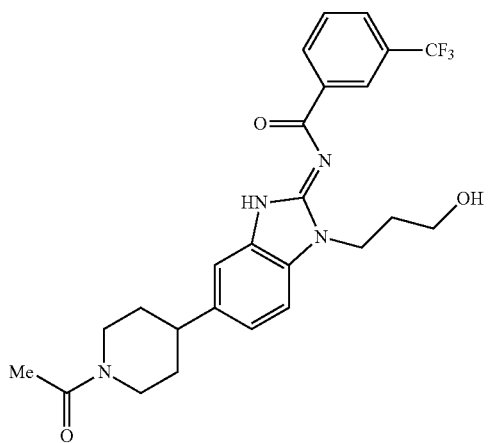 [SMILES: CC(=O)N1CCC(c2ccc3c(c2)[nH]/c(=N\C(=O)c2cccc(C(F)(F)F)c2)n3CCCO)CC1]

Prepared in an analogous fashion to Example 12, but using tert-butyl 4-(((trifluoromethyl)sulfonyl)oxy)-5,6-dihydropyridine-1(2H)-carboxylate (1 eq.) in place of tert-butyl 4-(((trifluoromethyl)sulfonyl)oxy)-2,3-dihydro-1H-pyrrole-1-carboxylate in step 1. ESI+: M+1: 489. $^1$H NMR (300 MHz, CDCl$_3$) δ 12.51 (s, 1H), 8.51 (s, 1H), 8.43 (d, J=7.7 Hz, 1H), 7.75 (d, J=7.7 Hz, 1H), 7.58 (t, J=7.8 Hz, 1H), 7.33-7.12 (m, 3H), 4.80 (d, J=13.3 Hz, 1H), 4.72-4.65 (m, 1H), 4.47 (t, J=5.8 Hz, 2H), 3.95 (t, J=13.4 Hz, 1H), 3.51-3.45 (m, 2H), 3.18 (t, J=12.8 Hz, 1H), 2.82 (s, 1H), 2.63 (t, J=12.9 Hz, 1H), 2.15 (s, 3H), 2.05 (d, J=5.9 Hz, 2H), 1.96-1.82 (m, 2H), 1.73-1.54 (m, 2H).

Example 14: (E)-N-(5-(1-acetylpiperidin-3-yl)-1-(3-hydroxypropyl)-1H-benzo[d]imidazol-2(3H)-ylidene)-3-(trifluoromethyl)benzamide (14)

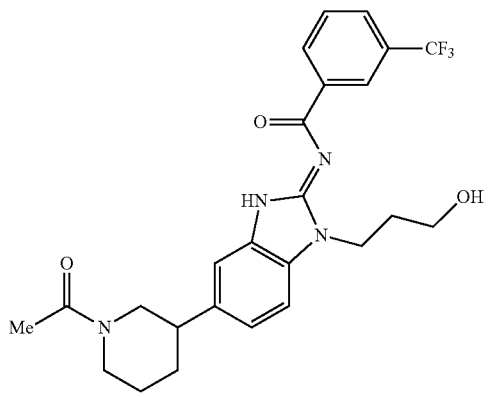 [SMILES: CC(=O)N1CCCC(c2ccc3c(c2)[nH]/c(=N\C(=O)c2cccc(C(F)(F)F)c2)n3CCCO)C1]

Prepared in an analogous fashion to Example 12, but using tert-butyl 5-(((trifluoromethyl)sulfonyl)oxy)-3,4-dihydropyridine-1(2H)-carboxylate (1 eq.) in place of tert-butyl 4-(((trifluoromethyl)sulfonyl)oxy)-2,3-dihydro-1H-pyrrole-1-carboxylate in step 1. ESI+: M+1: 489. $^1$H NMR (300 MHz, CDCl$_3$) δ 12.55 (s, 1H), 8.53 (s, 1H), 8.45 (d, J=7.8 Hz, 1H), 7.75 (d, J=7.8 Hz, 1H), 7.58 (t, J=7.8 Hz, 1H), 7.34-7.16 (m, 3H), 4.79-4.54 (m, 2H), 4.48 (dd, J=5.5, 4.8 Hz, 2H), 3.85 (t, J=13.5 Hz, 1H), 3.51-3.45 (m, 2H), 3.08-2.99 (m, 1H), 2.78-2.71 (m, 1H), 2.56-2.49 (m, 1H), 2.18-1.98 (m, 5H), 1.92-1.54 (m, 4H).

Example 15: (E)-N-(5-(8-acetyl-8-azabicyclo[3.2.1]octan-3-yl)-1-(3-hydroxypropyl)-1H-benzo[d]imidazol-2(3H)-ylidene)-3-(trifluoromethyl)benzamide (15)

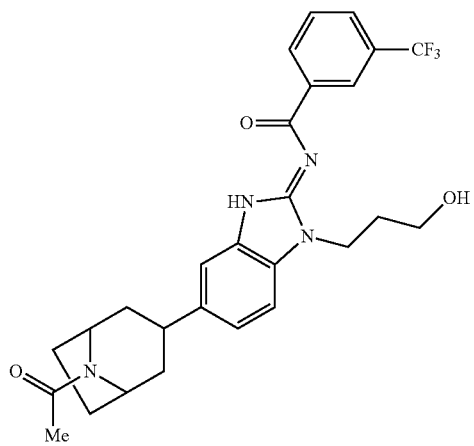 [SMILES: CC(=O)N1C2CCC1CC(c1ccc3c(c1)[nH]/c(=N\C(=O)c1cccc(C(F)(F)F)c1)n3CCCO)C2]

Prepared in an analogous fashion to Example 12, but using tert-butyl 3-(((trifluoromethyl)sulfonyl)oxy)-8-azabicyclo[3.2.1]oct-3-ene-8-carboxylate (1 eq.) in place of tert-butyl 4-(((trifluoromethyl)sulfonyl)oxy)-2,3-dihydro-1H-pyrrole-1-carboxylate in step 1. ESI+: M+1: 515. $^1$H NMR (300 MHz, CDCl$_3$) δ 12.50 (s, 1H), 8.51 (s, 1H), 8.44 (d, J=7.7 Hz, 1H), 7.75 (d, J=7.7 Hz, 1H), 7.58 (t, J=7.8 Hz, 1H), 7.30-7.15 (m, 3H), 4.82-4.66 (m, 2H), 4.47 (t, J=5.9 Hz, 2H), 4.26-4.16 (m, 1H), 3.52-3.45 (m, 2H), 2.80-2.40 (m, 2H), 2.20-1.44 (m, 12H).

Example 16: (E)-N-(1-((S)-2-fluoro-3-hydroxy-2-methylpropyl)-5-(1-methyl-2-oxopiperidin-3-yl)-1H-benzo[d]imidazol-2(3H)-ylidene)-3-(trifluoromethyl)benzamide (16)

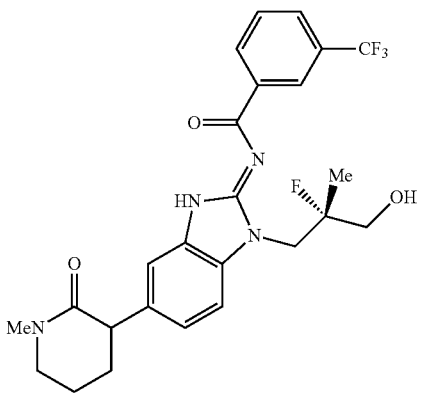 [SMILES: CN1CCCC(c2ccc3c(c2)[nH]/c(=N\C(=O)c2cccc(C(F)(F)F)c2)n3C[C@](C)(F)CO)C1=O]

Prepared in an analogous fashion to Example 1, but using Intermediate 9 (1 eq.) in place of Intermediate 2 in step 1. ESI+: M+1: 507. ¹H NMR (300 MHz, CDCl₃) δ 12.45 (s, 1H), 8.45 (s, 1H), 8.35 (d, J=7.9 Hz, 1H), 7.76 (d, J=7.9 Hz, 1H), 7.59 (t, J=7.7 Hz, 1H), 7.43-7.30 (m, 1H), 7.28-7.13 (m, 2H), 5.69-5.59 (m, 1H), 4.71 (dd, J=32.5, 15.4 Hz, 1H), 4.28-4.13 (m, 1H), 3.76 (t, J=7.3 Hz, 1H), 3.65-3.32 (m, 4H), 3.06 (s, 3H), 2.26-2.19 (m, 1H), 2.12-1.82 (m, 3H), 1.65 (d, J=22.2 Hz, 3H).

Example 17: N-[1-But-3-enyl-5-(1-methyl-2-oxo-pyrrolidin-3-yl)-1,3-dihydro-benzoimidazol-(2E)-ylidene]-3-trifluoromethyl-benzamide (17)

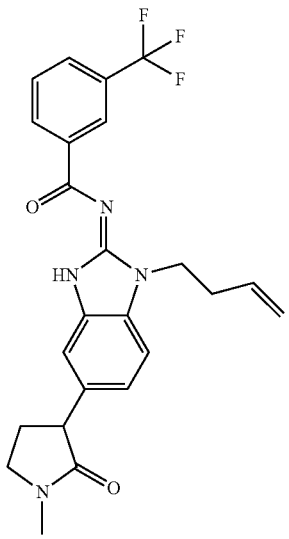 [SMILES: C=CCCn1/c(=N/C(=O)c2cccc(C(F)(F)F)c2)[nH]c2cc(C3CCN(C)C3=O)ccc21]

A mixture of 3-(2-Amino-1-but-3-enyl-1H-benzoimidazol-5-yl)-1-methyl-pyrrolidin-2-one hydrobromide (Intermediate 11, 300 mg; 0.82 mmol; 1.0 eq.), 3-(trifluoromethyl)benzoic acid (Aldrich, 163 mg; 0.86 mmol; 1.05 eq.), (Benzotriazol-1-yloxy)tris(dimethylamino)phosphonium hexafluorophosphate (449 mg; 0.99 mmol; 1.2 eq.) and diisopropylethylamine (358 µl; 2.05 mmol; 2.5 eq.) in DMF (2 mL) was stirred at rt for 1 h. The reaction mixture was poured into water. The precipitate was collected by filtration and then washed with water to give the crude product, which was purified by prep-HPLC to yield the tile compound as a white solid (89% yield). ESI+: M+1: 457. 1H NMR (400 MHz, DMSO-d6) δ 2.69 (s, 1H), 8.52 (dt, J=4.3, 1.8 Hz, 2H), 7.90 (d, J=7.8 Hz, 1H), 7.74 (t, J=7.9 Hz, 1H), 7.51 (d, J=8.3 Hz, 1H), 7.42 (d, J=1.6 Hz, 1H), 7.14 (dd, J=8.3, 1.7 Hz, 1H), 5.90 (ddt, J=17.1, 10.2, 6.8 Hz, 1H), 5.13-4.90 (m, 2H), 4.35 (t, J=7.0 Hz, 2H), 3.71 (t, J=8.9 Hz, 1H), 3.53-3.39 (m, 2H), 2.83 (s, 3H), 2.62 (p, J=6.8 Hz, 2H), 2.49-2.42 (m, 1H), 2.13-1.92 (m, 1H).

Example 18: N-[1-But-3-enyl-5-(1-methyl-2-oxo-piperidin-3-yl)-1,3-dihydro-benzoimidazol-(2E)-ylidene]-3-trifluoromethyl-benzamide (18)

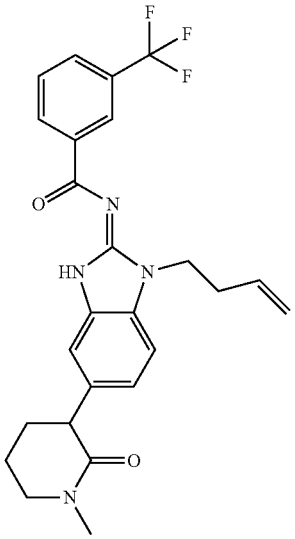 [SMILES: C=CCCn1/c(=N/C(=O)c2cccc(C(F)(F)F)c2)[nH]c2cc(C3CCCN(C)C3=O)ccc21]

The title compound was prepared in an analogous fashion to Example 17 by using 3-(2-Amino-1-but-3-enyl-1H-benzoimidazol-5-yl)-1-methyl-piperidin-2-one (Intermediate 12) in place of 3-(2-Amino-1-but-3-enyl-1H-benzoimidazol-5-yl)-1-methyl-pyrrolidin-2-one hydrobromide (88% yield). ESI+: M+1: 471. 1H NMR (400 MHz, DMSO-d6) δ 12.68 (s, 1H), 8.57-8.45 (m, 2H), 7.89 (d, J=7.8 Hz, 1H), 7.74 (t, J=7.7 Hz, 1H), 7.48 (d, J=8.3 Hz, 1H), 7.36 (d, J=1.6 Hz, 1H), 7.09 (dd, J=8.3, 1.7 Hz, 1H), 5.90 (ddt, J=17.0, 10.2, 6.9 Hz, 1H), 5.08 (dq, J=17.2, 1.6 Hz, 1H), 5.00 (ddt, J=10.3, 2.1, 1.1 Hz, 1H), 4.35 (t, J=7.0 Hz, 2H), 3.67 (dd, J=8.4, 5.9 Hz, 1H), 3.52-3.39 (m, 1H), 3.42-3.32 (m, 1H), 2.91 (s, 3H), 2.61 (q, J=6.9 Hz, 2H), 2.13-2.08 (m, 1H), 1.96-1.76 (m, 3H).

Example 19: N-[1-Allyl-5-(1-methyl-2-oxo-pyrrolidin-3-yl)-1,3-dihydro-benzoimidazol-(2E)-ylidene]-3-trifluoromethyl-benzamide (19)

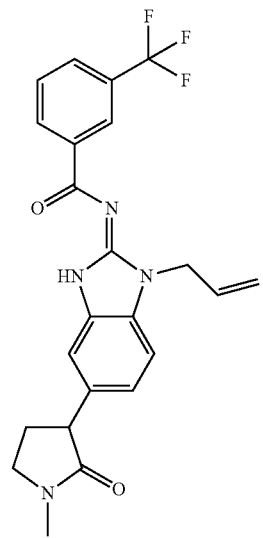 [SMILES: C=CCn1/c(=N/C(=O)c2cccc(C(F)(F)F)c2)[nH]c2cc(C3CCN(C)C3=O)ccc21]

The title compound was prepared in an analogous fashion to Example 17 by using 3-(1-Allyl-2-amino-1H-benzoimidazol-5-yl)-1-methyl-pyrrolidin-2-one hydrobromide (Intermediate 13) in place of 3-(2-Amino-1-but-3-enyl-1H-benzoimidazol-5-yl)-1-methyl-pyrrolidin-2-one hydrobromide (83% yield). ESI⁺: M+1: 443. 1H NMR (400 MHz, DMSO-d6) δ 12.77 (s, 1H), 8.52 (d, J=7.8 Hz, 1H), 8.49 (s, 1H), 7.93-7.86 (m, 1H), 7.74 (t, J=7.8 Hz, 1H), 7.44 (d, J=1.7 Hz, 1H), 7.41 (d, J=8.3 Hz, 1H), 7.13 (dd, J=8.3, 1.7 Hz, 1H), 6.04 (ddt, J=17.1, 10.5, 5.4 Hz, 1H), 5.29-5.13 (m, 2H), 5.01-4.85 (m, 2H), 3.72 (t, J=8.9 Hz, 1H), 3.55-3.36 (m, 2H), 2.83 (s, 3H), 2.55-2.46 (m, 1H), 2.02 (dtd, J=12.7, 8.7, 7.6 Hz, 1H).

Example 20: N-[1-(2,3-Dihydroxy-propyl)-5-(1-methyl-2-oxo-pyrrolidin-3-yl)-1,3-dihydro-benzoimidazol-(2E)-ylidene]-3-trifluoromethyl-benzamide

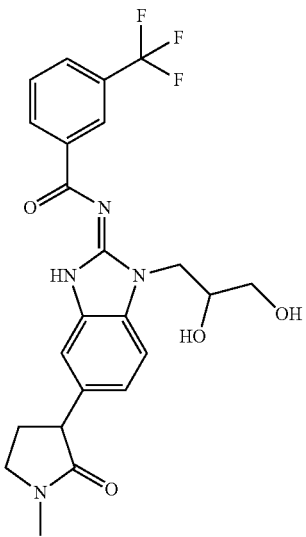 [SMILES: CN1CCC(c2ccc3c(c2)[nH]/c(=N\C(=O)c2cccc(C(F)(F)F)c2)n3CC(O)CO)C1=O]

To a stirring solution of N-[1-Allyl-5-(1-methyl-2-oxo-pyrrolidin-3-yl)-1,3-dihydro-benzoimidazol-(2E)-ylidene]-3-trifluoromethyl-benzamide (example 19, 30 mg; 0.07 mmol; 1.0 eq.) in acetone (5 mL) and water (0.6 mL), was added osmium tetroxide (2.5 wt % in t-BuOH, 0.13 mL; 0.01 mmol; 0.15 eq.) and 4-methylmorpholine n-oxide (15 mg; 0.14 mmol; 2.0 eq.). The resulting mixture was stirred at rt overnight. The crude was purified by prep-HPLC to afford the title product as a white solid (56% yield). ESI⁺: M+1: 477. 1H NMR (400 MHz, DMSO-d6) δ 12.72 (s, 1H), 8.63-8.42 (m, 2H), 7.89 (d, J=7.7 Hz, 1H), 7.73 (t, J=7.7 Hz, 1H), 7.49 (d, J=8.3 Hz, 1H), 7.42 (d, J=1.7 Hz, 1H), 7.12 (dd, J=8.3, 1.7 Hz, 1H), 5.08 (d, J=5.2 Hz, 1H), 4.85 (t, J=5.6 Hz, 1H), 4.41 (dd, J=14.0, 4.1 Hz, 1H), 4.25-4.10 (m, 1H), 4.08-3.95 (m, 1H), 3.71 (t, J=8.9 Hz, 1H), 3.53-3.38 (m, 4H), 2.83 (s, 3H), 2.55-2.48 (m, 1H), 2.12-1.94 (m, 1H).

Example 20a and 20b: N-[1-(2,3-Dihydroxy-propyl)-5-((S)-1-methyl-2-oxo-pyrrolidin-3-yl)-1,3-dihydro-benzoimidazol-(2E)-ylidene]-3-trifluoromethyl-benzamide (20a) and N-[1-(2,3-Dihydroxy-propyl)-5-((R)-1-methyl-2-oxo-pyrrolidin-3-yl)-1,3-dihydro-benzoimidazol-(2E)-ylidene]-3-trifluoromethyl-benzamide (20b)

Two diastereoisomers of example 20 were separated by chiral SFC (CHIRALPAK OJ-H, 4.6×250 mm, 5 μm column, isocratic 55% MeOH, 8 mL/min, 100 Bar CO₂ 40° C.).

First eluting isomer (20a): 21 mg of a pink solid, retention time: 3.44 min. ESI⁺ (M+1): 477. 1H NMR (400 MHz, DMSO-d6) δ 12.76 (s, 1H), 8.61-8.43 (m, 2H), 7.89 (d, J=7.7 Hz, 1H), 7.73 (t, J=7.7 Hz, 1H), 7.49 (d, J=8.3 Hz, 1H), 7.42 (d, J=1.6 Hz, 1H), 7.12 (dd, J=8.4, 1.6 Hz, 1H), 5.07 (d, J=5.3 Hz, 1H), 4.85 (t, J=5.7 Hz, 1H), 4.41 (dd, J=14.0, 4.0 Hz, 1H), 4.16 (dd, J=14.0, 7.4 Hz, 1H), 4.08-3.92 (m, 1H), 3.71 (t, J=8.9 Hz, 1H), 3.55-3.37 (m, 4H), 2.83 (s, 3H), 2.49-2.40 (m, 1H), 2.12-1.93 (m, 1H).

Second eluting isomer (20b): 20 mg of a pink solid, retention time: 5.42 min. ESI⁺ (M+1): 477. 1H NMR (400 MHz, DMSO-d6) δ 12.75 (s, 1H), 8.60-8.45 (m, 2H), 7.89 (d, J=7.7 Hz, 1H), 7.73 (t, J=7.7 Hz, 1H), 7.49 (d, J=8.3 Hz, 1H), 7.42 (d, J=1.6 Hz, 1H), 7.12 (dd, J=8.4, 1.7 Hz, 1H), 5.08 (d, J=5.3 Hz, 1H), 4.85 (t, J=5.7 Hz, 1H), 4.41 (dd, J=13.8, 4.0 Hz, 1H), 4.22-4.11 (m, 1H), 4.01 (q, J=5.6 Hz, 1H), 3.71 (t, J=8.9 Hz, 1H), 3.54-3.37 (m, 4H), 2.83 (s, 3H), 2.50-2.44 (m, 1H), 2.11-1.93 (m, 1H).

Example 21: N-[1-(3,4-Dihydroxy-butyl)-5-(1-methyl-2-oxo-pyrrolidin-3-yl)-1,3-dihydro-benzoimidazol-(2E)-ylidene]-3-trifluoromethyl-benzamide (21)

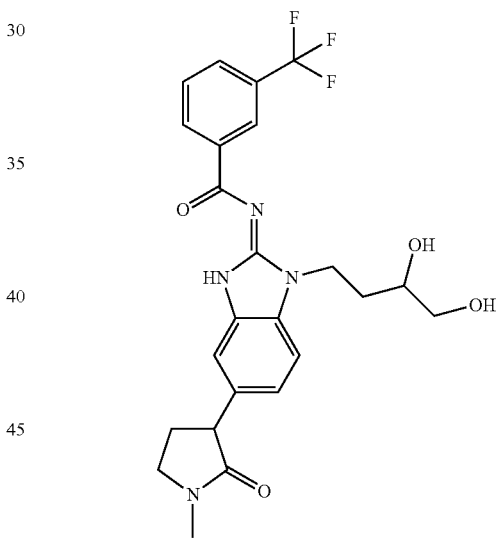

The title was prepared in an analogous fashion to Example 20 by using N-[1-But-3-enyl-5-(1-methyl-2-oxo-pyrrolidin-3-yl)-1,3-dihydro-benzoimidazol-(2E)-ylidene]-3-trifluoromethyl-benzamide in place of N-[1-Allyl-5-(1-methyl-2-oxo-pyrrolidin-3-yl)-1,3-dihydro-benzoimidazol-(2E)-ylidene]-3-trifluoromethyl-benzamide (74% yield). ESI⁺: M+1: 491. 1H NMR (400 MHz, DMSO-d6) δ 12.65 (bs, 1H), 8.58-8.46 (m, 2H), 7.94-7.85 (m, 1H), 7.74 (t, J=7.7 Hz, 1H), 7.49 (d, J=8.3 Hz, 1H), 7.43 (d, J=1.6 Hz, 1H), 7.15 (dt, J=8.4, 1.6 Hz, 1H), 4.76 (d, J=4.9 Hz, 1H), 4.52 (t, J=5.7 Hz, 1H), 4.42-4.32 (m, 2H), 3.72 (t, J=8.9 Hz, 1H), 3.53-3.44 (m, 2H), 3.44-3.34 (m, 2H), 3.29-3.21 (m, 1H), 2.83 (s, 3H), 2.54-2.46 (m, 1H), 2.07-1.98 (m, 2H), 1.80-1.66 (m, 1H).

Example 21a, 21b, 21c and 21d: N-[1-((S)-3,4-Dihydroxy-butyl)-5-((R)-1-methyl-2-oxo-pyrrolidin-3-yl)-1,3-dihydro-benzoimidazol-(2E)-ylidene]-3-trifluoromethyl-benzamide (21a), N-[1-((R)-3,4-Dihydroxy-butyl)-5-((R)-1-methyl-2-oxo-pyrrolidin-3-yl)-1,3-dihydro-benzoimidazol-(2E)-ylidene]-3-trifluoromethyl-benzamide (21b), N-[1-((R)-3,4-Dihydroxy-butyl)-5-((S)-1-methyl-2-oxo-pyrrolidin-3-yl)-1,3-dihydro-benzoimidazol-(2E)-ylidene]-3-trifluoromethyl-benzamide (21c) and N-[1-((S)-3,4-Dihydroxy-butyl)-5-((S)-1-methyl-2-oxo-pyrrolidin-3-yl)-1,3-dihydro-benzoimidazol-(2E)-ylidene]-3-trifluoromethyl-benzamide (21d)

The four diastereoisomers of example 21 were separated by chiral SFC. A first purification using a CHIRALPAK OJ-H column (4.6×250 mm, 5 m column, isocratic 30% MeOH, 8 mL/min, 100 Bar $CO_2$ 40° C.) allowed the separation of three fractions:

First eluting fraction: 38 mg of a off-white powder. Contains a racemic mixture.

Second eluting fraction (21a): 18 mg of a off white powder, retention time: 14.02 min ESI$^+$ (M+1): 491. $^1$H NMR (400 MHz, DMSO-$d_6$) δ 12.74 (s, 1H), 8.57-8.48 (m, 2H), 7.90 (d, J=7.7 Hz, 1H), 7.74 (t, J=7.7 Hz, 1H), 7.49 (d, J=8.4 Hz, 1H), 7.44 (t, J=1.6 Hz, 1H), 7.15 (dt, J=8.4, 1.6 Hz, 1H), 4.76 (d, J=4.9 Hz, 1H), 4.53 (t, J=5.3 Hz, 1H), 4.45-4.29 (m, 2H), 3.72 (t, J=8.9 Hz, 1H), 3.53-3.45 (m, 2H), 3.44-3.35 (m, 2H), 3.29-3.25 (m, 1H), 2.83 (s, 3H), 2.54-2.50 (m, 1H), 2.12-1.95 (m, 2H), 1.80-1.66 (m, 1H).

Third eluting fraction (21b): 9 mg of a off-white powder, retention time: 17.01 min. ESI$^+$ (M+1): 491. 1H NMR (400 MHz, DMSO-d6) δ 12.74 (s, 1H), 8.57-8.49 (m, 2H), 7.93-7.86 (m, 1H), 7.74 (t, J=7.7 Hz, 1H), 7.49 (d, J=8.3 Hz, 1H), 7.44 (d, J=1.6 Hz, 1H), 7.15 (dd, J=8.4, 1.7 Hz, 1H), 4.76 (d, J=4.9 Hz, 1H), 4.53 (t, J=5.6 Hz, 1H), 4.46-4.29 (m, 2H), 3.72 (t, J=8.9 Hz, 1H), 3.53-3.43 (m, 2H), 3.42-3.33 (m, 2H), 3.30-3.25 (m, 1H), 2.83 (s, 3H), 2.60-2.46 (m, 1H), 2.10-1.97 (m, 2H), 1.79-1.67 (m, 1H).

The first eluting fraction was separated using a CHIRALPAK IA column (10×250 mm, 5 μm column, isocratic 60% MeOH with 0.5% DMEA, 8 mL/min, 100 Bar $CO_2$ 35° C.).

First eluting fraction (21c): 10 mg of a white powder, retention time: 5.32 min ESI$^+$ (M+1): 491. 1H NMR (400 MHz, DMSO-d6) δ 12.66 (s, 1H), 8.57-8.48 (m, 2H), 7.89 (d, J=7.7 Hz, 1H), 7.73 (t, J=7.7 Hz, 1H), 7.49 (d, J=8.2 Hz, 1H), 7.43 (d, J=1.5 Hz, 1H), 7.15 (dd, J=8.3, 1.7 Hz, 1H), 4.76 (d, J=4.8 Hz, 1H), 4.52 (t, J=5.7 Hz, 1H), 4.44-4.29 (m, 2H), 3.72 (t, J=8.9 Hz, 1H), 3.50-3.44 (m, 2H), 3.43-3.35 (m, 2H), 3.29-3.17 (m, 1H), 2.83 (s, 3H), 2.57-2.43 (m, 1H), 2.11-1.94 (m, 2H), 1.81-1.65 (m, 1H).

Second eluting fraction (21d): 14 mg of a white powder, retention time: 6.69 min ESI$^+$ (M+1): 491. 1H NMR (400 MHz, DMSO-d6) δ 12.54 (s, 1H), 8.57-8.48 (m, 2H), 7.89 (d, J=7.7 Hz, 1H), 7.73 (t, J=7.7 Hz, 1H), 7.48 (d, J=8.3 Hz, 1H), 7.43 (d, J=1.5 Hz, 1H), 7.14 (dd, J=8.3, 1.7 Hz, 1H), 4.77 (bs, 1H), 4.53 (bs, 1H), 4.45-4.28 (m, 2H), 3.72 (t, J=8.9 Hz, 1H), 3.54-3.45 (m, 2H), 3.43-3.37 (m, 2H), 3.26-3.21 (m, 1H), 2.83 (s, 3H), 2.52-2.43 (m, 1H), 2.13-1.94 (m, 2H), 1.79-1.65 (m, 1H).

Example 22: N-[1-(3,4-Dihydroxy-butyl)-5-(1-methyl-2-oxo-piperidin-3-yl)-1,3-dihydro-benzoimidazol-(2E)-ylidene]-3-trifluoromethyl-benzamide (22)

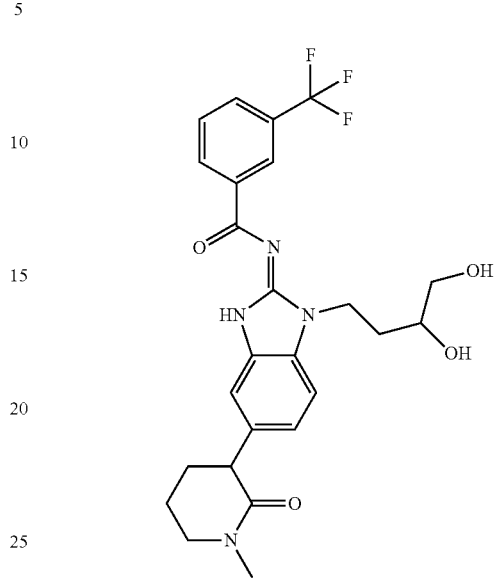

The title was prepared in an analogous fashion to Example 20 by using N-[1-But-3-enyl-5-(1-methyl-2-oxo-piperidin-3-yl)-1,3-dihydro-benzoimidazol-(2E)-ylidene]-3-trifluoromethyl-benzamide in place of N-[1-Allyl-5-(1-methyl-2-oxo-pyrrolidin-3-yl)-1,3-dihydro-benzoimidazol-(2E)-ylidene]-3-trifluoromethyl-benzamide (80% yield). ESI$^+$: M+1: 505. 1H NMR (400 MHz, DMSO-d6) δ 12.65 (s, 1H), 8.59-8.47 (m, 2H), 7.89 (dd, J=7.7, 1.7 Hz, 1H), 7.73 (t, J=7.7 Hz, 1H), 7.45 (d, J=8.3 Hz, 1H), 7.38 (d, J=1.6 Hz, 1H), 7.10 (dt, J=8.3, 1.5 Hz, 1H), 4.78 (bs, 1H), 4.52 (t, J=5.7 Hz, 1H), 4.44-4.28 (m, 2H), 3.68 (dd, J=8.4, 5.9 Hz, 1H), 3.55-3.42 (m, 2H), 3.42-3.35 (m, 2H), 3.29-3.23 (m, 1H), 2.91 (s, 3H), 2.19-1.99 (m, 2H), 1.99-1.79 (m, 3H), 1.79-1.64 (m, 1H).

Examples 22a, 22b, 22c and 22d: N-[1-((R)-3,4-Dihydroxy-butyl)-5-((S)-1-methyl-2-oxo-piperidin-3-yl)-1,3-dihydro-benzoimidazol-(2E)-ylidene]-3-trifluoromethyl-benzamide (22a), N-[1-((S)-3,4-Dihydroxy-butyl)-5-((S)-1-methyl-2-oxo-piperidin-3-yl)-1,3-dihydro-benzoimidazol-(2E)-ylidene]-3-trifluoromethyl-benzamide (22b), N-[1-((R)-3,4-Dihydroxy-butyl)-5-((R)-1-methyl-2-oxo-piperidin-3-yl)-1,3-dihydro-benzoimidazol-(2E)-ylidene]-3-trifluoromethyl-benzamide (22c) and N-[1-((S)-3,4-Dihydroxy-butyl)-5-((R)-1-methyl-2-oxo-piperidin-3-yl)-1,3-dihydro-benzoimidazol-(2E)-ylidene]-3-trifluoromethyl-benzamide (22d)

The four diastereoisomers of example 22 were separated by chiral SFC (CHIRALPAK IA, 10×250 mm, 5 m column, isocratic 60% MeOH with 0.5% DMEA, 8 mL/min, 100 Bar $CO_2$ 35° C.).

First eluting fraction (22a): 12 mg of a white solid, retention time: 4.97 min. ESI$^+$ (M+1): 505. 1H NMR (400 MHz, DMSO-d6) δ 12.70 (s, 1H), 8.57-8.48 (m, 2H), 7.89 (d, J=7.7 Hz, 1H), 7.73 (t, J=7.7 Hz, 1H), 7.45 (d, J=8.3 Hz, 1H), 7.38 (d, J=1.6 Hz, 1H), 7.10 (dd, J=8.3, 1.7 Hz, 1H), 4.77 (d, J=5.0 Hz, 1H), 4.53 (t, J=5.7 Hz, 1H), 4.45-4.28 (m, 2H), 3.67 (dd, J=8.5, 5.8 Hz, 1H), 3.54-3.38 (m, 2H), 3.42-3.31 (m, 2H), 3.33-3.22 (m, 1H), 2.91 (s, 3H), 2.17-1.98 (m, 2H), 1.97-1.81 (m, 3H), 1.86-1.65 (m, 1H).

Second eluting fraction (22b): 14 mg of a white powder, retention time: 6.41 min ESI⁺ (M+1): 505. 1H NMR (400 MHz, DMSO-d6) δ 12.70 (s, 1H), 8.57-8.48 (m, 2H), 7.92-7.85 (m, 1H), 7.73 (t, J=7.7 Hz, 1H), 7.45 (d, J=8.3 Hz, 1H), 7.38 (d, J=1.6 Hz, 1H), 7.10 (dd, J=8.3, 1.6 Hz, 1H), 4.78 (d, J=4.9 Hz, 1H), 4.53 (t, J=5.6 Hz, 1H), 4.45-4.28 (m, 2H), 3.67 (dd, J=8.4, 5.8 Hz, 1H), 3.52-3.33 (m, 4H), 3.30-3.21 (m, 1H), 2.91 (s, 3H), 2.17-1.99 (m, 2H), 1.97-1.77 (m, 3H), 1.79-1.65 (m, 1H).

Third eluting fraction (22c): 10 mg of a white powder, retention time: 6.98 min ESI⁺ (M+1): 505. 1H NMR (400 MHz, DMSO-d6) δ 12.70 (s, 1H), 8.57-8.48 (m, 2H), 7.89 (d, J=7.7 Hz, 1H), 7.73 (t, J=7.7 Hz, 1H), 7.45 (d, J=8.3 Hz, 1H), 7.38 (d, J=1.6 Hz, 1H), 7.10 (dd, J=8.3, 1.7 Hz, 1H), 4.79 (bs, 1H), 4.53 (bs, 1H), 4.41-4.30 (m, 2H), 3.67 (dd, J=8.4, 5.9 Hz, 1H), 3.53-3.42 (m, 2H), 3.47-3.34 (m, 2H), 3.28-3.17 (m, 1H), 2.91 (s, 3H), 2.17-1.98 (m, 2H), 1.97-1.65 (m, 3H), 1.33-1.14 (m, 1H).

Fourth eluting fraction (22d): 12 mg of a white powder, retention time: 8.15 min ESI⁺ (M+1): 505. 1H NMR (400 MHz, DMSO-d6) δ 12.71 (s, 1H), 8.57-8.48 (m, 2H), 7.89 (dt, J=7.9, 1.3 Hz, 1H), 7.73 (t, J=7.7 Hz, 1H), 7.45 (d, J=8.3 Hz, 1H), 7.38 (d, J=1.5 Hz, 1H), 7.10 (dd, J=8.3, 1.7 Hz, 1H), 4.78 (bs, 1H), 4.54 (bs, 1H), 4.41-4.30 (m, 2H), 3.67 (dd, J=8.5, 5.8 Hz, 1H), 3.53-3.34 (m, 4H), 3.27-3.18 (m, 1H), 2.91 (s, 3H), 2.14-2.00 (m, 2H), 1.97-1.65 (m, 4H).

Example 23: N-[1-(3-hydroxypropyl)-5-(1-methyl-2-oxopyrrolidin-3-yl)-1H-1,3-benzodiazol-2-yl]-3-(trifluoromethyl)benzamide (23)

Step 1: N-(1-{3-[(tert-butyldimethylsilyl)oxy]propyl}-5-(1-methyl-2-oxopyrrolidin-3-yl)-1H-1,3-benzodiazol-2-yl)-3-(trifluoromethyl)benzamide

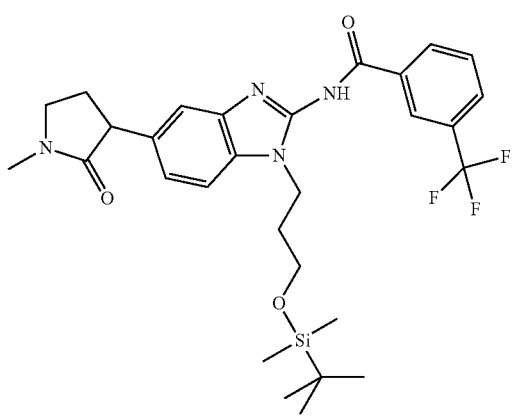 [SMILES: CN1CCC(c2ccc3c(c2)nc(NC(=O)c2cccc(C(F)(F)F)c2)n3CCCO[Si](C)(C)C(C)(C)C)C1=O]

A solution of 3-(trifluoromethyl)benzoic acid (68 mg, 0.36 mmol, 1.00 equiv), HOBT (58 mg, 0.43 mmol, 1.20 equiv), EDCI (82 mg, 0.43 mmol, 1.20 equiv), DIEA (138 mg, 1.07 mmol, 3.00 equiv) and 3-(2-amino-1-[3-[(tert-butyldimethylsilyl)oxy]propyl]-1H-1,3-benzodiazol-5-yl)-1-methylpyrrolidin-2-one (Intermediate 11, 150 mg, 0.36 mmol, 1.00 equiv) in DMF (2 mL) was stirred for 1 overnight at room temperature. It was then diluted with EtOAc and washed with sat. NH4Cl (2×50 mL) and brine (2×50 mL). Organic phase was dried over anhydrous sodium sulfate, filtered and concentrated to afford the title compound as a brown solid (240 mg, 82%). ESI⁺ (M+1): 575.3.

Step 2: N-[1-(3-hydroxypropyl)-5-(1-methyl-2-oxopyrrolidin-3-yl)-1H-1,3-benzodiazol-2-yl]-3-(trifluoromethyl)benzamide

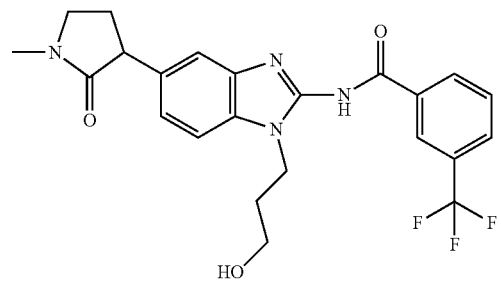 [SMILES: CN1CCC(c2ccc3c(c2)nc(NC(=O)c2cccc(C(F)(F)F)c2)n3CCCO)C1=O]

A solution of N-(1-[3-[(tert-butyldimethylsilyl)oxy]propyl]-5-(1-methyl-2-oxopyrrolidin-3-yl)-1H-1,3-benzodiazol-2-yl)-3-(trifluoromethyl)benzamide (240 mg, 0.29 mmol, 1.00 equiv) and TBAF (306 mg, 1.17 mmol, 4.00 equiv) in THF (4 mL) was stirred for 3 h at room temperature. It was then diluted with EtOAc (60 mL) and washed with satNH4Cl (3×60 mL) and brine (60 mL). Organic phase was dried over anhydrous sodium sulfate, filtered and concentrated. Purification by Prep-HPLC afforded the title compound as a pink solid (110 mg, 81%). ESI⁺: (M+1): 461.2. ¹H NMR (400 MHz, CDCl₃) δ 12.48 (s, 1H), 8.53 (s, 1H), 8.46-8.44 (d, J=8, 1H), 7.78-7.76 (d, J=8, 1H), 7.62-7.58 (m, 1H), 7.31-7.28 (m, 2H), 7.25-7.23 (m, 1H), 4.71 (s, 1H), 4.50-4.47 (m, 2H), 3.80-3.75 (m, 1H), 3.53-3.46 (m, 4H), 2.98 (s, 3H), 2.64-2.56 (m, 1H), 2.20-2.13 (m, 1H), 2.10-2.01 (m, 2H).

Example 23a and 23b: N-[1-(3-hydroxypropyl)-5-[(3S)-1-methyl-2-oxopyrrolidin-3-yl]-1H-1,3-benzodiazol-2-yl]-3-(trifluoromethyl)benzamide (23a) and N-[1-(3-hydroxypropyl)-5-[(3R)-1-methyl-2-oxopyrrolidin-3-yl]-1H-1,3-benzodiazol-2-yl]-3-(trifluoromethyl) benzamide (23b)

The two enantiomers of N-[1-(3-hydroxypropyl)-5-(1-methyl-2-oxopyrrolidin-3-yl)-1H-1,3-benzodiazol-2-yl]-3-(trifluoromethyl)benzamide (60 mg) were separated by Chiral-Prep-HPLC (CHIRALPAK-AD-H-SL002, 20×250 mm column; hexane:EtOH, 50:50). First eluting fraction: 23a, 21 mg of a white solid, second elution fraction: 23b, 21 mg of a white solid. mp: 161-164° C.

Example 24: 3-(difluoromethyl)-N-[1-(3-hydroxypropyl)-5-(1-methyl-2-oxopyrrolidin-3-yl)-1H-1,3-benzodiazol-2-yl]benzamide (24)

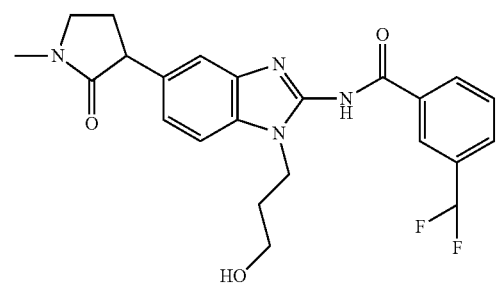 [SMILES: CN1CCC(c2ccc3c(c2)nc(NC(=O)c2cccc(C(F)F)c2)n3CCCO)C1=O]

The title compound was obtained following procedure described for example 23 but using 3-(difluoromethyl)benzoic acid (Enamine, 41 mg, 0.24 mmol. 1 equiv) in place of 3-(trifluoromethyl)benzoic acid as a white solid. ESI+: M+1: 443.2. 1H NMR (400 MHz, CDCl3) δ 12.52 (s, 1H), 8.39-8.37 (m, 2H), 7.69-7.67 (d, J=8, 1H), 7.59-7.55 (m, 1H), 7.30-7.27 (m, 2H), 7.24-7.21 (m, 1H), 6.89-6.61 (m, 1H), 4.82 (s, 1H), 4.49-4.46 (m, 2H), 3.77-3.73 (m, 1H), 3.51-3.45 (m, 4H), 2.97 (s, 3H), 2.61-2.53 (m, 1H), 2.18-2.08 (m, 1H), 2.04-2.00 (m, 2H). mp: 166.0-168.0° C.

Example 25: N-[1-(3-Hydroxy-propyl)-5-(1,4,4-trimethyl-5-oxo-pyrrolidin-3-yl)-1H-benzoimidazol-2-yl]-3-trifluoromethyl-benzamide (25)

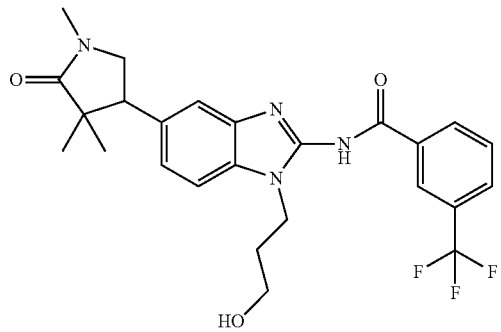 [SMILES: CN1CC(c2ccc3c(c2)nc(NC(=O)c2cccc(C(F)(F)F)c2)n3CCCO)C(C)(C)C1=O]

The title compound was obtained following procedure described for example 23, step 1 but starting from 4-[2-amino-1-(3-hydroxypropyl)-1H-1,3-benzodiazol-5-yl]-1,3,3-trimethylpyrrolidin-2-one (100 mg, 0.28 mmol, 1.00 equiv) and 3-(trifluoromethyl)benzoic acid (57 mg, 0.28 mmol, 1.00 equiv) as a (30 mg, 21%). 1H NMR (300 MHz, CDCl3) δ: 12.50 (s, 1H), 8.52 (s, 1H), 8.44 (d, J=7.8 Hz, 1H), 7.77 (d, J=7.7 Hz, 1H), 7.60 (t, J=7.7 Hz, 1H), 7.30 (d, J=8.3 Hz, 1H), 7.26-7.21 (m, 1H), 7.17 (dd, J=8.4, 1.5 Hz, 1H), 4.50 (t, J=6.0 Hz, 3H), 3.67-3.57 (m, 2H), 3.53 (t, J=5.5 Hz, 2H), 3.35 (t, J=7.9 Hz, 1H), 2.99 (s, 3H), 2.08 (p, J=5.7 Hz, 2H), 1.27 (s, 3H), 0.77 (s, 3H). ESI+ (M+1): 489.3. mp: 104-106 OC.

Examples 25a and 25b: N-[1-(3-hydroxypropyl)-5-[(3S)-1,4,4-trimethyl-5-oxopyrrolidin-3-yl]-1H-1,3-benzodiazol-2-yl]-3-(trifluoromethyl)benzamide (25a) and N-[1-(3-hydroxypropyl)-5-[(3R)-1,4,4-trimethyl-5-oxopyrrolidin-3-yl]-1H-1,3-benzodiazol-2-yl]-3-(trifluoromethyl)benzamide (25b)

The two enantiomers of N-[1-(3-Hydroxy-propyl)-5-(1,4,4-trimethyl-5-oxo-pyrrolidin-3-yl)-1H-benzoimidazol-2-yl]-3-trifluoromethyl-benzamide were separated by chiral prep HPLC (column IA, 21.2×250 mm, 5 micron, hexane:EtOH, 50:50).

First eluting fraction: 25a, 34 mg of a white solid, mp: 90-91 OC, Second elution fraction: 25b, 30 mg of a white solid. mp: 88-89° C.

Example 26: 3-Difluoromethyl-N-[1-(2-fluoro-3-hydroxy-2-methyl-propyl)-5-(4-methyl-3-oxo-morpholin-2-yl)-1H-benzoimidazol-2-yl]-benzamide (26)

Step 1: N-{1-[3-(benzyloxy)-2-fluoro-2-methylpropyl]-5-(4-methyl-3-oxomorpholin-2-yl)-1H-1,3-benzodiazol-2-yl}-3-(difluoromethyl)benzamide

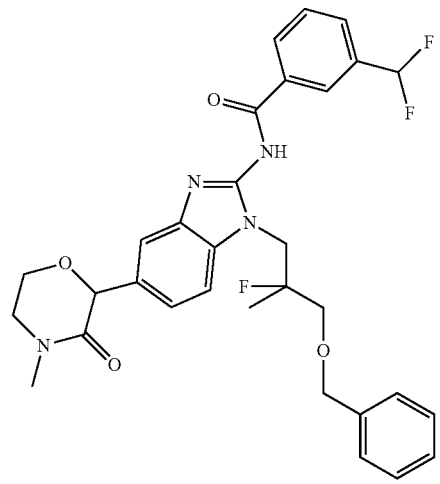 [SMILES: CN1CCOC(c2ccc3c(c2)nc(NC(=O)c2cccc(C(F)F)c2)n3CC(C)(F)COCc2ccccc2)C1=O]

The title compound was obtained following procedure described for example 23, step 1 but starting from 3-(difluoromethyl)benzoic acid (83.5 mg, 0.49 mmol, 1.27 equiv) and 2-[2-amino-1-[3-(benzyloxy)-2-fluoro-2-methylpropyl]-1H-1,3-benzodiazol-5-yl]-4-methylmorpholin-3-one (intermediate 16, 245 mg, 0.38 mmol, 1.00 equiv) as a red solid (200 mg, 86%).

Step 2: 3-Difluoromethyl-N-[1-(2-fluoro-3-hydroxy-2-methyl-propyl)-5-(4-methyl-3-oxo-morpholin-2-yl)-1H-benzoimidazol-2-yl]-benzamide

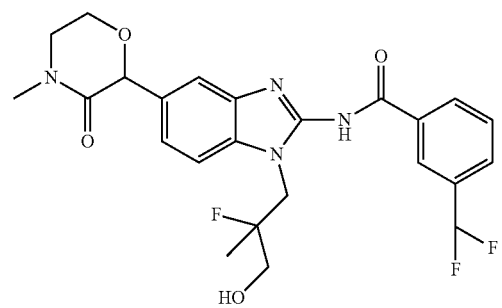 [SMILES: CN1CCOC(c2ccc3c(c2)nc(NC(=O)c2cccc(C(F)F)c2)n3CC(C)(F)CO)C1=O]

A degassed suspension of N-[1-[3-(benzyloxy)-2-fluoro-2-methylpropyl]-5-(4-methyl-3-oxomorpholin-2-yl)-1H-1,3-benzodiazol-2-yl]-3-(difluoromethyl)benzamide (80 mg, 0.13 mmol, 1.00 equiv) and Palladium carbon (8.06 mg, 0.07 mmol, 0.55 equiv) in MeOH (8.00 mL) was hydrogenated under atmosphere pressure of hydrogen O/N at RT. The solids were filtered out and the filtrate was concentrated and purified by Prep-HPLC to afford the title compound as a white solid (20 mg, 30%). 1H NMR (300 MHz, DMSO) δ 12.87 (d, J=7.9 Hz, 1H), 8.40 (d, J=7.5 Hz, 2H), 7.83-7.53

(m, 3H), 7.43 (d, J=7.5 Hz, 1H), 7.36-6.93 (m, 2H), 5.37 (t, J=6.1 Hz, 1H), 5.19 (s, 1H), 4.72-4.39 (m, 2H), 4.04-3.84 (m, 2H), 3.61 (ddt, J=17.2, 10.6, 6.7 Hz, 3H), 2.93 (s, 3H), 1.32 (d, J=22.2 Hz, 3H). ESI+ (M+1): 491.3. mp: 118-120° C.

Example 27: 3-Difluoromethyl-N-[1-(3-hydroxy-propyl)-5-(1,4,4-trimethyl-5-oxo-pyrrolidin-3-yl)-1H-benzoimidazol-2-yl]-benzamide (27)

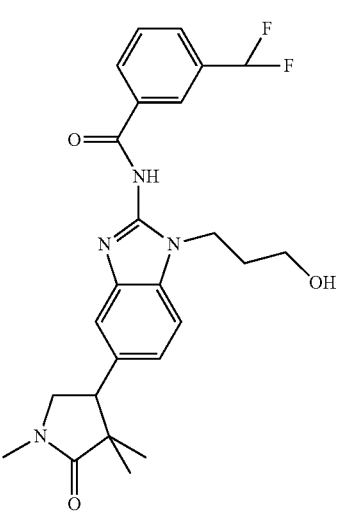 [SMILES: CN1CC(c2ccc3c(c2)nc(NC(=O)c2cccc(C(F)F)c2)n3CCCO)C(C)(C)C1=O]

The title compound was obtained following procedure described for example 23 but starting from 4-[2-amino-1-(3-hydroxypropyl)-1H-1,3-benzodiazol-5-yl]-1,3,3-trimethylpyrrolidin-2-one (intermediate 15, 20 mg, 0.06 mmol, 1.00 equiv) and 3-(difluoromethyl)benzoic acid (10.3 mg, 0.06 mmol, 1.00 equiv,) as a white solid (5 mg, 18%). 1H NMR (300 MHz, CDCl3) δ 12.55 (s, 1H), 8.42-8.32 (m, 2H), 7.67 (d, J=7.6 Hz, 1H), 7.56 (t, J=7.9 Hz, 1H), 7.29 (s, 1H), 7.23-7.10 (m, 2H), 4.69 (t, J=7.1 Hz, 1H), 4.54-4.43 (m, 2H), 3.55 (dd, J=22.7, 6.8 Hz, 4H), 3.32 (t, J=7.9 Hz, 1H), 2.97 (s, 3H), 2.05 (td, J=10.0, 8.4, 4.1 Hz, 2H), 1.24 (s, 3H), 0.74 (s, 3H). ESI+ (M+1): 471.3. mp: 95-96 OC.

Examples 27a and 27b: 3-(difluoromethyl)-N-[1-(3-hydroxypropyl)-5-[(3R)-1,4,4-trimethyl-5-oxopyrrolidin-3-yl]-1H-1,3-benzodiazol-2-yl]benzamide (27a) and 3-(difluoromethyl)-N-[1-(3-hydroxypropyl)-5-[(3S)-1,4,4-trimethyl-5-oxopyrrolidin-3-yl]-1H-1,3-benzodiazol-2-yl]benzamide (27b)

The two enantiomers of 3-Difluoromethyl-N-[1-(3-hydroxy-propyl)-5-(1,4,4-trimethyl-5-oxo-pyrrolidin-3-yl)-1H-benzoimidazol-2-yl]-benzamide were separated by chiral prep HPLC (column IC, 21.2×250 mm, 5 jam, hexane: EtOH, 50:50). First eluting fraction: 27a, 20 mg of a white solid, mp: 94-95 OC, Second elution fraction: 27b, 20 mg of a white solid. mp: 94-95° C.

Example 28: N-[1-(2-Fluoro-3-hydroxy-2-methyl-propyl)-5-(4-methyl-3-oxo-morpholin-2-yl)-1H-benzoimidazol-2-yl]-3-trifluoromethyl-benzamide (28)

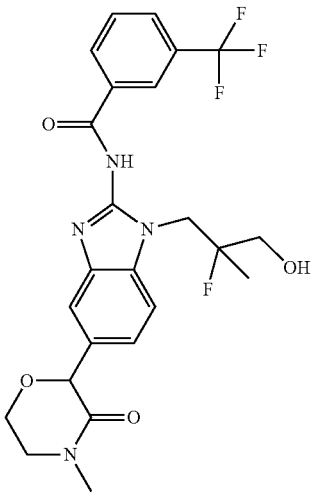 [SMILES: CN1CCOC(c2ccc3c(c2)nc(NC(=O)c2cccc(C(F)(F)F)c2)n3CC(C)(F)CO)C1=O]

The title compound was obtained following procedure described for example 26 but starting from 2-[2-amino-1-[3-(benzyloxy)-2-fluoro-2-methylpropyl]-1H-1,3-benzodiazol-5-yl]-4-methylmorpholin-3-one (intermediate 16, 100 mg, 0.21 mmol, 1.00 equiv) and 3-(trifluoromethyl)benzoic acid (50 mg, 0.26 mmol, 1.22 equiv) as a white solid (80 mg, 67%, 2 steps). 1H NMR (300 MHz, DMSO-d6) δ 12.87 (s, 1H), 8.56-8.45 (m, 2H), 7.90 (d, J=7.9 Hz, 1H), 7.78-7.69 (m, 1H), 7.60-7.53 (m, 1H), 7.43 (dd, J=8.6, 2.2 Hz, 1H), 7.25 (d, J=8.2 Hz, 1H), 5.40 (s, 1H), 5.19 (s, 1H), 4.72-4.40 (m, 2H), 4.05-3.85 (m, 2H), 3.72-3.51 (m, 3H), 3.44-3.38 (m, 1H), 2.93 (s, 3H), 1.32 (d, J=22.2 Hz, 3H). ESI+ (M+1): 509.2. mp: 121-124 OC.

Example 29: N-[5-(1,3-Dimethyl-2-oxo-pyrrolidin-3-yl)-1-(3-hydroxy-propyl)-1H-benzoimidazol-2-yl]-3-trifluoromethyl-benzamide (29)

Step 1: N-(1-{3-[(tert-butyldimethylsilyl)oxy]propyl}-5-(1,3-dimethyl-2-oxopyrrolidin-3-yl)-1H-1,3-benzodiazol-2-yl)-3-(trifluoromethyl)benzamide

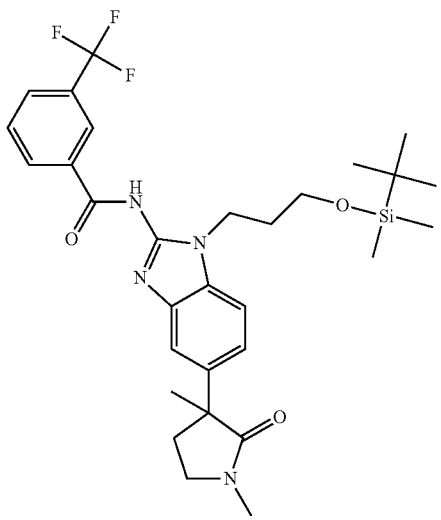 [SMILES: CN1CCC(C)(c2ccc3c(c2)nc(NC(=O)c2cccc(C(F)(F)F)c2)n3CCCO[Si](C)(C)C(C)(C)C)C1=O]

A mixture of 3-(2-amino-1-[3-[(tert-butyldimethylsilyl)oxy]propyl]-1H-1,3-benzodiazol-5-yl)-1,3-dimethylpyrrolidin-2-one (Intermediate 17, 250 mg, 0.54 mmol, 1.00 equiv), 3-(trifluoromethyl)benzoic acid (137 mg, 0.71 mmol, 1.31 equiv), HATU (231 mg, 0.60 mmol, 1.10 equiv) and DIEA (107 mg, 0.81 mmol, 1.50 equiv) in DMF (3 mL) was stirred at RT for 2 h. The solvent was removed under reduced pressure and the crude was purified by flash chromatography on silica (DCM: MeOH, gradient from 100:1 to 30:1) to afford the title compound as a yellow solid (270 mg, 76%). ESI$^+$ (M+1): 589.2.

Step 2: N-[5-(1,3-Dimethyl-2-oxo-pyrrolidin-3-yl)-1-(3-hydroxy-propyl)-1H-benzoimidazol-2-yl]-3-trifluoromethyl-benzamide

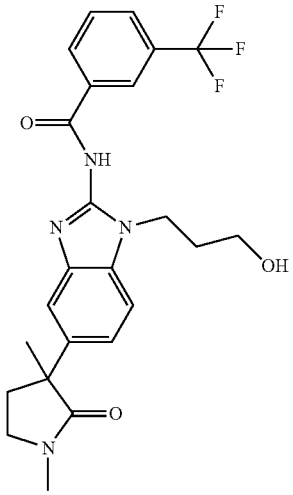 [SMILES: CN1CCC(C)(c2ccc3c(c2)nc(NC(=O)c2cccc(C(F)(F)F)c2)n3CCCO)C1=O]

Hydrogen chloride (250 mg, 6.72 mmol, 17.58 equiv,) was introduced in a solution of N-(1-[3-[(tert-butyldimethylsilyl)oxy]propyl]-5-(1,3-dimethyl-2-oxopyrrolidin-3-yl)-1H-1,3-benzodiazol-2-yl)-3-(trifluoromethyl)benzamide (250 mg, 0.38 mmol, 1.00 equiv) in dioxane (3 mL). The reaction mixture was stirred for 2 h at RT and concentrated under vacuum. Purification by Prep-HPLC afforded the title compound as a white solid (35 mg, 19%). 1H NMR (300 MHz, DMSO-d6, ppm) δ 12.71 (s, 1H), 8.57-8.47 (m, 2H), 7.94-7.84 (m, 1H), 7.79-7.67 (m, 1H), 7.64-7.57 (m, 1H), 7.48 (d, J=8.5 Hz, 1H), 7.29 (dd, J=8.5, 1.8 Hz, 1H), 4.65 (t, J=5.1 Hz, 1H), 4.32 (t, J=6.9 Hz, 2H), 3.53-3.43 (m, 2H), 3.41-3.33 (m, 1H), 3.32-3.23 (m, 1H), 2.83 (s, 3H), 2.38-2.28 (m, 1H), 2.22-2.10 (m, 1H), 2.01-1.90 (m, 2H), 1.45 (s, 3H). ESI$^+$ (M+1): 475.2. mp: 72-74° C.

Examples 29a and 29b: N-{5-[(3R)-1,3-dimethyl-2-oxopyrrolidin-3-yl]-1-(3-hydroxypropyl)-1H-1,3-benzodiazol-2-yl}-3-(trifluoromethyl)benzamide (29a) and N-{5-[(3S)-1,3-dimethyl-2-oxopyrrolidin-3-yl]-1-(3-hydroxypropyl)-1H-1,3-benzodiazol-2-yl}-3-(trifluoromethyl)benzamide (29b)

The two enantiomers of N-[5-(1,3-Dimethyl-2-oxo-pyrrolidin-3-yl)-1-(3-hydroxy-propyl)-1H-benzoimidazol-2-yl]-3-trifluoromethyl-benzamide were separated by chiral prep HPLC (column alpha Phenomenex Lux, 21.2×250 mm, 5 μm, hexane:EtOH, 50:50). First eluting fraction: 29a, 30 mg of a white solid, mp: 78-81 OC, Second elution fraction: 29b, 30 mg of a white solid. mp: 78-81° C.

Example 30: 3-Difluoromethyl-N-[5-(1,3-dimethyl-2-oxo-pyrrolidin-3-yl)-1-(3-hydroxy-propyl)-1H-benzoimidazol-2-yl]-benzamide (30)

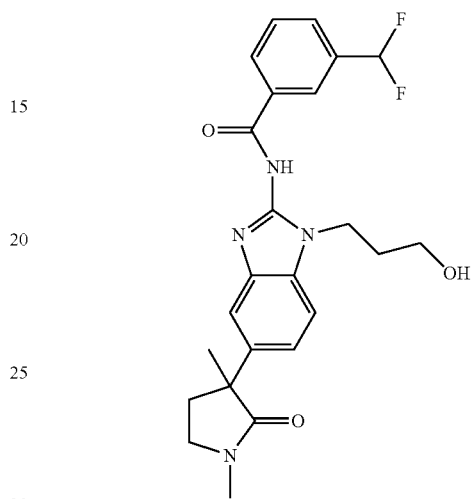

The title compound was obtained following procedure described for example 29 but starting from 3-(2-amino-1-[3-[(tert-butyldimethylsilyl)oxy]propyl]-1H-1,3-benzodiazol-5-yl)-1,3-dimethylpyrrolidin-2-one (Intermediate 17, 250 mg, 0.54 mmol, 1.00 equiv) and 3-(difluoromethyl)benzoic acid (124 mg, 0.71 mmol, 1.31 equiv) as a white solid (30 mg, 13%, 2 steps). 1H NMR (300 MHz, DMSO-d6) δ 12.69 (s, 1H), 8.45-8.36 (m, 2H), 7.76-7.68 (m, 1H), 7.68-7.56 (m, 2H), 7.52-7.42 (m, 1H), 7.36-6.93 (m, 2H), 4.65 (t, J=5.1 Hz, 1H), 4.31 (t, J=6.8 Hz, 2H), 3.51-3.42 (m, 2H), 3.41-3.33 (m, 1H), 3.32-3.22 (m, 1H), 2.83 (s, 3H), 2.38-2.26 (m, 1H), 2.22-2.08 (m, 1H), 2.03-1.89 (m, 2H), 1.44 (s, 3H). ESI$^+$ (M+1): 457.2. mp: 78-81° C.

Examples 30a and 30b: N-{5-[(3R)-1,3-dimethyl-2-oxopyrrolidin-3-yl]-1-(3-hydroxypropyl)-1H-1,3-benzodiazol-2-yl}-3-(diifluoromethyl)benzamide (30a) and N-{5-[(3S)-1,3-dimethyl-2-oxopyrrolidin-3-yl]-1-(3-hydroxypropyl)-1H-1,3-benzodiazol-2-yl}-3-(diifluoromethyl)benzamide (30b)

The two enantiomers of N-[5-(1,3-Dimethyl-2-oxo-pyrrolidin-3-yl)-1-(3-hydroxy-propyl)-1H-benzoimidazol-2-yl]-3-diifluoromethyl-benzamide were separated by chiral prep HPLC (column alpha Phenomenex Lux, 21.2×250 mm, 5 micron, hexane:EtOH, 50:50). First eluting fraction: 30a, 30 mg of a white solid, mp: 78-81° C., Second elution fraction: 30b, 30 mg of a white solid. mp: 78-81° C.

Example 31: 3-Difluoromethyl-N-[5-(1,2-dimethyl-5-oxo-pyrrolidin-2-yl)-1-(3-hydroxy-propyl)-1H-benzoimidazol-2-yl]-benzamide (31)

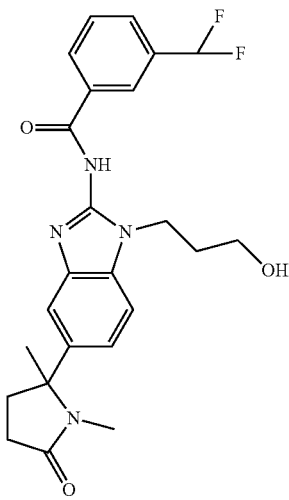 [SMILES: CN1C(=O)CCC1(C)c1ccc2c(c1)nc(NC(=O)c1cccc(C(F)F)c1)n2CCCO]

The title compound was obtained following procedure described for example 29, step 1 but starting from 5-[2-amino-1-(3-hydroxypropyl)-1H-1,3-benzodiazol-5-yl]-1,5-dimethylpyrrolidin-2-one (Intermediate 18, 200 mg, 0.60 mmol, 1.00 equiv) and 3-(difluoromethyl)benzoic acid (108 mg, 0.60 mmol, 1.00 equiv) as a white solid (90 mg, 33%). 1H NMR (300 MHz, CDCl$_3$) δ 12.52 (s, 1H), 8.41-8.28 (m, 2H), 7.70-7.60 (m, 1H), 7.56-7.51 (m, 1H), 7.29-7.25 (m, 2H), 7.16-7.13 (m, 1H), 6.70 (t, J=56.4 Hz, 1H), 4.63-4.59 (m, 1H), 4.52-4.39 (m, 2H), 3.50-3.45 (m, 2H), 2.66 (s, 3H), 2.50-2.44 (m, 2H), 2.22-1.95 (m, 4H), 1.68 (s, 3H). ESI$^+$ (M+1): 457.2. pm: 98-99° C.

Examples 31a and 31b: 3-(difluoromethyl)-N-{5-[(2R)-1,2-dimethyl-5-oxopyrrolidin-2-yl]-1-(3-hydroxypropyl)-1H-1,3-benzodiazol-2-yl}benzamide (31a) and 3-(difluoromethyl)-N-{5-[(2S)-1,2-dimethyl-5-oxopyrrolidin-2-yl]-1-(3-hydroxypropyl)-1H-1,3-benzodiazol-2-yl}benzamide (31b)

The two enantiomers of 3-Difluoromethyl-N-[5-(1,2-dimethyl-5-oxo-pyrrolidin-2-yl)-1-(3-hydroxy-propyl)-1H-benzoimidazol-2-yl]-benzamide were separated by chiral prep HPLC (column CHIRAL ART cellulose SB Lux, 20×250 mm, hexane:EtOH, 65:35). First eluting fraction: 31a, 24 mg of a brown solid, mp: 98-99 OC, Second elution fraction: 31b, 21 mg of a beige solid. mp: 98-99° C.

Example 32: N-[5-(1,2-Dimethyl-5-oxo-pyrrolidin-2-yl)-1-(3-hydroxy-propyl)-1H-benzoimidazol-2-yl]-3-trifluoromethyl-benzamide (32)

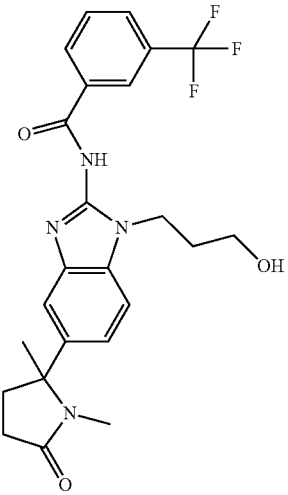 [SMILES: CN1C(=O)CCC1(C)c1ccc2c(c1)nc(NC(=O)c1cccc(C(F)(F)F)c1)n2CCCO]

The title compound was obtained following procedure described for but example 31 starting 5-[2-amino-1-(3-hydroxypropyl)-1H-1,3-benzodiazol-5-yl]-1,5-dimethylpyrrolidin-2-one (Intermediate 18, 300 mg, 0.89 mmol, 1.00 equiv) and 3-(trifluoromethyl)benzoic acid (179 mg, 0.89 mmol, 1.00 equiv), as a white solid (90 mg, 21%). 1H NMR (300 MHz, CDCl$_3$) δ 12.56 (s, 1H), 8.56-8.38 (m, 2H), 7.77-7.7 (m, 1H), 7.59-7.45 (m, 1H), 7.35-7.27 (m, 2H), 7.19-7.17 (m, 1H), 4.58-4.36 (m, 2H), 3.54-3.50 (m, 2H), 2.69 (s, 3H), 2.50-2.47 (m, 2H), 2.23-1.99 (m, 4H), 1.72 (s, 3H). ESI$^+$ (M+1): 475.2. mp: 99-100 OC.

Examples 32a and 32b: N-{5-[(2R)-1,2-dimethyl-5-oxopyrrolidin-2-yl]-1-(3-hydroxypropyl)-1H-1,3-benzodiazol-2-yl}-3-(trifluoromethyl)benzamide (32a) and N-{5-[(2S)-1,2-dimethyl-5-oxopyrrolidin-2-yl]-1-(3-hydroxypropyl)-1H-1,3-benzodiazol-2-yl}-3-(trifluoromethyl)benzamide (32b)

The two enantiomers of N-[5-(1,2-Dimethyl-5-oxo-pyrrolidin-2-yl)-1-(3-hydroxy-propyl)-1H-benzoimidazol-2-yl]-3-trifluoromethyl-benzamide were separated by chiral prep HPLC (column ChiralPak ID, 20×250 mm, 5 micron, MTBE:EtOH, 70:30).

First eluting fraction: 32a, 32 mg of a white, mp: 99-100 OC, Second elution fraction: 32b, 29 mg of a white solid. mp: 99-100° C.

Example 33: Enzymatic Assays

IRAK4 Enzymatic Assay

IRAK4 is a human purified recombinant enzyme (His-TEV-IRAK4 (1-460)).

In this assay, IRAK4 hydrolyses ATP, autophosphorylates and phosphorylates a Serine/Threonine generic peptidic substrate (STK: 61ST1BLC from CisBio International). Measurement of IRAK-4 inhibition is performed in 384-well format based on a luminescence assay (ADP-Glo™ Kinase Assay from Promega). Purified human recombinant IRAK4 (0.3 g/mL) and serial diluted compounds in DMSO (range of concentration from 10 μM to 0.5 nM) or controls (1% DMSO) are incubated for 15 minutes at RT in assay buffer containing 50 mM Hepes pH 7.0, Fatty acid-free BSA 0.1%, Dithiothreitol (DTT) 2 mM, MgCl2 10 mM, EGTA 0.5 mM, Triton X-100 0.01%, MnCl2 5 mM. The kinase reaction is then initiated by the addition of ATP (2 M) and the peptidic substrate STK1-biotin peptide (300 nM). After 2 hours of incubation at RT, the reaction is stopped and the unconsumed ATP depleted by the addition of ADP-Glo™ Reagent according to supplier instructions. After 40 minutes of incubation at RT, the Kinase Detection Reagent is then added to the assay plate according to supplier instructions. After 20 minutes of incubation at RT, the luminescence signal is measured with a plate-reading luminometer (PerkinElmer Envision or equivalent reader).

IRAK1 Enzymatic Assay:

IRAK1 is a human purified recombinant enzyme (His-TEV-IRAK1 (194-712))

In this assay, IRAK1 hydrolyses ATP and autophosphorylates. Measurement of IRAK-1 inhibition is performed in 384-well format based on luminescence assay (ADP-Glo™ Kinase Assay from Promega). Purified human recombinant IRAK1 (0.3 g/ml) and serial diluted compounds in DMSO (range of concentration from 10 μM to 0.5 nM) or controls (1% DMSO) are incubated for 15 minutes at RT in assay buffer containing 50 mM Hepes pH 7.0, Fatty acid-free BSA 0.1%, Dithiothreitol (DTT) 2 mM, MgCl2 10 mM, EGTA 0.5 mM, Triton X-100 0.01%. The kinase reaction is then initiated by the addition of ATP at a concentration of 1 μM. After 2 hours of incubation at RT, the reaction is stopped and the unconsumed ATP depleted by the addition of ADP-Glo™ Reagent according to supplier instructions. After 40 minutes of incubation at RT, the Kinase Detection Reagent is then added to the assay plate according to supplier instructions. After 20 minutes of incubation at RT, the luminescence signal is measured with a luminometer (PerkinElmer Envision or equivalent reader).

TLR7 Induced IL-6 in Human PBMC's

Human PBMC assay was used as one of the functional assaya to monitor the activity of IRAK1 and IRAK4 small molecule inhibitors on TLR7 induced IL-6 secretion in human mononuclear cells (PBMC's). Human PBMCs were prepared from buffy coats (whole blood enriched with leukocytes and platelets) obtained from healthy volunteers used either fresh or frozen are plated in assay media (RPMI+ 2% P/S/L-glu+10% HI-FBS) and pre-treated with compounds in DMSO/media (range of concentrations from 25 uM to 0.4 nM) or controls (0.25% DMSO) for 30 minutes at 37° C. in assay media. Following pre-treatment with IRAK1 and IRAK4 inhibitors, PBMC's were stimulated with TLR7 specific ligand (2 uM) overnight (16-18 hrs) at 37° C. After incubation supernatant was transferred to 384 well PE AlphaPlate-384 (6005350) and IL-6 is quantified using Perkin Elmer IL-6 Alpha LISA kit (AL223C). Plates were read on an Envision® plate reader with Alpha Technology®.

Results are given in the following table.

TABLE 2

| Compound | IRAK 1 | IRAK4 | PBMC |
| --- | --- | --- | --- |
| 1 | *** | *** | *** |
| 1a | *** | *** | *** |
| 1b | ** | *** | * |
| 2a | ** | *** | NT |
| 2b | ** | *** | *** |
| 3a | * | *** | ** |
| 3b | * | *** | ** |
| 3c | ** | *** | *** |
| 3d | *** | *** | *** |
| 4 | ** | *** | NT |
| 5 | ** | *** | ** |
| 6 | ** | *** | NT |
| 7 | ** | *** | ** |
| 8 | *** | *** | NT |
| 9 | ** | *** | NT |
| 10 | ** | *** | ** |
| 11 | * | *** | NT |
| 12 | ** | *** | ** |
| 13 | *** | *** | ** |
| 14 | *** | *** | *** |
| 15 | *** | *** | *** |
| 16 | ** | *** | ** |
| 17 | ** | *** | ** |
| 18 | ** | *** | ** |
| 19 | ** | *** | ** |
| 20 | ** | *** | ** |
| 20a | ** | *** | ** |
| 20b | ** | *** | * |
| 21 | ** | *** | *** |
| 21a | ** | *** | ** |
| 21b | ** | *** | ** |
| 21c | ** | *** | *** |
| 21d | *** | *** | ** |
| 22 | ** | *** | *** |
| 22a | ** | *** | *** |
| 22b | *** | *** | *** |
| 22c | ** | *** | * |
| 22d | ** | *** | ** |
| 23 | ** | *** | *** |
| 23a | ** | *** | *** |
| 23b | ** | *** | ** |
| 24 | ** | *** | *** |
| 25 | *** | *** | ** |
| 25a | *** | *** | ** |
| 25b | ** | *** | ** |
| 26 | ** | *** | ** |
| 27 | ** | *** | ** |
| 27a | *** | *** | ** |
| 27b | ** | *** | ** |
| 28 | ** | *** | *** |
| 29 | * | *** | NT |
| 29a | * | *** | * |
| 29b | ** | *** | ** |
| 30 |  | *** | * |
| 30a | * | *** | * |
| 30b | ** | *** | * |
| 31 | ** | *** | * |
| 31a | ** | *** | * |
| 31b | * | *** | * |
| 32 | ** | *** | * |
| 32a | ** | *** | * |
| 32b | ** | *** | * |

IC$_{50}$ *** ≤100 nM
IC$_{50}$ ** >100 nM to 1 μM
IC$_{50}$ * >1 μM to 10 uM
NT: Not tested Example 34. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I,

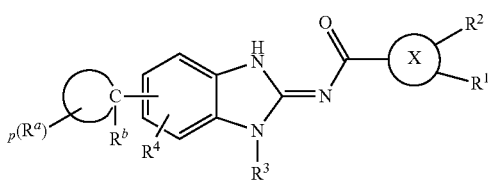

or a pharmaceutically acceptable salt thereof, wherein:

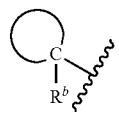

is a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur;

each $R^a$ is independently —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;

$R^b$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$; or $R^b$ is absent;

Ring X is selected from:

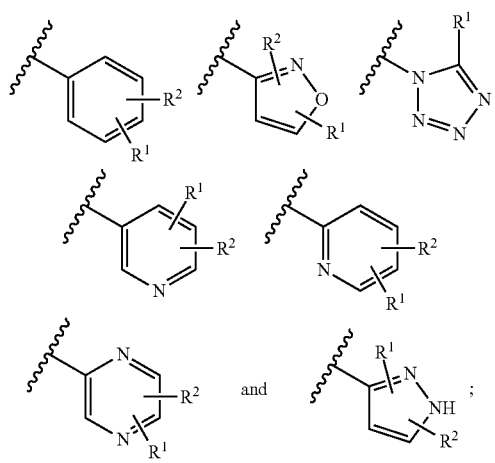

$R^1$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;

$R^2$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;

$R^3$ is $C_{1-6}$ aliphatic, $C_{3-10}$ aryl, or a 5-6 membered monocyclic heteroaryl ring having 1-4 heteroatoms independently selected from nitrogen, oxygen, or sulfur; each of which is optionally substituted; or $R^3$ is -haloalkyl;

$R^4$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;

each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; and p is 0, 1, 2, 3, 4, or 5.

2. The compound of claim 1, wherein

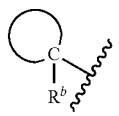

is cyclohexanone, furanone, piperidinone, pyridinone, pyrimidinone, pyrrolidinone, or oxetanyl.

3. The compound of claim 1, wherein

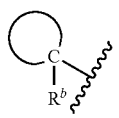

is selected from:

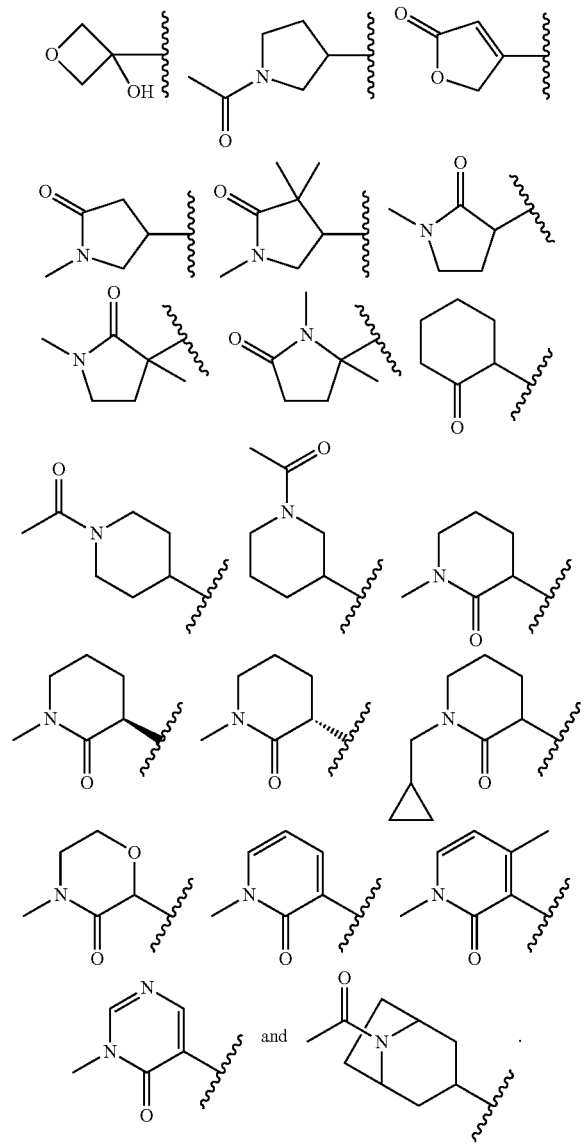

4. The compound of claim 1, wherein Ring X is:

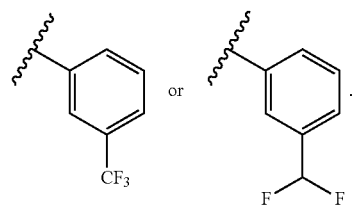 [SMILES: *c1cccc(C(F)(F)F)c1 ; *c1cccc(C(F)F)c1]

5. The compound of claim 1, wherein $R^3$ is $C_{1-6}$ aliphatic which is optionally substituted.

6. The compound of claim 5, wherein $R^3$ is methyl, ethyl, propyl, i-propyl, n-butyl, s-butyl, t-butyl, a straight chain or branched pentyl, or a straight chain or branched hexyl; each of which is optionally substituted.

7. The compound of claim 6, wherein $R^3$ is selected from:

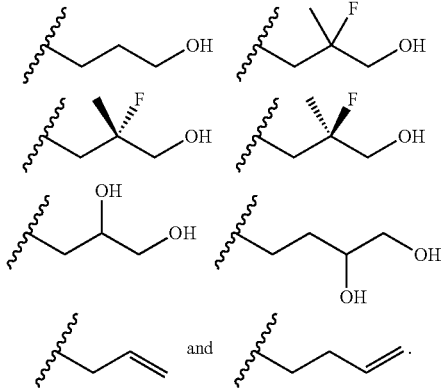

8. The compound of claim 1, of formula I-a,

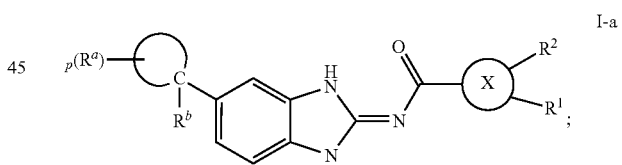

or a pharmaceutically acceptable salt thereof.

9. The compound of claim 1, of formula I-b,

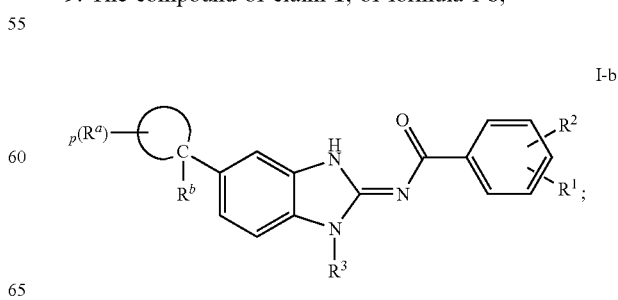

or a pharmaceutically acceptable salt thereof.

10. The compound of claim 9, wherein
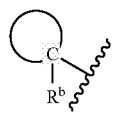
is selected from:
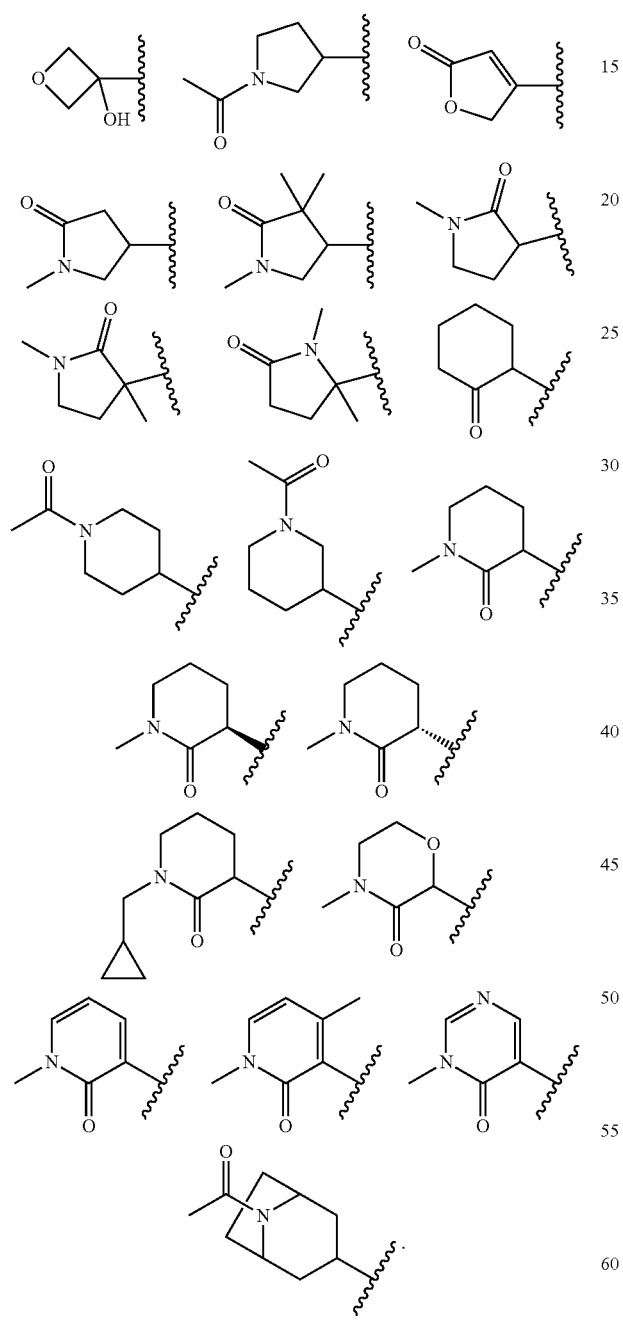
11. The compound of claim 9, wherein $R^1$ is -haloalkyl.
12. The compound of claim 9, wherein $R^3$ is selected from:
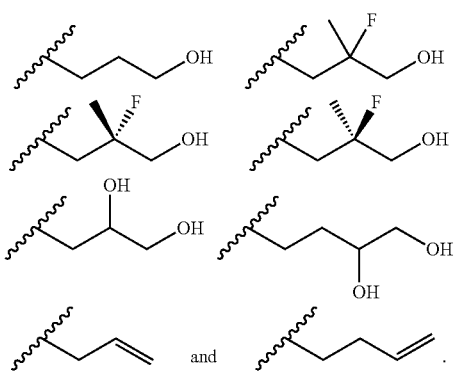
13. The compound of claim 1, of formula I-c,
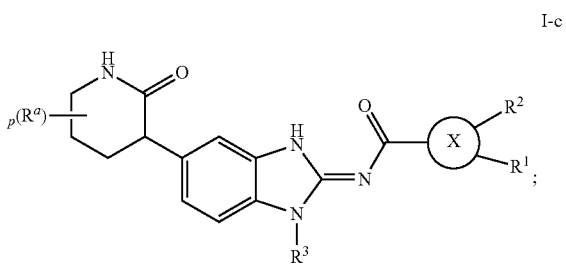
or a pharmaceutically acceptable salt thereof.
14. The compound of claim 1, selected from the following compounds from Table 1:
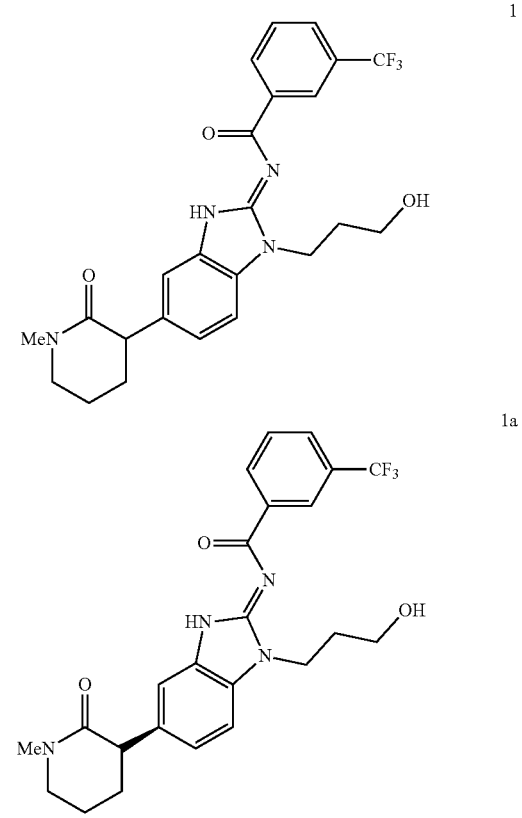

-continued
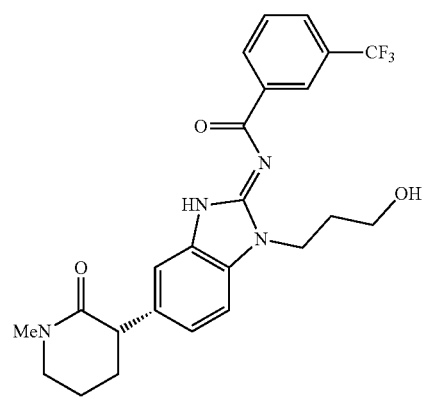
1b
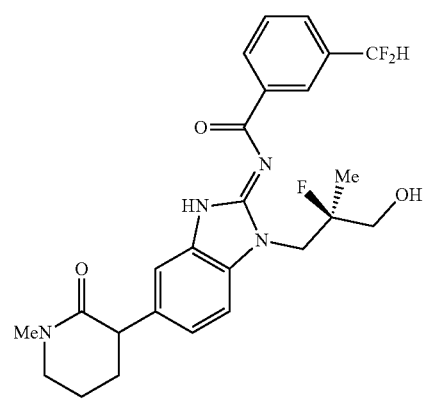
2a
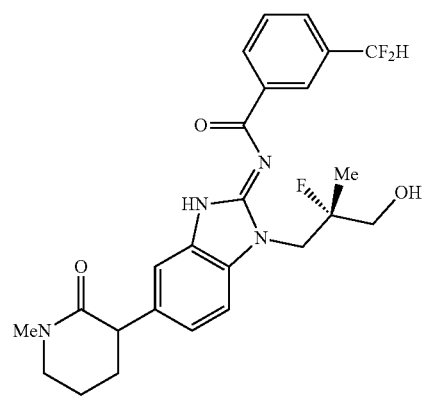
2b
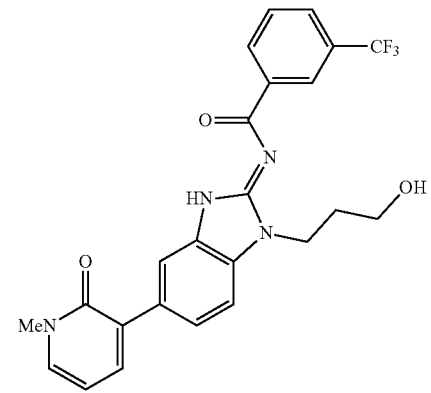
4
-continued
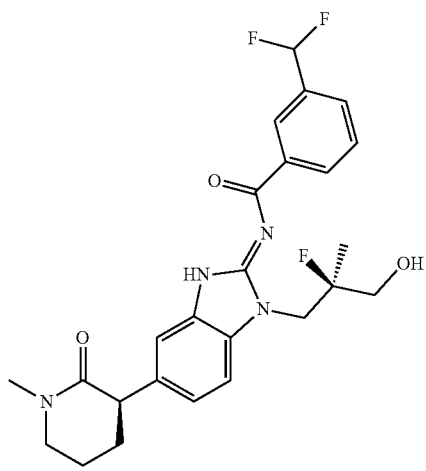
3a
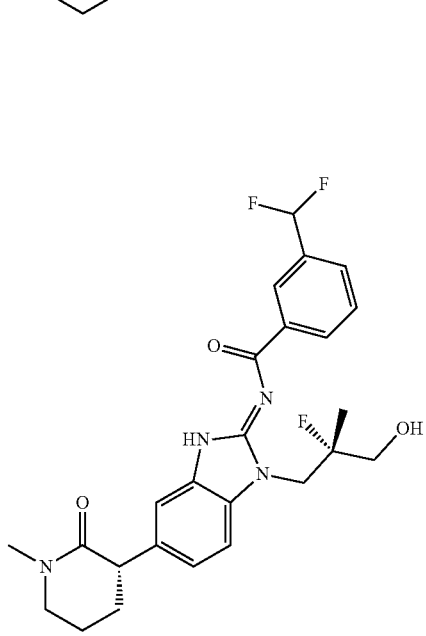
3b
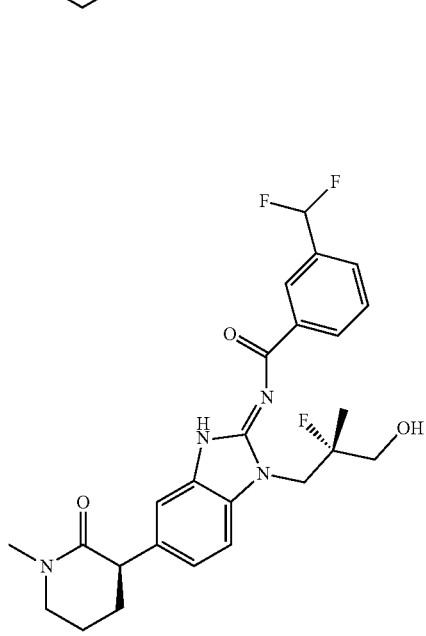
3c

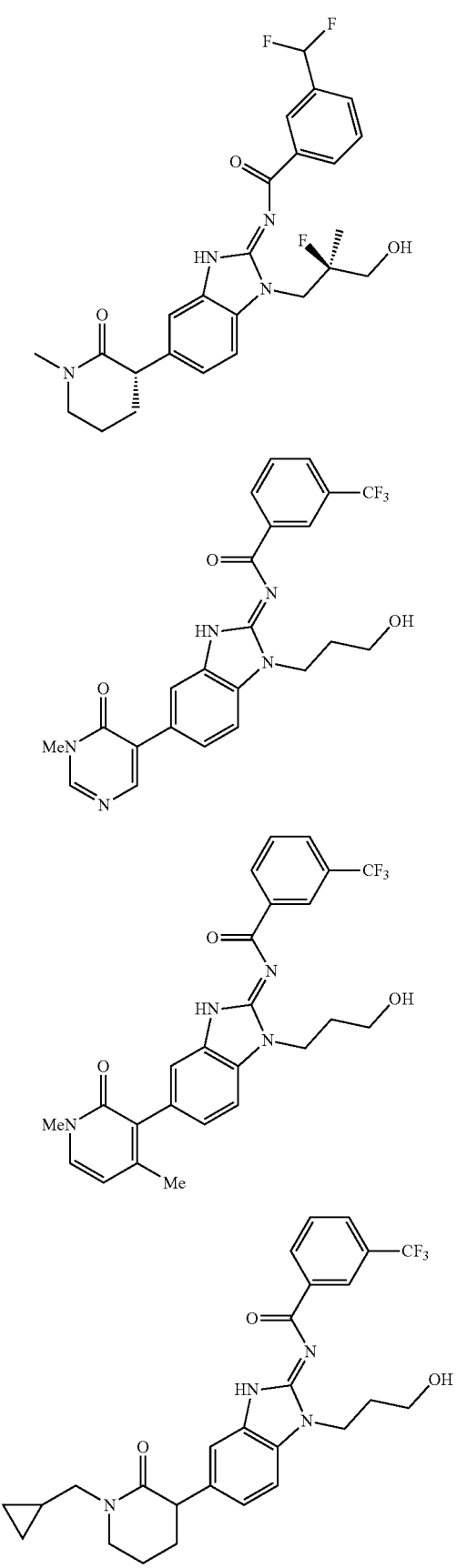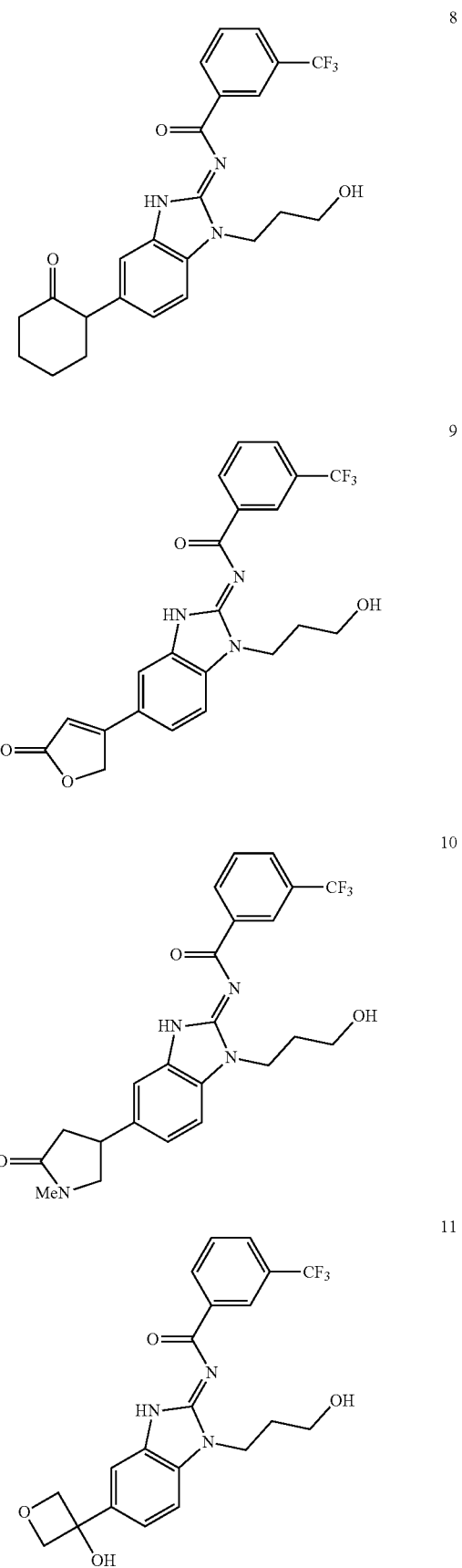

123
-continued
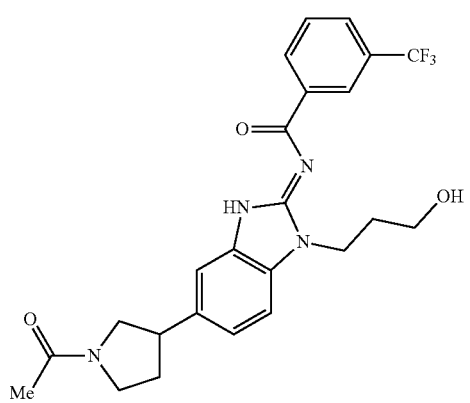
12
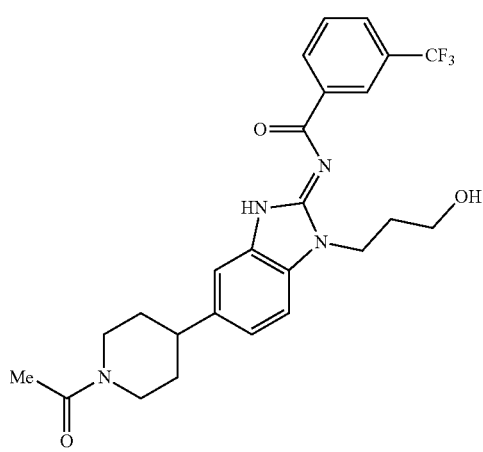
13
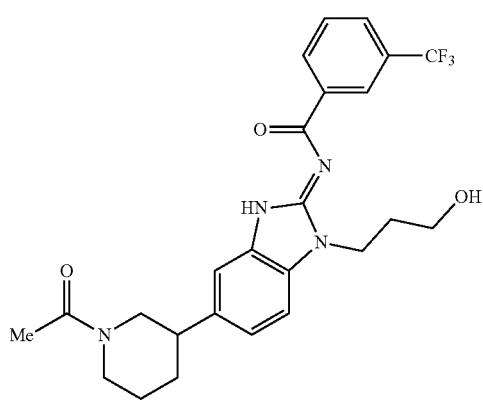
14
124
-continued
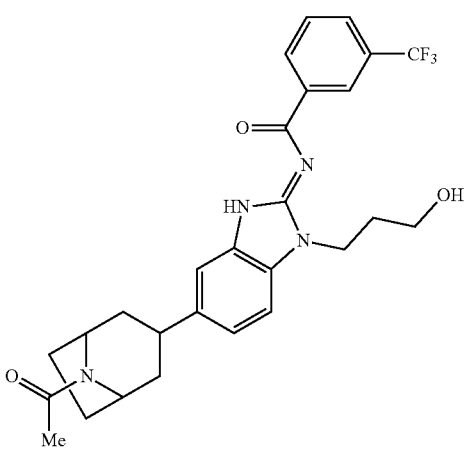
15
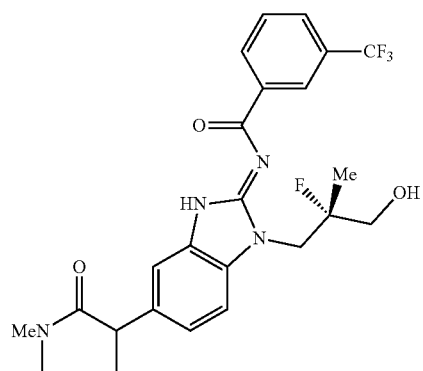
16
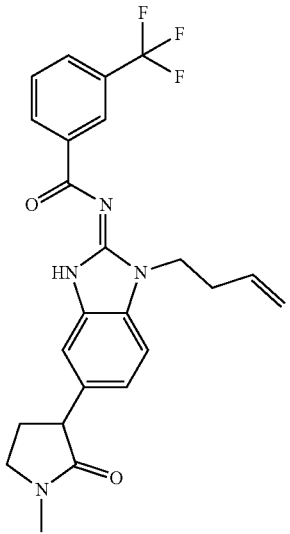
17

-continued
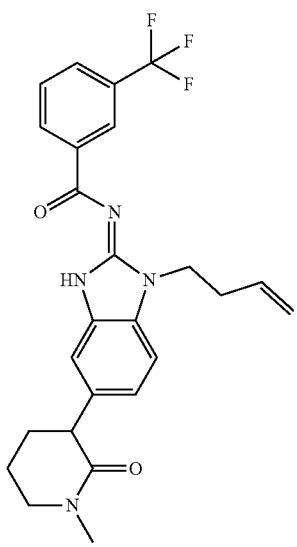
18
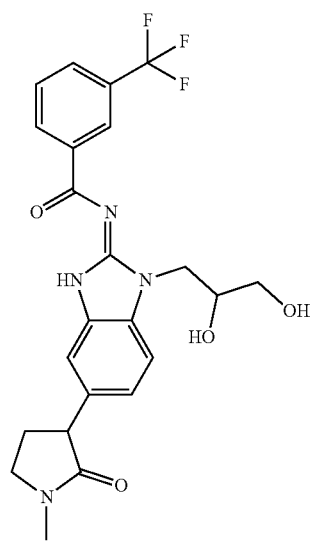
20a
19
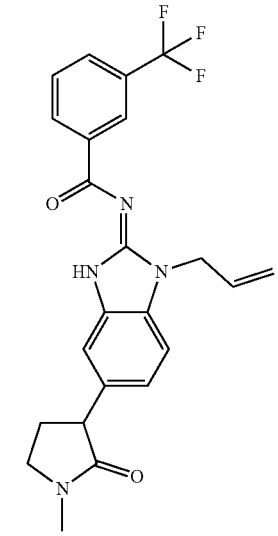
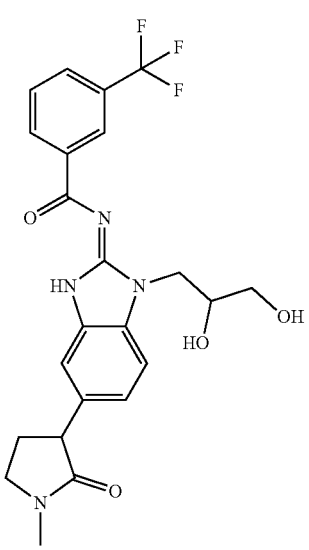
20b
20
21

21a 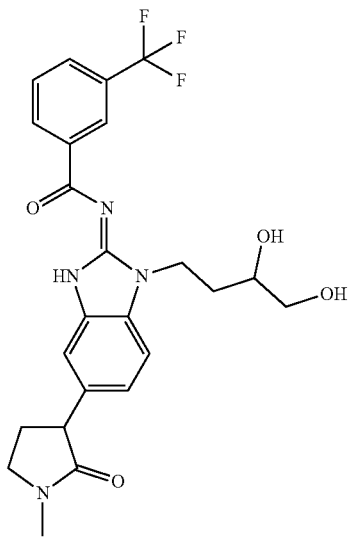
21b 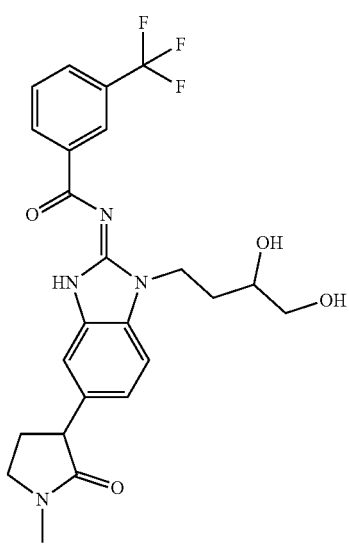
21c 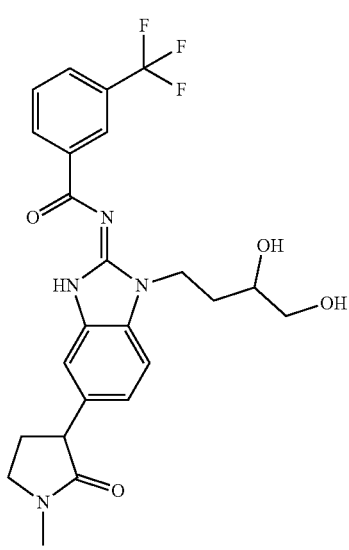
21d 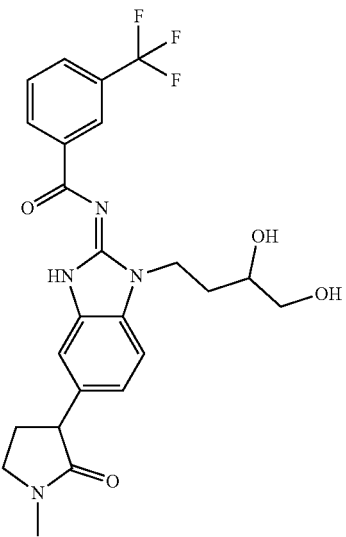
22 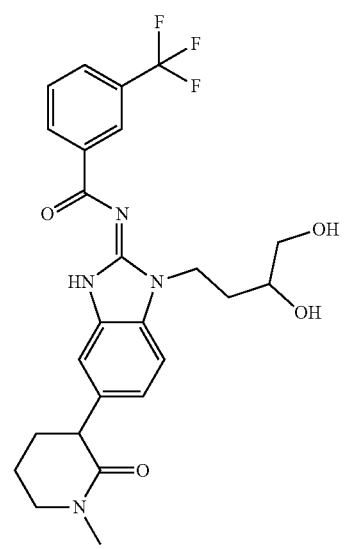
22a 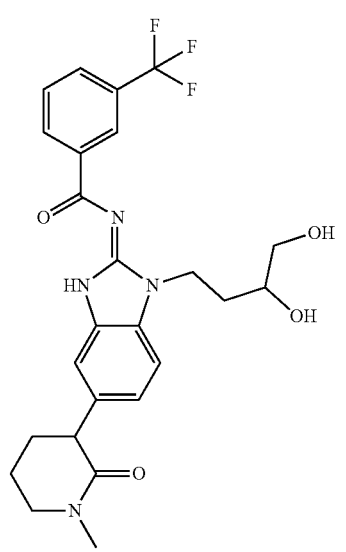

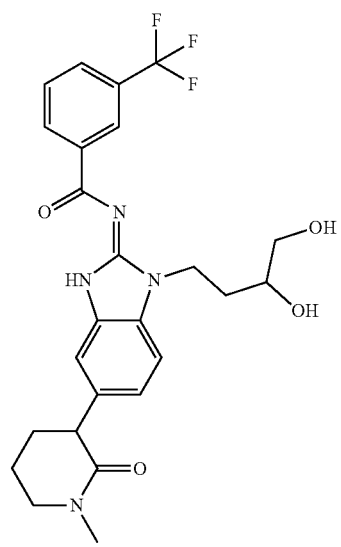
22b
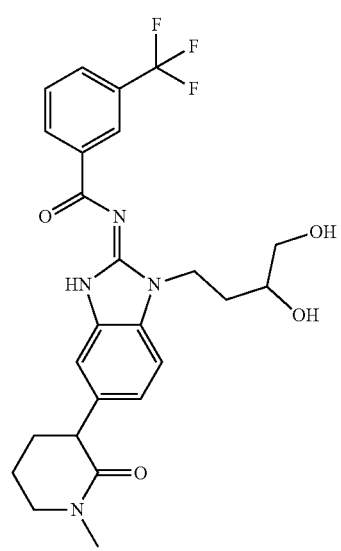
22c
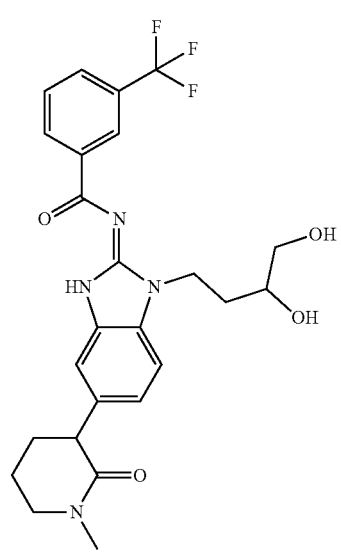
22d
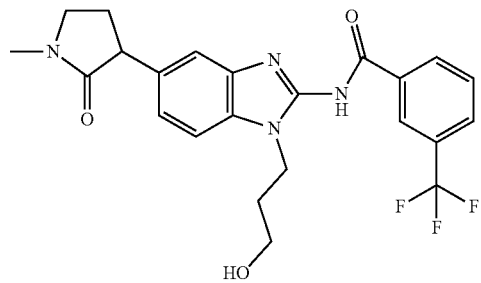
23
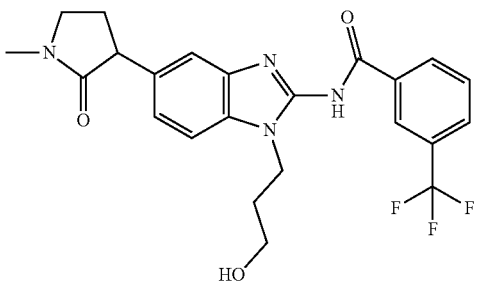
23a
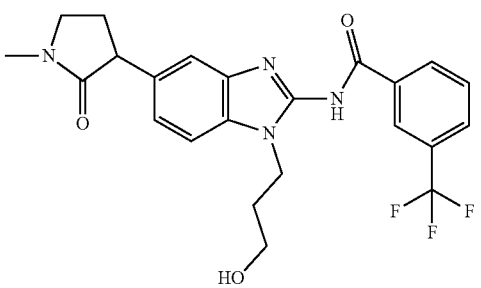
23b
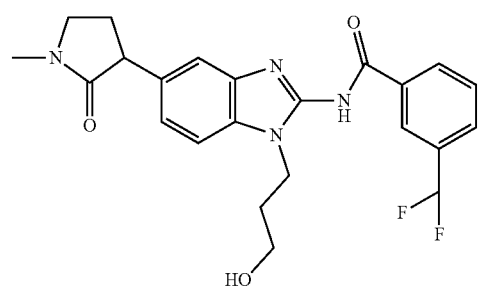
24
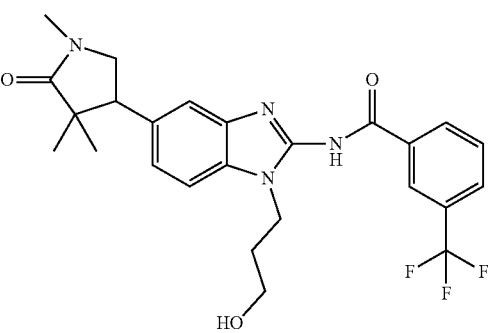
25

25a
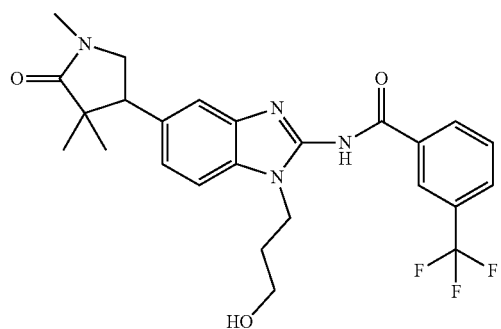
25b
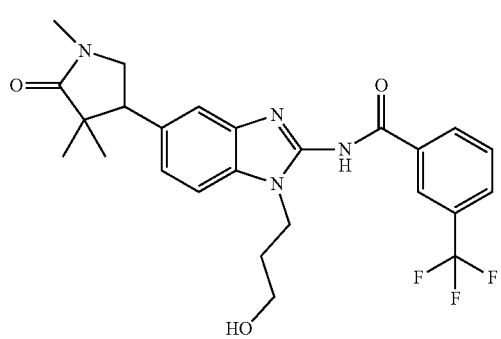
26
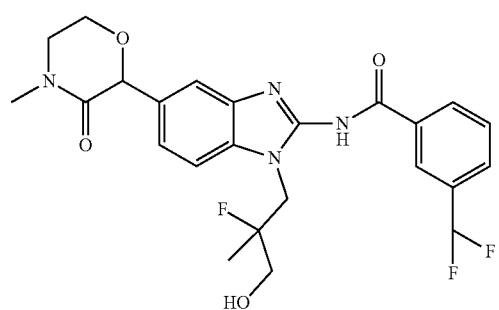
27
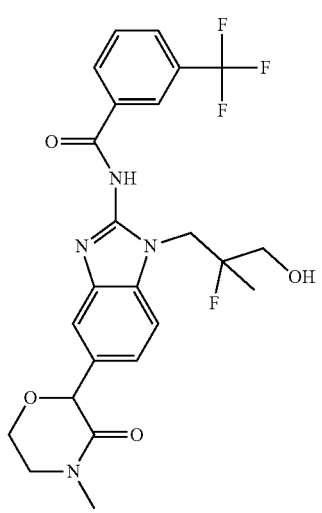
27a
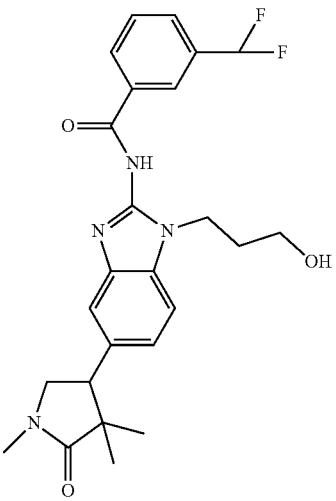
27b
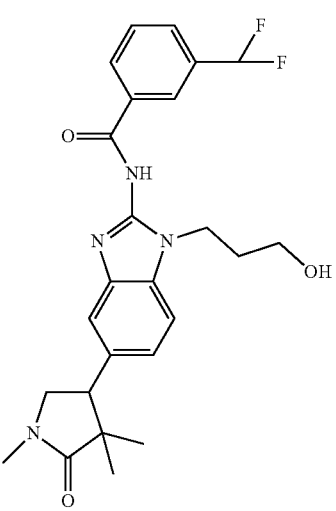
28
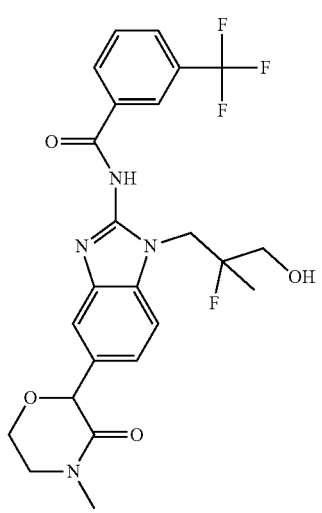

133
-continued
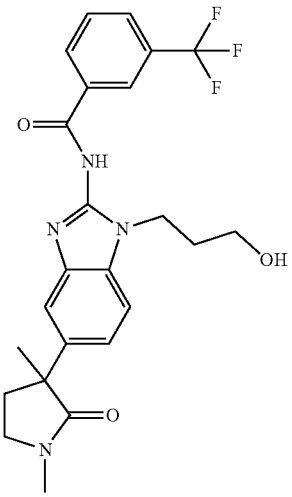
29
29a
29b
134
-continued
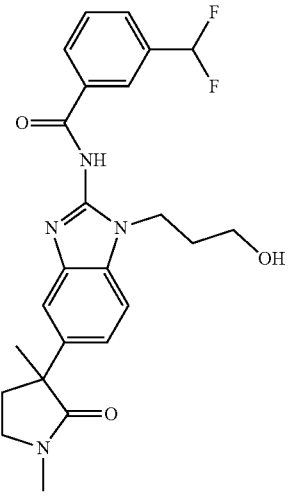
30
30a
30b

31 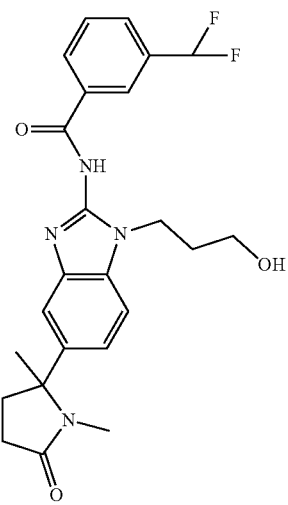
31a 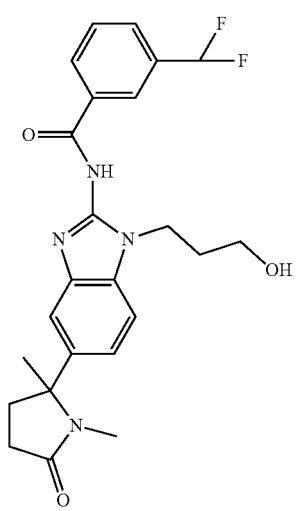
31b
32 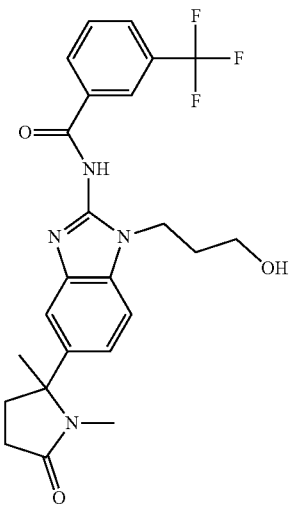
32a 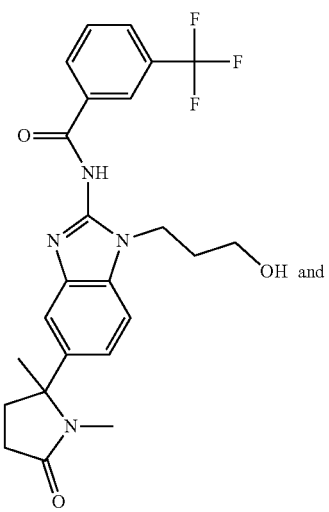
and
32b 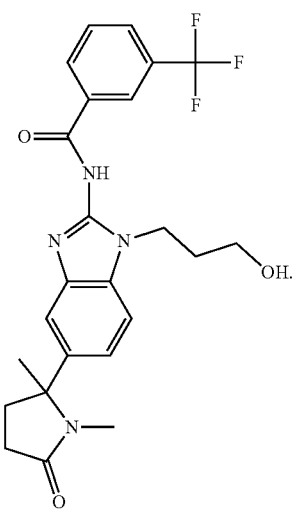
.
15. A pharmaceutical composition comprising a compound of claim 1, and a pharmaceutically acceptable adjuvant, carrier, or vehicle.
16. A method for inhibiting IRAK, or a mutant thereof, activity in a patient or in a biological sample, comprising the step of administering to said patient or contacting said biological sample with a compound of claim 1 or a physiologically acceptable salt thereof.

17. A method for treating an IRAK-mediated disorder in a patient in need thereof, comprising the step of administering to said patient a compound of claim 1.

18. The method of claim 17, wherein the disorder is selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

19. A method for treating cancer in a subject, comprising the step of administering to said subject a compound of claim 1 or a physiologically acceptable salt thereof.

20. The method of claim 18, wherein the disorder is selected from Rheumatoid Arthritis, Systemic Lupus Erythematosus, Lupus nephritis, and Multiple Sclerosis.

\* \* \* \* \*